US006238890B1

(12) United States Patent
Boime et al.

(10) Patent No.: US 6,238,890 B1
(45) Date of Patent: *May 29, 2001

(54) SINGLE CHAIN FORMS OF THE GLYCOPROTEIN HORMONE QUARTET

(75) Inventors: Irving Boime, St. Louis, MO (US); William R. Moyle, Piscataway, NJ (US)

(73) Assignee: Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/918,288

(22) Filed: Aug. 25, 1997

Related U.S. Application Data

(63) Continuation-in-part of application No. 08/853,524, filed on May 9, 1997, which is a continuation-in-part of application No. 08/475,049, filed on Jun. 7, 1995, now abandoned, which is a continuation-in-part of application No. 08/351,591, filed on Dec. 7, 1994, now abandoned, and application No. 08/351,591, which is a continuation-in-part of application No. 08/334,628, filed on Nov. 4, 1994, now Pat. No. 5,705,478, which is a continuation-in-part of application No. 08/310,590, filed on Sep. 22, 1994, now abandoned, which is a continuation-in-part of application No. 08/289,396, filed on Aug. 12, 1994, now abandoned, which is a continuation-in-part of application No. 08/199,382, filed on Feb. 18, 1994, now abandoned.

(51) Int. Cl.[7] .................................................. C12N 15/62
(52) U.S. Cl. ..................... 435/69.7; 435/325; 435/360; 435/252.3; 435/320.1; 536/23.4; 530/398
(58) Field of Search .................................. 435/69.7, 325, 435/360, 252.3, 320.1; 536/23.4; 935/10; 530/351, 397, 398

(56) References Cited

U.S. PATENT DOCUMENTS

| | | | |
|---|---|---|---|
| 4,751,180 | * 6/1988 | Cousens et al. | 435/172.3 |
| 4,923,805 | * 5/1990 | Reddy et al. | 435/69.4 |
| 5,177,193 | 1/1993 | Boime et al. | |
| 5,338,835 | 8/1994 | Boime | |
| 5,352,779 | * 10/1994 | Chappel et al. | 536/23.51 |
| 5,585,345 | * 12/1996 | Boime | 514/8 |
| 5,705,484 | * 1/1998 | Thomason | 514/12 |

FOREIGN PATENT DOCUMENTS

WO 85/01959   5/1985   (WO).

OTHER PUBLICATIONS

P. LaPolt et al., Endocrinology 131(6):2514, 1992.*
P. Narayan et al., Molecular Endocrinology 9(12):1720–1726, Dec. 1995.*
H. Xia et al., J. Molecular Endocrinology 10:337–343, 1993.*
S.M. Zurawski et al., EMBO J. 7(4):1061–1069, 1988.*
Design of a long–acting follitropin agaonist by fusing the C–terminal sequence of the chorionic gonadotropin beta submit to the follitropin beta subunit, Fares, F. et al., *Proc. of the Natl. Acad. of Sci of the US*, vol. 89, May 1992, pp. 4304–4308.
Comparison of the biological and immunological properties of glycosylation deficient human chorionic gonadotropin variants produced by site directed mutagenesis and chemical deglycosylation, Sairam, M. R. and Jiang, L. G., *Molecular and Cellular Endocrinology*, vol. 85, Jun. 1992, pp. 227–235.
Biosynthesis of a biologically active single peptide chain containing the human common alpha and chorionic gonadotropin beta subunits in tandem, Sugahara T. et al, *Proc. of the Natl Acad of Sci of the U.S..*, (Mar. 14, 1995) 92 (6) 2041–5.
Expression of biologically active fusion genes encoding the common alpha subunit and either the CGbeta or FSHbeta subunits: role of a linker sequence, Sugahara, T. et al. *Molecular and cellular endocrinology*, vol. 125, 1996, pp. 71–77.
*Chemical Abstracts*, vol. 115, No. 21, Nov. 25, 1991, p. 521.
*Chemical Abstracts*, vol. 113, No. 5, Jul. 30, 1990, p. 430.
*Chemical Abstracts*, vol. 108, No. 5, Feb. 01, 1988, p. 163.
*Chemical Abstracts*, vol. 97, No. 17, Oct. 25, 1982, p. 94.

* cited by examiner

*Primary Examiner*—Lorraine Spector
(74) *Attorney, Agent, or Firm*—Morrison & Foerster LLP

(57) ABSTRACT

Single-chain forms of the glycoprotein hormone quartet, at least some members of which are found in most vertebrates, are disclosed. The α and β subunits of the wild-type heterodimers or their variants or their fragments are covalently linked, optionally through a linker moiety. Some of the single-chain forms are agonists and others antagonists of the glycoprotein hormone activity.

40 Claims, 28 Drawing Sheets

Coding Sequence for Single Chain Gonadotropin Analog #1 and Primers (underlined)

```
              M   E   M   F   Q   G   L   L   L   L   L   L   L   S   M   G   G   T   W   A   S   K   E   P   L
5'-ATGAAATCGACGGAATCAGACTCGAGCCAAGGATGGAGATGTTCCAGGGCTGCTGTTGCTGCTGTGCTGCTGAGCATGGGCGGACATGGGCATCCAAGGAGCCGCTT-
              3'-GGTTCCTACCTCTACAAGGTCCCGACGACGACAAGACGACGACTCGTACCCGCCCTAGTTCCTCGGGAA
                     ctcgag(XhoI)

R   P   R   C   R   P   I   N   A   T   L   A   V   E   K   E   G   C   P   V   C   I   T   V   N   T   T   I   C   A   G   Y   C   P   T   M   T
CGGCCACGGTGCCGCCGCCCCATCAATGCCACCCTGGCTGTGGAGAAGGAGGGCTGCCCCGTGTGCATCACCGTCAACACCACCATCTGTGCCGGCTACTGCCCCACCATGACC-
GCCGGTGCCACGGCGGCGGGGGTAGTTACGGTGGGAGTCGACACCGATGACACCTCTTCCTCCCGACGGGGCACACGTTGTGGTAGCAGTTGTGTGGATGACGGGGTGGATCTGG-

R   V   L   Q   G   V   L   R   A   L   P   Q   V   V   C   N   Y   R   D   V   R   F   E   E   S   I   R   L   P   G   C   P   R   G   V   N   P   V
CGGGTGCTGCAGGGGGTCCTGCGGCCCTGCCGCCCTCAGGTGGTGTGCAACTACCGCGATGTGCGCTTCGAGTCCATCCGGCTCCCTGGCTGCCCGCGGGCGTGAACCCGTG-
GCCCACGACGACGTCCCCCAGGACGCCGGGACGGCGGAGTCCACCACACGTTGATGGCGCTACACGCGAAGCTCAGTAGGCCGAGGGACCGACGGGCGCCGCACTTGGGCAC-
              cctnagg(MstII)

V   S   Y   A   V   A   L   S   C   Q   C   A   L   C   R   R   S   T   T   D   C   G   G   P   K   D   H   P   L   T   C   D   D   P   R   F   Q
GTCTCCTACGCCGTGGCTCTCAGCTGTCAATGTGCACTCTGCCGCCGCAGCACCACTGACTGCGGGGGTCCAAGGACCACACCCCTTGACCTGTGATGACCCCGCTTCCAG-
CAGAGGATGCGGCACCGACAGTGACAGTTACACGTGAGACGGCGGCGTCGTGGTGACTGAGACGCCCCCAGGGTTCCTGGGAACTGGAACTGAGACACTACTGGGGGCGAAGGTC-
```

FIG. 5A

```
D  S  S  S  K  A  P  P  P  S  L  P  S  P  S  R  L  P  G  P  S  D  T  P  I  L  P  Q  G  S  G  S  G  S
GACTCCTCTTCCTCAAAGGCCCCTCCCCCAGCCTTCCAAGCCCATCCGACTCCCGGACACCCAGATCCTCCCCCAAGGATCCGGTAGCGGATCTGGTAGC-
CTGAGGAGAAGGAGTTTCCGGGGAGGGGGTCGGAAGGTTCGGTAGGGCCTGAGGGCCGGGAGCCTGTGGGTAGGAGGGGTTCCTAGGCCATCGCCTAGACCATCG-
                                                                                            agc
                                                    gggccc(ApaI)        ggatcc(BamHI)

A  P  D  V  Q  D  C  P  E  C  T  L  Q  E  N  P  F  F  S  Q  P  G  A  P  I  L  Q  C  M  G  C  C  F  S  R  A  Y
GCTCCTGATGTGCAGGATTGCCCAGAATGCACGCTACAGGAAAACCCATTCTTCTCCCAGCCGGGTGCCCCAATACTTCAGTGCATGGGCTGCTGCTTCTCTAGAGCATAT-
CGAGGACTACACGTCCTAACGGGTCTTACGTGCGATTGTCCTTTTGGGTAAGAAGAGGGTCGGCCCACGGGGTTATGAAGTCACGTACCCGACGACGAAGAGATCTCGTATA-
gct(Eco47III)

P  T  P  L  R  S  K  K  T  M  L  V  Q  K  N  V  T  S  E  S  T  C  C  V  A  K  S  Y  N  R  V  T  V  M  G  G  F
CCCACTCCACTAAGGTCCAAGAAGACGATGTTGGTCCAAAAGAACGTCACCTCAGAGTCCACTTGCTGTGTAGCTAAATCATATAACAGGGTCACAGTAATGGGGGTTTC-
GGGTGAGGTGATTCCAGGTTCTTCTGCTACAACCAGGTTTTCTTGCAGTCGAGTCTCAGGTGAACGACACATGATTTAGTATATTGTCCCAGTGTCATTACCCCCAAAG-

K  V  E  N  H  T  A  C  H  C  S  T  C  Y  Y  H  K  S  *
AAAGTGGAGAACCACACGGGCGTGCCACTGCCAGTACTTGTTATTATCACAAATCTTAAGGTACC-3'
TTTCACCTCTTGGTGTGCCCGCACGGTGACGTCATGAACATAATAGTGTTTAGAATTCCATGCCTAGGTAGAGTTCGATTAGGCCT-5'
                                                                    (KpnI)ggtaccggatcc(BglII)
```

*FIG. 5B*

Coding Sequence for Single Chain Gonadotropin Analog #2 and Primers (underlined)

```
          M  E  M  F  Q  G  L  L  L  L  L  L  S  M  G  G  T  W  A  S  K  E  P  L
5'-ATGAAATCGACGGAATCAGACTCGAGCCAAGGATGGAGATGTTCCAGGGGCTGCTGTTGCTGCTGTGCTGAGCATGGGCGGGACATGGGCATCCAAGGAGCCGCTT-
       3'-GGTTCCTACCTCTACAAGGTCCCCGACGACGACACGACTCGTACCCGCCCTGTACCCGTAGGTTCCTCGGCGAA-
         ctcgag(XhoI)

R  P  R  C  R  P  I  N  A  T  L  A  V  E  K  E  G  C  P  V  C  I  T  V  N  T  T  I  C  A  G  Y  C  P  T  M  T
CGGCCACGGTGCCGCCGCCCCATCAATGCCACCCTGGCTGTGGAGAAGGAGGGCTGCCCCGTGTGCATCACCGTCAACACCACCATCTGCGCCTACTGCCCCACCATGACC
GCCGGTGCCACGGCGGCGGGGTAGTTACGGTGGGACCGACACCTCTCCCCGACGGGGCACACGTAGTGGCAGTTGTGGTGGTAGACACGGCCGATGACGGGTGGTACTGG

R  V  L  Q  G  V  L  R  A  L  P  Q  V  V  C  N  Y  R  D  V  R  F  E  S  I  R  L  P  G  C  P  R  G  V  N  P  V
CGGGTGCTGCAGGGGGTCCTGCGGGCCCTGCCCCAGGTGGTGTGCAACTACCGCGATGTGCGCTTCGAGTCCATCCGGCTCCCTGGCTGCCCGGCGTGAACCCCGTG-
GCCCACGAGTCCCCCAGGACGCCCGGGACGGGGTCCACCACACGTTGATGGCGCTACACGCGAAGCTCAGGTAGGCCGAGGGACCGACGGGCGCGCACTTGGGCAC-
                                                                                   cctnagg(MstII)

V  S  Y  A  V  A  L  S  C  Q  C  A  L  C  R  R  S  T  T  D  C  G  G  P  K  D  H  P  L  T  C  D  D  P  R  G  S
GTCTCCTACGCCGTGGCTCTCAGCTGTCAATGCGCTCTGTGCCGCCGCAGCACCACTGACTGCGGGGTCCCAAGGACCACCCCTTGACTGTGATGACCCGCGGGGATCC-
CAGAGGATGCGGCACCGACAGTCGACAGTTACACGCGAGACACGGCGGCGTCGTGGTGACTGACGCCCCAGGGTTCCTGGTGGTGGGAACTGACACTACTGGGCGCCCTAGG-
                                                                                         (SstII)  ccgcggggatcc(BamHI)
```

Coding Sequence for Single Chain Gonadotropin Analog #3 and Primers (underlined)

```
          M   E   M   L   Q   G   L   L   L   L   L   L   S   M   G   G   A   W   A   S   R   E   P   L
5'-ATGAAATCGACGAATCAGACTCGAGCCAAGGAATGGAGATGCTCCAGGGGCTGCTGCTGCTGTTGCTGCTGAGCATGGGCGGGGCATGGGCATCCAGGAGCCGCTT-
  3'-GGTTCCTTACCTCTACGAGGTCCCCGACGACGACAACGACGACTCGTACCCGCCCGTAGGTCCCTCGGCGAA-
           ctcgag(XhoI)

R   P   W   C   H   P   I   N   A   I   L   A   V   E   K   E   G   C   P   V   C   I   T   V   N   T   T   I   C   A   G   Y   C   P   T   M   M
CGGCCATGGTGCTGCCACCCCATCAATGCCATCCTGGCTGTGGAGAAGGAGGGCTGCCCCGTCTGCATCACCGTCAACACCACCATCTGTGCCGGCTACTGCCCCACCATGATG-
GCCGGTACCACGGTGGGGTAGTTACGGTAGGACCGACACCTCTTCCTCCGACGGGCACGTAGTGGCAGTTGTGGTAGACACGGCCGATGACGGGTGGTACTAC-

R   V   L   Q   A   V   L   P   P   L   P   Q   V   V   C   T   Y   R   D   V   R   F   E   S   I   R   L   P   G   C   P   R   G   V   D   P   P   V
CGGGTGCTCTGCAGGGCGGTCCTGCCGCCCTGCCCCAGGTGGTGTGCACCTACCGTGATGTGCGCTTCGAGTCCATCCGGCTCCCTGGCTGCCCGCGTGGCGTGGACCCCGTG-
GCCCACGAGAGTCGTCCAGGACGGCGGGACGGGGTCCACCACACACGTGGATGGCACTACACGCGAAGCTCAGGTAGGCCGAGGGACCGACGGGCGCACCGCACCTGGGCAC-
                                               cctnagg(MstII)

V   S   F   P   V   A   L   S   C   R   C   G   P   C   R   R   S   T   S   D   C   G   G   P   K   D   H   P   L   T   C   D   H   P   Q   G   S
GTCTCCTTCCTTCCCTGTGGCTCTCAGCTGTCGCTGTCTGCCGGCCTGCCGGCGCAGCACCCTCTGACTGTGGGGGTCCCAAAGACCACCCCTTGACCTGTGACCACCCCCAAGGATCC-
CAGAGGAAGGGACACCGAGAGTCGACAGCAGTCGACAGCGACGGCGGCCGGACGGCCGTCGTGGGAGACTGACACCCCCAGGGTTTCTGTGGGAACTGGACACTGGTGGGGTTCCTAGG-
                                                                                                     (BamHI)ggatcc
```

FIG. 7A

```
G  S  G  G  S  A  P  D  V  Q  D  C  P  E  C  T  L  Q  E  N  P  F  F  S  Q  P  G  A  P  I  L  Q  C  M  G  C
GGTAGCGGAGATCTGGTAGCGCTCCTGATGTGCAGGATTGCCCAGAATGCACGCTACAGGAAAACCCATTCTTCTTCCCCAGCCGGGTGCCCCAATACTTCAGTGCATGGGCTGC-
CCATCGCCTAGAGACTCGCGAGGACTACACGTCCTAAGCGGGTCTTACGTGCGATGCGTCCTTTTGGGTAAGAAGAGGGTCGGCCCACGGGGTTATGAAGTCACGTACCGACG-
                 agcgct(Eco47III)

C  F  S  R  A  Y  P  T  P  L  R  S  K  K  T  M  L  V  Q  K  N  V  T  S  E  S  T  C  C  V  A  K  S  Y  N  R  V
TGCTTCTCTAGAGCATATCCCACTCCACTAAGGTCCAAGAAGACGATGTTGGTCCAAAAGAACGTCACCTCAGAGTCCACTTGCTGTGTAGCTAAATCATATAACAGGGTC-
ACGAAGAGATCTCGTATAGGGTGAGGTGATTCCAGGTTCTTCTGCTACAAGGTTTCTTGCAGTGGAGTCTCAGGTGAACGACACATCGATTTAGTATATTGTCCCAG-

T  V  M  G  G  F  K  V  E  N  H  T  A  C  H  C  S  T  C  Y  Y  H  K  S  *
ACAGTAATGGGGGGTTTCAAAGTGGAGAACCACACGGCGTGCCACTGCAGTACTTGTTATTATCACAAATCTTAAGGTACC-3'
TGTCATTACCCCCCAAAGTTTCACCTCTTGGTGTGCCGCACGGTGACGTCATGAACAATAATAGTGTTTAGAATTCCATGG-5'
                                                              ggtacc(KpnI)
```

FIG. 7B

Coding Sequence for Single Chain Gonadotropin Analog 4 and Primers (underlined)

```
                                   M  K  T  L  Q  F  F  F  L  F  C  C  W  K  A  I  C  C  N  S  C  E  L  T  N
5'-ATGAAAATCGACGGAATCAGACTCGAGCCAAGGATGAAGACACTCCAGTTTTTCTTCCTTTTCTGTTGCTGGAAAGCAATCTGCTGCAATAGCTGTGAGCTGACCAAC-
                           3'-GGTTCCTACTTCTGTGAGGTCAAAAAGAAGGAAAAGACAACGACCTTTCGTTAGACGACGTTATCGACACTCGACTGGTTG-
                         ctcgag(XhoI)

I  T  I  A  I  E  K  E  E  C  R  F  C  I  S  I  N  T  T  W  C  A  G  Y  C  Y  T  R  D  L  V  Y  K  D  P  A  R
ATCACCATTGCAATAGAGAAAGAAGAATGTCGTTTCTGCATAAGCATCAACACCACTTGGTGTGCTGGCTACTGCTACACCAGGGATCTGGTGTATAAGGACCCAGCCAGG-
TAGTGGTAACGTTATCTCTTTCTTCTTACAGCAAAGACGTAGGCGTAGTTGTGGTGAACCACACGACCGATGACGATGTGGTCCCTAGACCACATATTCCTGGGTCGGTCC-

P  K  I  Q  K  T  C  T  F  K  E  L  V  Y  E  T  V  R  V  P  G  C  A  H  H  A  D  S  L  Y  T  Y  P  V  A  T  Q
CCCAAAATCCAGAAAACATGTACCTTCAAGGAACTGGTATATGAAACAGTGAGAGTGCCCGGCTGTGCTCACCATGCAGATTCCTTGTATACATACCCAGTGGCCACCCAG-
GGGTTTTAGGTCTTTTGTACATGGAAGTTCCTTGACCATATACTTTGTCACTCTCACGGGCCGACACGAGTGGTACGTCTAAGGAACATATGTATGGGTCACCGGTGGGTC-
                                                                                                   tggcca(BalI)

C  H  C  G  K  C  D  S  D  S  T  D  C  T  V  R  G  L  G  P  S  Y  C  S  F  G  E  M  K  E  G  S  GS  G  S  G
TGTCACTGTGGCAAGTGTGACAGCGACAGCACTGATTGTACTGTGCGAGGCCTGGGGCCCAGCTACTGCTCCTTTGGTGAAATGAAAGAAGGATCCGGTAGCGGATCTGGT-
ACAGTGACACCGTTCACACTGTCGCTGTCGTGACTAACATGACACGCTCCGGACCCCGGGTCGATGACGAGGAAACCACTTTACTTTCTTCCTAGGCCATCGCCTAGACCA-
                                                   gggccc(ApaI)                         ggatcc(BamHI)
```

FIG. 8A

```
S  A  P  D  V  Q  D  C  P  E  C  T  L  Q  E  N  P  F  F  S  Q  P  G  A  P  I  L  Q  C  M  G  C  C  F  S  R  A
AGCGCTCCTGATGTGCAGGATGCAGAATGCCCAGAATGCACGCTACAGGAAAACCCATTCTTCTCCCAGCCAGGGTGCCCAATACTTCAGTGCATGGGCTGCTGCTTCTAGAGCA-
TCGCGAGGACTACACGTCCTAACGGGTCTTACGTGCGATGTCCTTTTGGGTAAGAGAGGGTCGGCCCACGGGTTATGAAGTCACGTACCGACGACGAAGAGATCTCGT-
  agcgct(Eco47III)

Y  P  T  P  L  R  S  K  K  T  M  L  V  Q  K  N  V  T  S  E  S  T  C  C  V  A  K  S  Y  N  R  V  T  V  M  G  G
TATCCCACTCCACTAAGGTCCAAGAAGACGATGTTGGTCCAAAAGAACGTCACCTCACTTGCTGTGTAGCTAAATCATATAACAGGTCACAGTAATGGGGGT-
ATAGGGTGAGGTGATTCCAGGTTCTTCTGCTACAACCAGGTTTTCTTGCAGTGGAGTCTCAGTGAGTCTCAGTGAACGACACATCGATTTAGTATATTGTCCCAGTGTCATTACCCCA-

F  K  V  E  N  H  T  A  C  H  C  S  T  C  Y  Y  H  K  S  *
TTCAAAGTGGAGAACCACACGGGCGTGCCACTGCCAGTACTTGTTATTATCACAAATCTTAAGGTACC-3'
AAGTTTCACCTCTTGGTGTGCCCGCACGGTGACGTCATGAACAATAATAGTGTTTAGAATTCCATGG-5'
                                                    ggtacc(KpnI)
```

FIG. 8B

Coding Sequence for Single Chain Gonadotropin Analog #5 and Primers (underlined)

```
                     M   E   M   F   Q   G   L   L   L   L   L   L   S   M   G   G   T   W   A   S   K   E   P   L
5'-ATGAAATCGACGGAATCAGACTCGAGCCAAGGATGGAGATGTTCCAGGGGCTGCTGTTGCTGCTGTTGCTGTCTATGGGCGGACATGGCATCCAAGGAGCCGCTT-
  3'-GGTTCCTACCTCTACAAGGTCCCCGACGACAACGACGACTCGTACCCGCCTGTACCCGTAGGTTCCTCGGCGAA-
                                            ctcgag(XhoI)
```

```
    R   P   R   C   R   P   I   N   A   T   L   A   V   E   K   E   G   C   P   V   C   I   T   V   N   T   T   I   C   A   G   Y   C   P   T   M   T
CGGCCACGGTGCGCCGCCCATCAATGCCACCCTGGCTGTGGAGAAGGAGGGCTGCCCCGTGTGCATCACCGTCAACACCACCATCTGCGCCGGCTACTGCCCCACCATGACC-
```

```
    R   V   L   Q   G   V   L   R   A   L   P   Q   V   V   C   N   Y   R   D   V   R   F   E   S   I   R   L   P   G   C   P   R   G   V   N   P   V
CGGGTGCTGCAGGGGGTCCTGCGGGCCCTGCCCCAGGTGGTGTGCAACTACCGGGATGTGCGCTTCGAGTCCATCCGGCTCCCTGGCTGCCCGCGGGGTGAACCCCGTG-
                                            cctnagg(MstII)
```

```
    V   S   Y   A   V   A   L   S   C   Q   C   A   L   C   D   S   D   S   T   D   C   T   V   R   G   L   G   P   S   Y   C   S   F   G   E   M   K
GTCTCCTACGCGGTGGCTCTCAGCTGTCAATGTGCACTCTGCGACAGCGACAGCACTGATTGTACTGTGCGAGGCCTGGGGCCCAGCTACTGCTCCTTTGGTGAAATGAAA-
CAGAGGATGCGCACCGACAGTCGACAGTTACACGTGAGACGCTGTCGTTGACTAACATGACACGCTCCGGACCCCGGGTCGATGACGAGGAAACCACTTTACTTT-
                                                                                                            gggccc(ApaI)
```

FIG. 9A

```
E  G  S  G  S  G  S  G  S  A  P  D  V  Q  D  C  P  E  C  T  L  Q  E  N  P  F  F  S  Q  P  G  A  P  I  L  Q  C
GAAGGATCCGGTAGCGGATCCGGTAGCGGTAGCGCTCCTGATGTGCAGGATTGCCAGAATGCACGCTACAGGAAAACCCATTCTTCTCCCAGCCGGGTGCCCCAATACTTCAGTGC
CTTCCTAGGCCATCGCCTAGACCCATCGCCGAGACTACACGTCCTAACGGGTCTTACGTGCGATGCTCCTTTTGGGTAAGAAGAGGGTCGGCCACGGGGTTATGAAGTCACG-
     ggatcc(BamHI)               agcgct(Eco47III)

M  G  C  C  F  S  R  A  Y  P  T  P  L  R  S  K  K  T  M  L  V  Q  K  N  V  T  S  E  S  T  C  C  V  A  K  S  Y
ATGGGCTGCTGCTTCTCTAGAGCATATCCCACTCCACTTGGTCCAAAAGAACGATGTTGGTCCAGAGTCCACTTGCTGTGTAGCTAAATCATAT-
TACCCGACGACGAAGAGATCTCGTATAGGGTGAGGTGATTCCAGGTTTTCTTGCTACAACCAGGTCTCAGGTGACGACACATCGATTTAGTATA-

N  R  V  T  V  M  G  G  F  K  V  E  N  H  T  A  C  H  C  S  T  C  Y  Y  H  K  S  *
AACAGGGTCACAGTAATGGGGGGTTTCAAAGTGGAGAACCACGGCTGCCACTGCAGTACTTGTTATTATCACAAATCTTAAGGTACC-3'
TTGTCCCAGTGTCATTACCCCCCAAAGTTTCACCTCTTGGTGCCGCACGGTGACGTCATGAACAATAATAGTGTTTAGAATTCCATGG-5'
                                                                                ggtacc(KpnI)
```

*FIG. 9B*

Coding Sequence for Single Chain Gonadotropin Analog #6 and Primers (underlined)

```
              M  E  M  F  Q  G  L  L  L  L  L  L  L  S  M  G  G  T  W  A  S  K  E  P  L
5'-ATGAAATCGACGAATCAGACTGAGCCAAGGATGGAGATGTTCCAGGGGCTGCTGTTGCTGCTGCTGAGCATGGGCGGGACATGGGCGAGTCCAAGGAGCCGCTT-
      3'-GGTTCCTACCTCTACAAGGTCCCCGACGACGACGACGACGACTCGTACCCGCCCTGTACCCGTAGTTCCTCGGCGAA
         ctcgag(XhoI)

R  P  R  C  R  P  I  N  A  T  L  A  V  E  K  E  G  C  P  V  C  I  T  V  N  T  T  I  C  A  G  Y  C  P  T  M  T
CGGCCACGGTGCCGCTGCCGCCCCATCAATGCCACCCTGGCTGTGGAGAAGGAGGGCTGCCCCGTGTGCATCACCGTCAACACCACCATCTGTGCCGGCTACTGCCCCACCATGACC
GCCGGTGCCACGGCGACGGCGGGGTAGTTACGGTGGGACCGACGACCTCTTCCTCCCGACGGGGCACACGTAGTGGCAGTTGTGGTAGACACGGCCGATGACGGGGTGGATCTGG

R  V  L  Q  G  V  L  R  A  L  P  Q  V  V  C  N  Y  R  D  V  R  F  E  S  I  R  L  P  G  C  P  R  G  V  N  P  V
CGCGTGCTGCAGGGGGTCCTGCGCGCCCTGCCGCAGGTGGTGTGCAACTACCGCGATGTGCGCTTCGAGTCCATCCGGCTCCCTGGCTGCCCGCGGGGTGAACCCCGTG-
GCGCACGACGTCCCCAGGACGCCCGGGACGGCGCGGGGAGAGCGGGAGTCCCACCACAGGTTGATGGGCGCTACACGCGAAGCTCAGGTAGGCCGAGGGACCGACGGGCGCCGCACTTGGGCAC
cctnagg(MstII)

V  S  Y  A  V  A  L  S  C  Q  C  A  L  C  R  R  S  T  T  D  C  T  V  R  G  L  G  P  S  Y  C  S  F  G  E  M  K
GTCTCCTACGCCGTGGCCTCTCAGCTGTCAATGTGCACTCTGCCGCCGCAGCACCACTGACTGCACTGTGCGGAGGCCTGGGCCCCAGCTACTGCTCCTTTGGTGAAATGAAA-
CAGAGGATGCGGCACCGAGACGTCGACAGTTACACGTGAGACGTGACAGTCGTGTGACAGCGGCGTCGTCGTGACTGACACGCGCTCCGGACCCGGGTCGATGACGAGGAAACCACTTTACTTT-
                                                                                          gggccc(ApaI)
```

FIG. 10A

E G S G S G S A P D V Q D C P E C T L Q E N P F F S Q P G A P I L Q C
GAAGGATCCGGTAGCGGATCTGGTAGCGCTCCTGATGTGCAGGATTGCCAGAATGCACGCTACAGGAGAAAACCCATTCTTCTCCCAGCCGGGTGCCCCAATACTTCAGTGC-
CTTCCTAGGCCATCGCCTAGACTACGCCGAGGACTACACGTCCTAACGGGTCTTACGTGCGATGTCCTTTTGGGTAAGAAGAGGGTCGGCCACGGGGTTATGAAGTCACG-
   ggatcc(BamHI)         agcgct(Eco47III)

M G C C F S R A Y P T P L R S K K T M L V Q K N V T S E S T C C V A K S Y
ATGGGCTGCTGCTTCTCTAGAGCATATCCCACTCCACTAAGGTCCAAGAAGACGATGTTGGTCCAAAAAGAACGTCACCTCCGAGTCCACTTGCTGTGTAGCTAAATCATAT-
TACCCGACGACGAAGAGATCGTATAGGGTGAGGTGATTCCAGGTTCTTCTGCTACAACCAGGTTTTCTTGCAGTGGAGTCTCAGGTGAACGACACATGATTTAGTATA-

N R V T V M G G F K V E N H T A C H C S T C Y Y H K S *
AACAGGGTCACAGTGATGGGGGTTTCAAAGTGGAGAACCACACGGCGTGCCACTGCCACTGACTACTTGTTATTATCACAAATCTTAAGGTACC-3'
TTGTCCCAGTGTCATTACCCCCAAAGTTTCACCTCTTGTTGGTGTGCCGCACGGTGACGTCATGAACAATAATAGTGTTTAGAATTCCATGG-5'
                                                                            ggtacc(KpnI)

FIG. 10B

Coding Sequence for Single Chain Gonadotropin Analog#7 and Primers (underlined)

M E M F Q G L L L L L L S M G G T W A S K E P L
5'-ATGAAATCGACGGAATCAGACTCGAGCCAAGATGGAGATGTTCCAGGGGCTGCTGCTGTTGCTGCTGTCGATGGGCGGACATGGGCATCCAAGGAGCCGCTT-
3'-GGTTCCTACCTCTACAAGGTCCCCGACGACGACAACGACGACTCGTACCCGCCCTGTACCCGTAGGTTCCTCGGCGAA-
    ctcgag(XhoI)

R P R C R P I N A T L A V E K E G C P V C I T V N T T I C A G Y C P T M T
CGGCCACGGTGCGCCCGCCCATCAATGCCACCCTGGCTGTGGAGAAGGAGGGCTGCCCCGTGTGCATCACCGTCAACACCACCATCTGTGCCGGCTACTGCCCCACCATGACC-
GCCGGTGCCACGCGGGCGGGTAGTTACGGTGGACCGACACACCTCTTCCTCCCGACGGGGCACACTAGTGGCAGTTGTGGTGGTAGACACGGCCGATGACGGGGTGGATCTGG-

R V L Q G V L R A L P Q V V C N Y R D V R F E E S I R L P G C P R G V N P V
CGGTGCTGCAGGGGGTCCTGCGGGCCCTGCCCTCAGGTGGTGTGCAACTACCGCGATGTGCGCTTCGAGTCCATCCGGCTCCCCGGCTGCCCGCGGGGTGAACCCCGTG-
GCGCACGACGTCCCCCAGGACGCGCCGGGACGGGAGTCCACCACACGTTGATGGCGCTACACGCGAAGCTCAGGTAGGCCGAGGACCGACGGGCGCCCACTTGGGGCAC-
                                       cctnagg(MstII)

V S Y A V A L S C Q C A L C R R S T T D C T V R G L G P S Y C S F G E E G S
GTCTCCTACGCCGTGGCTCTCAGCTGCCAGTGTGCACTGTGCCGCCGCAGCACTGACTGCACTGTGCGAGGGCCTGGGGCCCAGCTACTGCTCCTTTGGTGAAGGATCC-
CAGAGGATGCGGCACCGACAGTCGACAGTTACACGTGACACGTGACACGCTCTCCGGACCCCGGGTCGATGACGTCGATGACGAGGAAACCACTTCCTAGG-
                                                       gggccc(ApaI)                                       ggatcc(BamHI)

*FIG. 11A*

G S G S G S A P D V Q D C P E C T L Q E N P F F S Q P G A P I L Q C M G C
GGTAGCGGATCTGGTAGCGCTCCTGATGTGCAGGATTGCCCAGAATGCACGCTACAGGAAAACCATTCTTCTCCCAGCCGGGTGCCCAATACTTCAGTGCATGGGCTGC-
CCATCGCCTAGACCATCGCGAGGACTACACGTCCTAACGGGTCTTACGTGCGATGTCCTTTGGGTAAGAAGAGGGTCGCCCACGGGGTATGAAGTCACGTACCCGACG-
   agcgct(Eco47III)

C F S R A Y P T P L R S K K T M L V Q K N V T S E S T C C V A K S Y N R V
TGCTTCTCTAGAGCATATCCCACTCCACTGCGAAGTCCAAGAAGACGATGTTGGTCCAAAAGAACGTCACCTGCTGTGTAGCTAAATCATATAACAGGGTC-
ACGAAGAGATCGTATAGGGTGAGGTGATTCCAGGTTCTTGCTACAACCAGTTTCTTGCAGTGGAGTCTCAGGTGAACGACACATCGATTTAGTATATTGTCCCAG-

T V M G G F K V E N H T A C H C S T C Y Y H K S *
ACAGTAATGGGGGGTTTCAAAGTGGAGAACCACACGGCGTGCCACTGCAGTACTTGTTATTATCACAAATCTTAAGGTACC-3'
TGTCATTACCCCCCAAAGTTTCACCTCTTGGTGCCGCACGGTGACGTCATGAACAATAATAGTGTTTAGAATTCCATGG-5'
                                                                ggtacc(KpnI)

FIG. 11B

Coding Sequence for Single Chain Gonadotropin Analog #8 and Primers (underlined)

```
                M   E   M   F   Q   G   L   L   L   L   L   L   S   M   G   G   T   W   A   S   K   E   P   L
5'- ATGAAAATCGACGGAATCAGACTCGAGCCAAGGATGGAGATGTTCCAGGGGCTGCTGCTGTTGCTGCTGAGCATGGGGGGACATGGGCATCCAAGGAGCCGCTT-
3'- GGTTCCTACCTCTACAAGGTCCCCGACGACGACAACGACGACTCGTACCCGCCCTGTACCCGTAGTTCCTCGGCGAA-
    ctcgag(XhoI)

R   P   R   C   R   P   I   N   A   T   L   A   V   E   K   E   G   C   P   V   C   I   T   V   N   T   T   I   C   A   G   Y   C   P   T   M   T
CGGCCACGGTGCCGCCCCATCAATGCCACCCTGGCTGTGGAGAAGGAGGGGCTGCCCGTGTGCATCACCGTCAACACCACCATCTGTGCCGGCTACTGCCCCACCATGACC-
GCCGGTGCCACGGCGGGGTAGTTACGGTGGGACCGACACCTCTTCCTCCCGACGGGCACGTAGTGGCAGTTGTGGTGGTAGTAGACACGGCCGATGACGGGGTGGATCTGG-

R   V   L   Q   G   V   L   R   A   L   P   Q   V   V   C   N   Y   R   D   V   R   F   E   S   I   R   L   P   G   C   P   R   G   V   N   P   V
CGCGTGCTGCAGGGGGTCCTGCGCGCCCTGCCCCAGGTGGTGTGCAACTACCGCGATGTGCGCTTCGAGTCCATCCGGCTCCCTGGCTGCCCCCGGGGCGTGAACCCCGTG-
GCGCACGACGTCCCCAGGACGGCCCGGGACGGGGTCCACCACACGTTGATGGCGCTACACGCGAAGCTCAGGTAGGCCGAGGGACCGACGGGGCGCCCACTTGGGGCAC-
                                                                                  cctnagg(MstII)

V   S   Y   A   V   A   L   S   C   Q   C   A   L   C   R   R   S   T   T   D   C   T   V   R   G   L   G   P   S   Y   C   D   D   P   R   G   S
GTCTCCTACGCCGTGGCTCTCAGCTGTCAATGTGCACTCTGCCGCCGCAGCACCACTGACTGCACTGTGCGAGGCCTGGGCCCAGCTACTGCGATGACCCGCGGGGATCC-
CAGAGGATGCGGCACCGACGAGTCGACAGTTACACGTGAGAGTCGACACGTGGTGACTGACTGACGTGACACGCTCCGGACCCGGTCGATGACGTACTGGGCGCCCTAGG-
                                                                          gggccc(ApaI)  (SstII) ccgcggggatcc(BamHI)
```

FIG. 12A

```
G  S  G  S  G  S  A  P  D  V  Q  D  C  P  E  C  T  L  Q  E  N  P  F  F  S  Q  P  G  A  P  I  L  Q  C  M  G  C
GGTAGCGGATCTGGTAGCGCTCCTGATGTGCAGGATTGCCCAGAATGCACGCTACAGGAAAAACCCATTCTTCTCCCAGCCGGGTGCCCAATACTTCAGTGCATGGGCTGC
CCATCGCCTAGACCATCGCGAGGACTACACGTCCTAACGGGTCTTACGTGCGATGTCCTTTTGGGTAAGAAGAGGGTCGGCCCACGGGTTATGAAGTCACGTACCCGACG
                              agcgct(Eco47III)

C  F  S  R  A  Y  P  T  P  L  R  S  K  K  T  M  L  V  Q  K  N  V  T  S  E  S  T  C  C  V  A  K  S  Y  N  R  V
TGCTTCTCTAGAGACATATCCCACTCCACTAAGTCCAAAGAAGACGATGTTGGTCCAAAAGAAGAACGTCACCTCAGAGTCCACTTGCTGTGTAGCTAAATCATATAACAGGGTC
ACGAAGAGATCTCGTATAGGGTGAGGTGATTCAGTTCTTGCTACAACCAGTTTCTTGCTACGTCTCCAGTGGAGTCTCAGTGAACGACACATCGATTAGTATATTGTCCCAG

T  V  M  G  G  F  K  V  E  N  H  T  A  C  H  C  S  T  C  Y  Y  H  K  S  *
ACAGTAATGGGGGGTTTCAAAGTGGAGAACCACACGGCGTGCCACTGCAGTACTTGTTATTACACAAATCTTAAGGTACC-3'
TGTCATTACCCCCCAAAGTTTCACCCTCTTGGTGTGCCGCACGGTGACGTCATGAACAATAATAGTGTTTAGAATTCCATGG-5'
                                                                    ggtacc(KpnI)
```

FIG. 12B

Coding Sequence for Single Chain Gonadotropin Analog 9 and Cassette (underlined)

```
                        M  K  T  L  Q  F  F  F  L  F  C  C   W  K  A  I  C  C  N  S  C  E  L  T  N
5'-ATGAAATCGACGGAATCAGACTCGAGCCAAGGATGAAGACACTCCAGTTTTTCTTCCTTTTCTGTTGCTGGAAAGCAATCTGCTGCAATAGCTGTGAGCTGACCAAC-
         3'-GGTTCCTACTTCTGTGAGGTCAAAAAGAAGGAAAAGACAACGACCTTTCGTTAGACGACGTTATCGACACTCGACTGGTTG-
              ctcgag(XhoI)

I  T  I  A  I  E  K  E  E  C  R  F  C  I  S  I  N  T  T  W  C  A  G  Y  C  Y  T  R  D  L  V  Y  K  D  P  P  A  R
ATCACCATTGCAATAGAGAAAGAAGAATGTCGTTCTGCATAAGCATCAACACCACTTGGTGTGCTGGCTACTGCTACACCAGGGATCTGGTGTATAAGGACCCAGCCAGG
TAGTGGTAACGTTATCTCTTTCTTCTTACAGCAAGACGTAGTTCGTAGTTGTGGTGAACCACACGACCGATGACGATGTGGTCCCTAGACACATATTCCTGGGTCGGTCC

P  K  I  Q  K  T  C  T  F  K  E  L  V  Y  E  T  V  R  V  P  G  C  A  H  H  A  D  S  L  Y  T  Y  P  V  A  T  Q
CCCAAAATCCAGAAAACATGTACCTTCAAGGAACTGGTATATGAAACAGTGAGAGTGCCCGGCTGTGCTCACCATGCAGATTCCTTGTATACATACCCAGTGGCCACCAG-
GGGTTTTAGGTCTTTTGTACATGGAAGTTCCTTGACCATATACTTTGTCACTCTCACGGGCCGACACGAGTGGTACGTCTAAGGAACATATGTATGGGTCACCGGTGGTC
                                                                                                tggcca(BalI)

C  H  C  G  K  C  D  S  D  S  T  D  C  T  V  R  G  L  G  P  S  Y  C  S  F  G  E  G  S  G  S  G  G  S  A  P
TGTCACTGTGGCAAGTGTGACAGCGACAGCACTGATTGTACTGTGCGAGGCCTGGGGCCCAGCTACTGCTCCTTCTTTGGTGAAGGATCCGGTAGCGGATCTGGTAGCGCTCCT-
ACAGTGACACCGTTCACACTGTCGCTGTCGTGACTAACATGACATGACACGCTCCGGACCCCGGGTCGATGACGAGGAAACACTTCCTAGGCCATCGCCTAGACGAGGA
        gggccc(ApaI)          (BamHI)ggatcc                                                    agcgct(Eco47III)
```

FIG. 13A

```
D  V  Q  D  C  P  E  C  T  L  Q  E  N  P  F  F  S  Q  P  G  A  P  I  L  Q  C  M  G  C  C  F  S  R  A  Y  P  T
GATGTGCAGGATTGCCCAGAATGCCACGCTACAGGAAAACCCATTCTTCTCCCAGCCAGGTGCCCCAATACTTCAGTGCATGGGCTGCTGCTTCTCTAGAGCATATCCCACT-
CTACACGTCCTAACGGGTCGGATGTCCGATGTCCTTTGGGTAAGAAGAGGGTCGGCCCACGGGGTTATGAAGTCACGTACCCGACGACGAAGAGATCTCGTATAGGGTGA-

P  L  R  S  K  K  T  M  L  V  Q  K  N  V  T  S  E  S  T  C  C  V  A  K  S  Y  N  R  V  T  V  M  G  G  F  K  V
CCACTAAGGTCCAAGAAGACGATGTTGGTCCAAAAGAACGTCACCTCAGAGTCCACTTGCTGTGTAGCTAAATCATATAACAGGTCACAGTAATGGGGGTTTCAAAGTG-
GGTGATTCCAGGTTCTTCTGCTACAACCAGGTTTCTTGCAGTGGAGTCTCAGGTGAACGACACATCGATTTAGTATATTGTCCCAGTGTCATTACCCCCAAAGTTTCAC-

E  N  H  T  A  C  H  C  S  T  C  Y  Y  H  K  S  *
GAGAACCACACGGCGTGCCACTGCAGTACTTGTTATTATCACAAATCTTAAGGTACC-3'
CTCTTGGTGTGCCGCACGGTGACGTCATGAACAATAATAGTGTTTAGAATTCCATGG-5'
                                              ggtacc(KpnI)
```

FIG. 13B

Coding Sequence for Single Chain Gonadotropin Analog 10 and Cassette (underlined)

```
              M  K  T  L  Q  F  F  F  L  F  C  C  W  K  A  I  C  C  N  S  C  E  L  T  N
5'-ATGAAATCGACGGAATCAGACTCGAGCCAAGATGAAGACACTCCAGTTTTTCTTCTGTTGCTGGAAAGCAATCTGTGAGCTGACCAAC-
3'-GGTTCCTACTTCTGTGAGTCAAAAAGAAGGAAGACAACGACCTTTCGTTAGACACTCGACTGGTTG-
    ctcgag(XhoI)

I  T  I  A  I  E  K  E  E  C  R  F  C  I  S  I  N  T  T  W  C  A  G  Y  C  Y  T  R  D  L  V  Y  K  D  P  A  R
ATCACCATTGCAATAGAGAAAGAAGAATGTCGTTTCTGCATAAGCATCAACACCACTTGGTGTGCTACTGGCTACTGCTACACCAGGGATCTGGTGTATAAGGACCCAGCCAGG-
TAGTGGTAACGTTATCTCTTTCTTCTTACAGCAAAGACGTATTCGTAGTTGTGGTGAACCACACGATGACGATGTGGTCCCTAGACCACATATTCCTGGGTCGGTCC-

P  K  I  Q  K  T  C  T  F  K  E  L  V  Y  E  T  V  R  V  P  G  C  A  H  H  A  D  S  L  Y  T  Y  P  V  A  T  Q
CCCAAAAATCCAGAAAACATGTACCTTCAAGGAACTGGTATATGAAACAGTGAGAGTGCCCGGCTGTGCTCACCATGCAGATTCCTTGTATACATACCCAGTGGCCACCCAG-
GGGTTTTAGGTCTTTTGTACATGGAAGTTCCTTGACCATATACTTTGTCACTCTCACGGGCCGACACGAGTGGTAGTCTAAGGAACATATGTATGGGTCACCGGTGGTC-
                                                                                              tggcca(BalI)

C  H  C  G  K  C  D  S  D  S  T  D  C  T  V  R  G  L  G  P  S  Y  C  S  G  S  G  S  A  P  D  V  Q  D
TGTCACTGTGGCAAGTGTGACAGCGACAGCACTGATTGTACTGTGCGAGGCCTGGGACCCAGCTACTGCGGATCTGGTAGCCGGTAGCCTCCTGATGTGCAGGAT-
ACAGTGACACCGTTCACACTGTCGCTGTCGTGACTAACATGACACGCTCCGGACCCTGGGTCGATGACGCCTAGACCATCGGCGAGGACTACACGTCCTA-
                                                              gggccc(ApaI)      (BamHI)ggatcc    agcgct(Eco47III)
```

FIG. 14A

C P E C T L Q E N P F F S Q P G A P I L Q C M G C C F S R A Y P T P L R S
TGCCCAGAATGCACGCTACAGAGAAAACCCATTCTTCTCCCAGCCGGGTGCCCAATACTTCAGTGCATGGGCTGCTGCTTCTCTAGAGACATATCCCACTCCACTAAGGTCC-
ACGGGTCTTACGTGCGATGTCCTTTTGGGTAAGAGAGGGTCGGCCACGGGGTTATGAAGTCACGTACCCGACGAAGAGATCTCGTATAGGGTGAGTGATTCCAGG-

K K T M L V Q K N V T S E S T C C V A K S Y N R V T V M G G F K V E N H T
AAGAAGACGATGTTGGTCCAAAGAACGTCACCTCAGAGTCCACTTGCTGTGTAGCTAAATCATATAACAGGGTCACAGTAATGGGGGGTTTCAAAGTGGAGAACCACACG-
TTCTTCTGCTACAACCAGGTTTCTTGCAGTTCAGGTGAGTCTCAGGTGAACGACACATCGATTTAGTATATTGTCCAGTGTCATTACCCCCCAAAGTTTCACCTCTTGGTGTGC-

A C H C S T C Y Y H K S *
GCGTGCCACTGCAGTACTTGTTATTATCACAAATCTTAAGGTACC-3'
CGCACGGTGACGTCATGAACAATAATAGTGTTTAGAATTCCATGG-5' ggtacc(KpnI)

FIG. 14B

Preparation of an alpha-subunit coding region lacking oligosaccharide signal sequences

```
  C  G  S  G  S  G  S  A  P  D  V  Q  D  C  P  E  C  T  L  Q  E  N  P  F  F  S  Q  P  G  A  P  I  L  Q  C
TGCGGATCCGGTAGCGGATCTGGTAGCGCTCCTGATGTGCAGGATTGCCCAGAATGCACGCTACAGGAAAACCCATTCTCTCCAGCCGGGTGCCCAATACTTCAGTGC-
ACGCCTAGGCCATCGCCTAGACCATCGCGAGGACTACACGTCCTAACGGGTCTTACGTGCGATGTCCTTTGGTAAGAGAAGAGAGGGTCGGCCCACGGGGTTATGAAGTCACG-
       (BamHI)ggatcc   agcgct(Eco47III)

M  G  C  C  F  S  R  A  Y  P  T  P  L  R  S  K  K  T  M  L  V  Q  K  Q  V  T  S  E  S  T  C  C  V  A  K  S  Y
ATGGGCTGCTGCTTCTCTAGAGCATATCCCACTCCACTAAGGTCCAAGAAGACGATGTTGGTCCAAAAGCAAGTCACCTCAGAGTCCACTTGCTGTGTAGCTAAATCATAT-
TACCCGACGACGAAGAGATCTCGTATAGGGTGAGGTGATTCCAGGTTCTTCTGCTACAACCAGGTTTCGTGCAGTGGAGTCTCAGGTGAACGACACATCGATTTAGTATA-
                    tctaga(XbaI)

N  R  V  T  V  M  G  G  F  K  V  E  Q  H  T  A  C  H  C  S  T  C  Y  Y  H  K  S  *
AACAGGGTCACAGTAATGGGGGGTTTCAAAGTGGAGCAACACACGGCGTGCCACTGCAGTACTTGTTATTATCACAAATCTTAAGTACC-3'
TTGTCCCAGTGTCATTACCCCCCAAAGTTTCACCTCGTTGTGTGCCCGACGGTGACGTCATGAACGTCATGAATAATAGTGTTTAGAATTCCATGGCCATG-5'
                                                                                ggtacc(KpnI)
```

FIG. 15

Preparation of a beta-subunit coding region lacking asn-linked oligosaccharide signal sequences

```
                            M  E  M  F  Q  G  L  L  L  L  L  L  L  S  M  G  G  T  W  A  S  K  E  P  L
5'-ATGAAATCGACGGAATCAGACTCGAGCCAAGGATGAGATGTTCCAGGGGTGCTGCTGCTGTTGCTGCTGCTGAGCATGGGCGGGACATGGGCATCCAAGGAGCCGCTT-
   3'-GGTTCCTACTCTACAAGGTCCCCGACGACGACGACGACTCGTACCCGCCCTGTACCCGTAGGTTCCTCGGCGAA
         ctcgag(XhoI)

R  P  R  C  R  P  I  Q  A  T  L  A  V  E  K  E  G  C  P  V  C  I  T  V  N  T  T  I  C  A  G  Y  C  P  T  M  T
CGGCCACGGTGCCGCCACGGTGCCCCATCCAAGCCACCCTGGCTGTGGAGAAGGAGGGCTGCCCCGTGTGCATCACCGTCAACACCACCATCTGTGCCGGCTACTGCCCCACCATGACC
                                                              GCCGGTGCCACGGGTAGGTTCGGTGGGACACCGAGTTGTGGTAGAGACGGCGAGTGGGATCTGG-
                                                                                                    cctnagg(MstII)

R  V  L  Q  G  V  L  R  A  L  P  Q  V  V  C  N  Y  R  D  V  R  F  E  S  I  R  L  P  G  C  P  R  G  V  N  P  V
CGCGTGCTGCAGGGGTCCTGCGCCCTGCCCCAGGTGGTGTGCAACTACCGCGATGTGCGCTTCGAGTCCATCCGGCTCCCTGGCTGCCCGCGGGGTGAACCCGTG-
GCGCACGACGTCCCCCAGGACGGGCCCAGGACGCGGGACTCAGGACGAGGAGTCCAGTTCGGAGGGACTACGAGGCAGCCGGGACGACCGAGGGACCGACGGGCGCGCCACTTGGGCAC-
```

FIG. 16A

```
V  S  Y  A  V  A  L  S  C  Q  C  A  L  C  R  R  S  T  T  D  C  G  G  P  K  D  H  P  L  T  C  D  D  P  R  F  Q
GTCTCCTACGCCGTGGCTCTCAGCTGTCAATGTCAGTGCACTCTGCCGCCAGCACTGACTGTGGGGTCCCAAGGACCACCCTTGACTCTGTGATGACCCCGCTTCCAG-
CAGAGGATGCGGCACCGACAGTGACAGTTACACGTGACACTGAGACGGCCGGTCGTGGTGACTGAGACGCCCCAGGGTTCCTGGTGGGAACTGGACACTACTGGGGGCCGAAGGTC-

D  S  S  S  K  A  P  P  P  S  L  P  S  P  S  R  L  P  G  P  S  D  T  P  I  L  P  Q  G  S  G  S  G  S
GACTCCTCTTCCTCAAAGGCCCCTCCCCCAGCCTTCCAAGCCCATCCCCAGCCCCTCCGGGGCCCATCCGACACCCCGATCCTCCCCCAAGGATCCGGATCTGGTAGC-
CTGAGGAGAAGGAGTTTCCGGGGAGGGGTCGGAAGCCCTGGGGGACCCCCGGGAGCCTGTGGGGTAGGGCTAGGAGGGGTTCCTAGGCCATCGCCTAGACCATCG-
                                                                    gggccc(ApaI)                  ggatcc(BamHI)          agc A  P  D  V  Q  D  C  P
GCTCCTGATGTGCAGGATTGCCCA
CGAGGACTACACGTCCTAACGGGT
gct(Eco47III)
```

FIG. 16B

Coding Sequence for Single Chain Gonadotropin Analog #1a

```
                M  E  M  F  Q  G  L  L  L  L  L  L  S  M  G  G  T  W  A  S  K  E  P  L
5'-ATGAAATCGACGGAATCAGACTCGAGCCAAGATGTTCCAGGGGCTGCTGTTGCTGCTGCTGTCGATGGGCGGACATGGGCATCCAAGGAGCCGCTT-
   3'-GGTTCCTACCTCTACAAGGTCCCCGACGACGACGACGACGACTCGTACCCGCCCTGTACCCGTAGGTTCCTCGGCGAA-
           ctcgag(XhoI)

R  P  R  C  R  P  I  N  A  T  L  A  V  E  K  E  G  C  P  V  C  I  T  V  N  T  T  I  C  A  G  Y  C  P  T  M  T
CGGCCACGGTGCCGCGCCCATCAATGCCACCCTGGCTGTGGAGAAGGAGGGCTGCCCCGTGTGCATCACCGTCAACACCACCATCTGCGCTACTGCCCCACCATGACC
GCCGGTGCCACGGCGCGGGTAGTTACGGTGGGACCGACACCCTCTTCCTCCCGACGGGCACAGTAGTTGCAGTTGTGGTGTAGACACGCCGATGACGGGGTGGATCGG

R  V  L  Q  G  V  L  R  A  L  P  Q  V  V  C  N  Y  R  D  V  R  F  E  S  I  R  L  P  G  C  P  R  G  V  N  P  V
CGGTGTGCTGCAGGGGGTCCTGCGCGCCCTGCCTCAGGTGGTGCAACTACCGGGATGTGCGCTTCGAGTCCATCCGGCTCCCTGGTCCCCGCGGGGCGTGAACCCCGTG
GCCACACGACGTCCCCCAGGACGCGCGGGACCGGAGTCCACCACGTTGATGGCGCTACACGCGAAGCTCAGGTAGGCCGAGGACCGAGGGACCAGGGGCGCCCCGCACTTGGGCAC

V  S  Y  A  V  A  L  S  C  Q  C  A  L  C  R  R  S  T  T  D  C  G  G  P  K  D  H  P  L  T  C  D  D  P  R  F  Q
GTCTCCTACGCGGTGGCTCTCAGCTGTCAATGTGCACTCTGCCGCCGCAGCACTGACTGCGGGGGTCCCAAGGACCACCCCTTGACCTGTGATGACCCCGCTTCCAG
CAGAGGATGCGCCACCGACGTCGACAGTTACACGTGAGACGGCGGCGTCGTGACTGACGCCCCCAGGGTTCCTGGTGGGGAACTGGACACTACTGGGGCGAAGTC
           cctnagg(MstII)
```

*FIG. 17A*

D  S  S  S  S  K  A  P  P  P  S  L  P  S  P  S  R  L  P  G  P  S  D  T  P  I  L  P  Q  G  S  G  S  G  S
GACTCCTCCTTCCTCAAAGGCCCCCTCCCCCAGCCTTCCAAGCCCATCCTGGGCCCTGACTCCCGGACACCCGGATCCTCCCCCAGGATCCGGTAGCGGATCGGTAGC-
CTGAGGAGAAGGAGTTTCCGGGGAGGGGGTCGGAAGTTCGGTAGCCTGTGGGCTAGGAGAGGGGGTTCCATGCCATCGCCTAGACCATCG-
                                       gggccc(ApaI)       ggatcc(BamHI)          agc A  P  D  V  Q  D  C  P  E  C  T  L  Q  E  N  P  F  F  S  Q  P  G  A  P  I  L  Q  C  M  G  C  C  F  S  R  A  Y
GCTCCTGATGTGTGCAGGATTGCCAGAATGCACGCTACAGAGGAAAAACCCATTCTTCTCCCAGCCGGGTGCCCAATACTTCAGTGCATGGGCTGCTGCTTCTCTAGAGCATAT-
CGAGGACTACACGTCCTAACGGTCTTACGTGCGATGTCCTTTTGGGTAAGAAGAGGGTCGGCCCACGGGGTTATGAAGTCACGTACCCGACGACGAAGAGATCTCGTATA-
gct(Eco47III)

P  T  P  L  R  S  K  K  T  M  L  V  Q  K  Q  V  T  S  E  S  T  C  C  V  A  K  S  Y  N  R  V  T  V  M  G  G  F
CCCACTCCACTAAGGTCCAAGAAGACGATGTTGGTCCAAAAGCAAGTCACCTCAGAGTCCACTTGCTGTGTAGCTAAATCATATAACAGGTCACAGTAATGGGGGTTC-
GGGTGAGGTGATTCCAGGTTCTTCTGCTACAACCAGGTTTTCGTTCAGTGGAGTCTCAGTGAACGACACATCGATTTAGTATATTGTCCCAGTGTCATTACCCCCAAAG-

K  V  E  Q  H  T  A  C  H  C  S  T  C  Y  Y  H  K  S  *
AAAGTGGAGCAACACACGGGCGTGCCACTGCCAGTACTACTTGTTATTATCACAAAATCTTAAGTACC-3'
TTTCACCTCGTTGTGTGCCGCACGTGACGTCATGATGAACAATAATAGTGTTTAGAATTCATGCCTAGTAGAGTTCGATTAGGCCT-5'
                                (KpnI)ggtaccggatcc(BglII)

FIG. 17B

SEQUENCE LISTING (1) GENERAL INFORMATION:

(iii) NUMBER OF SEQUENCES: 83

(2) INFORMATION FOR SEQ ID NO: 1:

(i) SEQUENCE CHARACTERISTICS:
      (A) LENGTH: 28 amino acids
      (B) TYPE: amino acid
      (C) STRANDEDNESS: single
      (D) TOPOLOGY: linear (xi) SEQUENCE DESCRIPTION: SEQ ID NO: 1:

```
Ser Ser Ser Ser Lys Ala Pro Pro Pro Ser Leu Pro Ser Pro Ser Arg
 1               5                  10                  15

Leu Pro Gly Pro Ser Asp Thr Pro Ile Leu Pro Gln
            20                  25
```

(2) INFORMATION FOR SEQ ID NO: 2:

(i) SEQUENCE CHARACTERISTICS:
      (A) LENGTH: 836 base pairs
      (B) TYPE: nucleic acid
      (C) STRANDEDNESS: double
      (D) TOPOLOGY: linear (ix) FEATURE:
      (A) NAME/KEY: Coding Sequence
      (B) LOCATION: 33...827
      (D) OTHER INFORMATION:

(xi) SEQUENCE DESCRIPTION: SEQ ID NO: 2:

```
ATGAAATCGA CGGAATCAGA CTCGAGCCAA GG ATG GAG ATG TTC CAG GGG CTG       53
                                    Met Glu Met Phe Gln Gly Leu
                                     1               5

CTG CTG TTG CTG CTG CTG AGC ATG GGC GGG ACA TGG GCA TCC AAG GAG      101
Leu Leu Leu Leu Leu Leu Ser Met Gly Gly Thr Trp Ala Ser Lys Glu
         10                  15                  20

CCG CTT CGG CCA CGG TGC CGC CCC ATC AAT GCC ACC CTG GCT GTG GAG      149
Pro Leu Arg Pro Arg Cys Arg Pro Ile Asn Ala Thr Leu Ala Val Glu
     25                  30                  35

AAG GAG GGC TGC CCC GTG TGC ATC ACC GTC AAC ACC ACC ATC TGT GCC      197
Lys Glu Gly Cys Pro Val Cys Ile Thr Val Asn Thr Thr Ile Cys Ala
 40                  45                  50                  55

GGC TAC TGC CCC ACC ATG ACC CGC GTG CTG CAG GGG GTC CTG CCG GCC      245
Gly Tyr Cys Pro Thr Met Thr Arg Val Leu Gln Gly Val Leu Pro Ala
                 60                  65                  70

CTG CCT CAG GTG GTG TGC AAC TAC CGC GAT GTG CGC TTC GAG TCC ATC      293
Leu Pro Gln Val Val Cys Asn Tyr Arg Asp Val Arg Phe Glu Ser Ile
             75                  80                  85

CGG CTC CCT GGC TGC CCG CGC GGC GTG AAC CCC GTG GTC TCC TAC GCC      341
Arg Leu Pro Gly Cys Pro Arg Gly Val Asn Pro Val Val Ser Tyr Ala
         90                  95                 100

GTG GCT CTC AGC TGT CAA TGT GCA CTC TGC CGC CGC AGC ACC ACT GAC      389
Val Ala Leu Ser Cys Gln Cys Ala Leu Cys Arg Arg Ser Thr Thr Asp
     105                 110                 115

TGC GGG GGT CCC AAG GAC CAC CCC TTG ACC TGT GAT GAC CCC CGC TTC      437
Cys Gly Gly Pro Lys Asp His Pro Leu Thr Cys Asp Asp Pro Arg Phe
120                 125                 130                 135

CAG GAC TCC TCT TCC TCA AAG GCC CCT CCC CCC AGC CTT CCA AGC CCA      485
Gln Asp Ser Ser Ser Ser Lys Ala Pro Pro Pro Ser Leu Pro Ser Pro
                 140                 145                 150
```

-continued

| | |
|---|---|
| TCC CGA CTC CCG GGG CCC TCG GAC ACC CCG ATC CTC CCC CAA GGA TCC<br>Ser Arg Leu Pro Gly Pro Ser Asp Thr Pro Ile Leu Pro Gln Gly Ser<br>     155                 160                 165 | 533 |
| GGT AGC GGA TCT GGT AGC GCT CCT GAT GTG CAG GAT TGC CCA GAA TGC<br>Gly Ser Gly Ser Gly Ser Ala Pro Asp Val Gln Asp Cys Pro Glu Cys<br>         170                 175                 180 | 581 |
| ACG CTA CAG GAA AAC CCA TTC TTC TCC CAG CCG GGT GCC CCA ATA CTT<br>Thr Leu Gln Glu Asn Pro Phe Phe Ser Gln Pro Gly Ala Pro Ile Leu<br>     185                 190                 195 | 629 |
| CAG TGC ATG GGC TGC TGC TTC TCT AGA GCA TAT CCC ACT CCA CTA AGG<br>Gln Cys Met Gly Cys Cys Phe Ser Arg Ala Tyr Pro Thr Pro Leu Arg<br>200                 205                 210                 215 | 677 |
| TCC AAG AAG ACG ATG TTG GTC CAA AAG AAC GTC ACC TCA GAG TCC ACT<br>Ser Lys Lys Thr Met Leu Val Gln Lys Asn Val Thr Ser Glu Ser Thr<br>                 220                 225                 230 | 725 |
| TGC TGT GTA GCT AAA TCA TAT AAC AGG GTC ACA GTA ATG GGG GGT TTC<br>Cys Cys Val Ala Lys Ser Tyr Asn Arg Val Thr Val Met Gly Gly Phe<br>             235                 240                 245 | 773 |
| AAA GTG GAG AAC CAC ACG GCG TGC CAC TGC AGT ACT TGT TAT TAT CAC<br>Lys Val Glu Asn His Thr Ala Cys His Cys Ser Thr Cys Tyr Tyr His<br>         250                 255                 260 | 821 |
| AAA TCT TAAGGTACC<br>Lys Ser<br>     265 | 836 |

(2) INFORMATION FOR SEQ ID NO: 3:

(i) SEQUENCE CHARACTERISTICS:
        (A) LENGTH: 265 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 3:

Met Glu Met Phe Gln Gly Leu Leu Leu Leu Leu Leu Ser Met Gly
 1               5                  10                  15

Gly Thr Trp Ala Ser Lys Glu Pro Leu Arg Pro Arg Cys Arg Pro Ile
             20                  25                  30

Asn Ala Thr Leu Ala Val Glu Lys Glu Gly Cys Pro Val Cys Ile Thr
         35                  40                  45

Val Asn Thr Thr Ile Cys Ala Gly Tyr Cys Pro Thr Met Thr Arg Val
     50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
             100                 105                 110

Cys Arg Arg Ser Thr Thr Asp Cys Gly Gly Pro Lys Asp His Pro Leu
         115                 120                 125

Thr Cys Asp Asp Pro Arg Phe Gln Asp Ser Ser Ser Lys Ala Pro
     130                 135                 140

Pro Pro Ser Leu Pro Ser Pro Ser Arg Leu Pro Gly Pro Ser Asp Thr
145                 150                 155                 160

Pro Ile Leu Pro Gln Gly Ser Gly Ser Gly Ser Gly Ser Ala Pro Asp

-continued

```
                  165                 170                 175
Val Gln Asp Cys Pro Glu Cys Thr Leu Gln Glu Asn Pro Phe Phe Ser
                180                 185                 190
Gln Pro Gly Ala Pro Ile Leu Gln Cys Met Gly Cys Cys Phe Ser Arg
            195                 200                 205
Ala Tyr Pro Thr Pro Leu Arg Ser Lys Lys Thr Met Leu Val Gln Lys
        210                 215                 220
Asn Val Thr Ser Glu Ser Thr Cys Cys Val Ala Lys Ser Tyr Asn Arg
225                 230                 235                 240
Val Thr Val Met Gly Gly Phe Lys Val Glu Asn His Thr Ala Cys His
                245                 250                 255
Cys Ser Thr Cys Tyr Tyr His Lys Ser
            260                 265
```

(2) INFORMATION FOR SEQ ID NO: 4:

(i) SEQUENCE CHARACTERISTICS:
        (A) LENGTH: 834 base pairs
        (B) TYPE: nucleic acid
        (C) STRANDEDNESS: double
        (D) TOPOLOGY: linear (xi) SEQUENCE DESCRIPTION: SEQ ID NO: 4:

```
TCCGGATTAG CTTGAGATGG ATCCGGTACC TTAAGATTTG TGATAATAAC AAGTACTGCA      60
GTGGCACGCC GTGTGGTTCT CCACTTTGAA ACCCCCCATT ACTGTGACCC TGTTATATGA     120
TTTAGCTACA CAGCAAGTGG ACTCTGAGGT GACGTTCTTT TGGACCAACA TCGTCTTCTT     180
GGACCTTAGT GGAGTGGGAT ATGCTCTAGA GAAGCAGCAG CCCATGCACT GAAGTATTGG     240
GGCACCCGGC TGGGAGAAGA ATGGGTTTTC CTGTAGCGTG CATTCTGGGC AATCCTGCAC     300
ATCAGGAGCG CTACCAGATC CGCTACCGGA TCCTTGGGGG AGGATCGGGG TGTCCGAGGG     360
CCCCGGGAGT CGGGATGGGC TTGGAAGGCT GGGGGGAGGG GCCTTTGAGG AAGAGGAGTC     420
CTGGAAGCGG GGGTCATCAC AGGTCAAGGG GTGGTCCTTG GACCCCCGC AGTCAGTGGT     480
GCTGCGGCGG CAGAGTGCAC ATTGACAGCT GAGAGCCACG GCGTAGGAGA CCACGGGGTT     540
CACGCCGCGC GGGCAGCCAG GGAGCCGGAT GGACTCGAAG CGCACATCGC GGTAGTTGCA     600
CACCACCTGA GGCAGGGCCG GCAGGACCCC CTGCAGCACG CGGGTCATGG TGGGGCAGTA     660
GCCGGCACAG ATGGTGGTGT TGACGGTGAT GCACACGGGG CAGCCCTCCT TCTCCACAGC     720
CAGGGTGGCA TTGATGGGGC GGCACCGTGG CCGAAGCGGC TCCTTGGATG CCCATGTCCC     780
GCCCATGCTC AGCAGCAGCA ACAGCAGCAG CCCCTGGAAC ATCTCCATCC TTGG           834
```

(2) INFORMATION FOR SEQ ID NO: 5:

(i) SEQUENCE CHARACTERISTICS:
        (A) LENGTH: 743 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 33...734
        (D) OTHER INFORMATION:

(xi) SEQUENCE DESCRIPTION: SEQ ID NO: 5:

```
ATGAAATCGA CGGAATCAGA CTCGAGCCAA GG ATG GAG ATG TTC CAG GGG CTG       53
                                   Met Glu Met Phe Gln Gly Leu
                                    1               5
```

```
CTG CTG TTG CTG CTG CTG AGC ATG GGC GGG ACA TGG GCA TCC AAG GAG        101
Leu Leu Leu Leu Leu Leu Ser Met Gly Gly Thr Trp Ala Ser Lys Glu
            10                  15                  20

CCG CTT CGG CCA CGG TGC CGC CCC ATC AAT GCC ACC CTG GCT GTG GAG        149
Pro Leu Arg Pro Arg Cys Arg Pro Ile Asn Ala Thr Leu Ala Val Glu
        25                  30                  35

AAG GAG GGC TGC CCC GTG TGC ATC ACC GTC AAC ACC ACC ATC TGT GCC        197
Lys Glu Gly Cys Pro Val Cys Ile Thr Val Asn Thr Thr Ile Cys Ala
40                  45                  50                  55

GGC TAC TGC CCC ACC ATG ACC CGC GTG CTG CAG GGG GTC CTG CCG GCC        245
Gly Tyr Cys Pro Thr Met Thr Arg Val Leu Gln Gly Val Leu Pro Ala
                60                  65                  70

CTG CCT CAG GTG GTG TGC AAC TAC CGC GAT GTG CGC TTC GAG TCC ATC        293
Leu Pro Gln Val Val Cys Asn Tyr Arg Asp Val Arg Phe Glu Ser Ile
            75                  80                  85

CGG CTC CCT GGC TGC CCG CGC GGC GTG AAC CCC GTG GTC TCC TAC GCC        341
Arg Leu Pro Gly Cys Pro Arg Gly Val Asn Pro Val Val Ser Tyr Ala
        90                  95                  100

GTG GCT CTC AGC TGT CAA TGT GCA CTC TGC CGC CGC AGC ACC ACT GAC        389
Val Ala Leu Ser Cys Gln Cys Ala Leu Cys Arg Arg Ser Thr Thr Asp
    105                 110                 115

TGC GGG GGT CCC AAG GAC CAC CCC TTG ACC TGT GAT GAC CCG CGG GGA        437
Cys Gly Gly Pro Lys Asp His Pro Leu Thr Cys Asp Asp Pro Arg Gly
120                 125                 130                 135

TCC GGT AGC GGA TCT GGT AGC GCT CCT GAT GTG CAG GAT TGC CCA GAA        485
Ser Gly Ser Gly Ser Gly Ser Ala Pro Asp Val Gln Asp Cys Pro Glu
                140                 145                 150

TGC ACG CTA CAG GAA AAC CCA TTC TTC TCC CAG CCG GGT GCC CCA ATA        533
Cys Thr Leu Gln Glu Asn Pro Phe Phe Ser Gln Pro Gly Ala Pro Ile
            155                 160                 165

CTT CAG TGC ATG GGC TGC TGC TTC TCT AGA GCA TAT CCC ACT CCA CTA        581
Leu Gln Cys Met Gly Cys Cys Phe Ser Arg Ala Tyr Pro Thr Pro Leu
        170                 175                 180

AGG TCC AAG AAG ACG ATG TTG GTC CAA AAG AAC GTC ACC TCA GAG TCC        629
Arg Ser Lys Lys Thr Met Leu Val Gln Lys Asn Val Thr Ser Glu Ser
185                 190                 195

ACT TGC TGT GTA GCT AAA TCA TAT AAC AGG GTC ACA GTA ATG GGG GGT        677
Thr Cys Cys Val Ala Lys Ser Tyr Asn Arg Val Thr Val Met Gly Gly
200                 205                 210                 215

TTC AAA GTG GAG AAC CAC ACG GCG TGC CAC TGC AGT ACT TGT TAT TAT        725
Phe Lys Val Glu Asn His Thr Ala Cys His Cys Ser Thr Cys Tyr Tyr
                220                 225                 230

CAC AAA TCT TAAGGTACC                                                  743
His Lys Ser (2) INFORMATION FOR SEQ ID NO: 6:

(i) SEQUENCE CHARACTERISTICS:
        (A) LENGTH: 234 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 6:

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30
```

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
            115                 120                 125

Thr Cys Asp Asp Pro Arg Gly Ser Gly Ser Gly Ser Ala Pro
130                 135                 140

Asp Val Gln Asp Cys Pro Glu Cys Thr Leu Gln Glu Asn Pro Phe Phe
145                 150                 155                 160

Ser Gln Pro Gly Ala Pro Ile Leu Gln Cys Met Gly Cys Cys Phe Ser
                165                 170                 175

Arg Ala Tyr Pro Thr Pro Leu Arg Ser Lys Lys Thr Met Leu Val Gln
            180                 185                 190

Lys Asn Val Thr Ser Glu Ser Thr Cys Cys Val Ala Lys Ser Tyr Asn
            195                 200                 205

Arg Val Thr Val Met Gly Gly Phe Lys Val Glu Asn His Thr Ala Cys
            210                 215                 220

His Cys Ser Thr Cys Tyr Tyr His Lys Ser
225                 230

(2) INFORMATION FOR SEQ ID NO: 7:

(i) SEQUENCE CHARACTERISTICS:
        (A) LENGTH: 717 base pairs
        (B) TYPE: nucleic acid
        (C) STRANDEDNESS: double
        (D) TOPOLOGY: linear (xi) SEQUENCE DESCRIPTION: SEQ ID NO: 7:

GGTACCTTAA GATTTGTGAT AATAACAAGT ACTGCAGTGG CACGCCGTGT GGTTCTCCAC     60

TTTGAAACCC CCCATTACTG TGACCCTGTT ATATGATTTA GCTACACAGC AAGTGGACTC    120

TGAGGTGACG TTCTTTTGGA CCAACATCGT CTTCTTGGAC CTTAGTGGAG TGGGATATGC    180

TCTAGAGAAG CAGCAGCCCA TGCACTGAAG TATTGGGGCA CCCGGCTGGG AGAAGAATGG    240

GTTTTCCTGT AGCGTGCATT CTGGGCAATC CTGCACATCA GGAGCGCTAC CAGATCCGCT    300

ACCGGATCCC CGCGGGTCAT CACAGGTCAA GGGGTGGTCC TTGGGACCCC CGCAGTCAGT    360

GGTGCTGCGG CGGCAGAGTG CACATTGACA GCTGAGAGCC ACGGCGTAGG AGACCACGGG    420

GTTCACGCCG CGCGGGCAGC CAGGGAGCCG GATGGACTCG AAGCGCACAT CGCGGTAGTT    480

GCACACCACC TGAGGCAGGG CCGGCAGGAC CCCCTGCAGC ACGCGGGTCA TGGTGGGGCA    540

GTAGCCGGCA CAGATGGTGG TGTTGACGGT GATGCACACG GGGCAGCCCT CCTTCTCCAC    600

AGCCAGGGTG GCATTGATGG GGCGGCACCG TGGCCGAAGC GGCTCCTTGG ATGCCCATGT    660

CCCGCCCATG CTCAGCAGCA GCAACAGCAG CAGCCCCTGG AACATCTCCA TCCTTGG      717

(2) INFORMATION FOR SEQ ID NO: 8:

(i) SEQUENCE CHARACTERISTICS:

(A) LENGTH: 744 base pairs
            (B) TYPE: nucleic acid
            (C) STRANDEDNESS: double
            (D) TOPOLOGY: linear (ix) FEATURE:
            (A) NAME/KEY: Coding Sequence
            (B) LOCATION: 34...735
            (D) OTHER INFORMATION:

(xi) SEQUENCE DESCRIPTION: SEQ ID NO: 8:

```
ATGAAATCGA CGGAATCAGA CTCGAGCCAA GGA ATG GAG ATG CTC CAG GGG CTG         54
                                  Met Glu Met Leu Gln Gly Leu
                                   1               5

CTG CTG TTG CTG CTG CTG AGC ATG GGC GGG GCA TGG GCA TCC AGG GAG        102
Leu Leu Leu Leu Leu Leu Ser Met Gly Gly Ala Trp Ala Ser Arg Glu
         10                  15                  20

CCG CTT CGG CCA TGG TGC CAC CCC ATC AAT GCC ATC CTG GCT GTG GAG        150
Pro Leu Arg Pro Trp Cys His Pro Ile Asn Ala Ile Leu Ala Val Glu
 25                  30                  35

AAG GAG GGC TGC CCC GTG TGC ATC ACC GTC AAC ACC ACC ATC TGT GCC        198
Lys Glu Gly Cys Pro Val Cys Ile Thr Val Asn Thr Thr Ile Cys Ala
 40                  45                  50                  55

GGC TAC TGC CCC ACC ATG ATG CGC GTG CTG CAG GCG GTC CTG CCG CCC        246
Gly Tyr Cys Pro Thr Met Met Arg Val Leu Gln Ala Val Leu Pro Pro
                 60                  65                  70

CTG CCT CAG GTG GTG TGC ACC TAC CGT GAT GTG CGC TTC GAG TCC ATC        294
Leu Pro Gln Val Val Cys Thr Tyr Arg Asp Val Arg Phe Glu Ser Ile
             75                  80                  85

CGG CTC CCT GGC TGC CCG CGT GGC GTG GAC CCC GTG GTC TCC TTC CCT        342
Arg Leu Pro Gly Cys Pro Arg Gly Val Asp Pro Val Val Ser Phe Pro
         90                  95                 100

GTG GCT CTC AGC TGT CGC TGT GGA CCC TGC CGC CGC AGC ACC TCT GAC        390
Val Ala Leu Ser Cys Arg Cys Gly Pro Cys Arg Arg Ser Thr Ser Asp
105                 110                 115

TGT GGG GGT CCC AAA GAC CAC CCC TTG ACC TGT GAC CAC CCC CAA GGA        438
Cys Gly Gly Pro Lys Asp His Pro Leu Thr Cys Asp His Pro Gln Gly
120                 125                 130                 135

TCC GGT AGC GGA TCT GGT AGC GCT CCT GAT GTG CAG GAT TGC CCA GAA        486
Ser Gly Ser Gly Ser Gly Ser Ala Pro Asp Val Gln Asp Cys Pro Glu
                140                 145                 150

TGC ACG CTA CAG GAA AAC CCA TTC TTC TCC CAG CCG GGT GCC CCA ATA        534
Cys Thr Leu Gln Glu Asn Pro Phe Phe Ser Gln Pro Gly Ala Pro Ile
            155                 160                 165

CTT CAG TGC ATG GGC TGC TGC TTC TCT AGA GCA TAT CCC ACT CCA CTA        582
Leu Gln Cys Met Gly Cys Cys Phe Ser Arg Ala Tyr Pro Thr Pro Leu
        170                 175                 180

AGG TCC AAG AAG ACG ATG TTG GTC CAA AAG AAC GTC ACC TCA GAG TCC        630
Arg Ser Lys Lys Thr Met Leu Val Gln Lys Asn Val Thr Ser Glu Ser
185                 190                 195

ACT TGC TGT GTA GCT AAA TCA TAT AAC AGG GTC ACA GTA ATG GGG GGT        678
Thr Cys Cys Val Ala Lys Ser Tyr Asn Arg Val Thr Val Met Gly Gly
200                 205                 210                 215

TTC AAA GTG GAG AAC CAC ACG GCG TGC CAC TGC AGT ACT TGT TAT TAT        726
Phe Lys Val Glu Asn His Thr Ala Cys His Cys Ser Thr Cys Tyr Tyr
                220                 225                 230

CAC AAA TCT TAAGGTACC                                                  744
His Lys Ser
```

(2) INFORMATION FOR SEQ ID NO: 9:

(i) SEQUENCE CHARACTERISTICS:

(A) LENGTH: 234 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 9:

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
            35                  40                  45

Val Asn Thr Thr Ile Cys Ala Gly Tyr Cys Pro Thr Met Met Arg Val
    50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
                100                 105                 110

Cys Arg Arg Ser Thr Ser Asp Cys Gly Gly Pro Lys Asp His Pro Leu
            115                 120                 125

Thr Cys Asp His Pro Gln Gly Ser Gly Ser Gly Ser Gly Ser Ala Pro
130                 135                 140

Asp Val Gln Asp Cys Pro Glu Cys Thr Leu Gln Glu Asn Pro Phe Phe
145                 150                 155                 160

Ser Gln Pro Gly Ala Pro Ile Leu Gln Cys Met Gly Cys Cys Phe Ser
                165                 170                 175

Arg Ala Tyr Pro Thr Pro Leu Arg Ser Lys Lys Thr Met Leu Val Gln
            180                 185                 190

Lys Asn Val Thr Ser Glu Ser Thr Cys Cys Val Ala Lys Ser Tyr Asn
            195                 200                 205

Arg Val Thr Val Met Gly Gly Phe Lys Val Glu Asn His Thr Ala Cys
210                 215                 220

His Cys Ser Thr Cys Tyr Tyr His Lys Ser
225                 230

(2) INFORMATION FOR SEQ ID NO: 10:

(i) SEQUENCE CHARACTERISTICS:
        (A) LENGTH: 718 base pairs
        (B) TYPE: nucleic acid
        (C) STRANDEDNESS: double
        (D) TOPOLOGY: linear (xi) SEQUENCE DESCRIPTION: SEQ ID NO: 10:

GGTACCTTAA GATTTGTGAT AATAACAAGT ACTGCAGTGG CACGCCGTGT GGTTCTCCAC      60

TTTGAAACCC CCCATTACTG TGACCCTGTT ATATGATTTA GCTACACAGC AAGTGGACTC     120

TGAGGTGACG TTCTTTTGGA CCAACATCGT CTTCTTGGAC CTTAGTGGAG TGGGATATGC     180

TCTAGAGAAG CAGCAGCCCA TGCACTGAAG TATTGGGGCA CCCGGCTGGG AGAAGAATGG     240

GTTTTCCTGT AGCGTGCATT CTGGGCAATC CTGCACATCA GGAGCGCTAC CAGATCCGCT     300

ACCGGATCCT TGGGGGTGGT CACAGGTCAA GGGGTGGTCT TTGGGACCCC CACAGTCAGA     360

-continued

```
GGTGCTGCGG CGGCAGGGTC CACAGCGACA GCTGAGAGCC ACAGGGAAGG AGACCACGGG       420

GTCCACGCCA CGCGGGCAGC CAGGGAGCCG GATGGACTCG AAGCGCACAT CACGGTAGGT       480

GCACACCACC TGAGGCAGGG GCGGCAGGAC CGCCTGCAGC ACGCGCATCA TGGTGGGGCA       540

GTAGCCGGCA CAGATGGTGG TGTTGACGGT GATGCACACG GGGCAGCCCT CCTTCTCCAC       600

AGCCAGGATG GCATTGATGG GGTGGCACCA TGGCCGAAGC GGCTCCCTGG ATGCCCATGC       660

CCCGCCCATG CTCAGCAGCA GCAACAGCAG CAGCCCCTGG AGCATCTCCA TTCCTTGG         718
```

(2) INFORMATION FOR SEQ ID NO: 11:

(i) SEQUENCE CHARACTERISTICS:
        (A) LENGTH: 728 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 33...719
        (D) OTHER INFORMATION:

(xi) SEQUENCE DESCRIPTION: SEQ ID NO: 11:

```
ATGAAATCGA CGGAATCAGA CTCGAGCCAA GG ATG AAG ACA CTC CAG TTT TTC             53
                                  Met Lys Thr Leu Gln Phe Phe
                                   1               5

TTC CTT TTC TGT TGC TGG AAA GCA ATC TGC TGC AAT AGC TGT GAG CTG            101
Phe Leu Phe Cys Cys Trp Lys Ala Ile Cys Cys Asn Ser Cys Glu Leu
        10              15                  20

ACC AAC ATC ACC ATT GCA ATA GAG AAA GAA GAA TGT CGT TTC TGC ATA            149
Thr Asn Ile Thr Ile Ala Ile Glu Lys Glu Glu Cys Arg Phe Cys Ile
     25                  30                  35

AGC ATC AAC ACC ACT TGG TGT GCT GGC TAC TGC TAC ACC AGG GAT CTG            197
Ser Ile Asn Thr Thr Trp Cys Ala Gly Tyr Cys Tyr Thr Arg Asp Leu
 40                  45                  50                  55

GTG TAT AAG GAC CCA GCC AGG CCC AAA ATC CAG AAA ACA TGT ACC TTC            245
Val Tyr Lys Asp Pro Ala Arg Pro Lys Ile Gln Lys Thr Cys Thr Phe
             60                  65                  70

AAG GAA CTG GTA TAT GAA ACA GTG AGA GTG CCC GGC TGT GCT CAC CAT            293
Lys Glu Leu Val Tyr Glu Thr Val Arg Val Pro Gly Cys Ala His His
             75                  80                  85

GCA GAT TCC TTG TAT ACA TAC CCA GTG GCC ACC CAG TGT CAC TGT GGC            341
Ala Asp Ser Leu Tyr Thr Tyr Pro Val Ala Thr Gln Cys His Cys Gly
             90                  95                 100

AAG TGT GAC AGC GAC AGC ACT GAT TGT ACT GTG CGA GGC CTG GGG CCC            389
Lys Cys Asp Ser Asp Ser Thr Asp Cys Thr Val Arg Gly Leu Gly Pro
        105                 110                 115

AGC TAC TGC TCC TTT GGT GAA ATG AAA GAA GGA TCC GGT AGC GGA TCT            437
Ser Tyr Cys Ser Phe Gly Glu Met Lys Glu Gly Ser Gly Ser Gly Ser
120                 125                 130                 135

GGT AGC GCT CCT GAT GTG CAG GAT TGC CCA GAA TGC ACG CTA CAG GAA            485
Gly Ser Ala Pro Asp Val Gln Asp Cys Pro Glu Cys Thr Leu Gln Glu
             140                 145                 150

AAC CCA TTC TTC TCC CAG CCG GGT GCC CCA ATA CTT CAG TGC ATG GGC            533
Asn Pro Phe Phe Ser Gln Pro Gly Ala Pro Ile Leu Gln Cys Met Gly
             155                 160                 165

TGC TGC TTC TCT AGA GCA TAT CCC ACT CCA CTA AGG TCC AAG AAG ACG            581
Cys Cys Phe Ser Arg Ala Tyr Pro Thr Pro Leu Arg Ser Lys Lys Thr
        170                 175                 180

ATG TTG GTC CAA AAG AAC GTC ACC TCA GAG TCC ACT TGC TGT GTA GCT            629
Met Leu Val Gln Lys Asn Val Thr Ser Glu Ser Thr Cys Cys Val Ala
        185                 190                 195
```

```
AAA TCA TAT AAC AGG GTC ACA GTA ATG GGG GGT TTC AAA GTG GAG AAC      677
Lys Ser Tyr Asn Arg Val Thr Val Met Gly Gly Phe Lys Val Glu Asn
200             205                 210                 215

CAC ACG GCG TGC CAC TGC AGT ACT TGT TAT TAT CAC AAA TCT TAAGGTACC    728
His Thr Ala Cys His Cys Ser Thr Cys Tyr Tyr His Lys Ser
                220                 225

728
```

(2) INFORMATION FOR SEQ ID NO: 12:

(i) SEQUENCE CHARACTERISTICS:
        (A) LENGTH: 229 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 12:

```
Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
                35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
                100                 105                 110

Thr Val Arg Gly Leu Gly Pro Ser Tyr Cys Ser Phe Gly Glu Met Lys
            115                 120                 125

Glu Gly Ser Gly Ser Gly Ser Ala Pro Asp Val Gln Asp Cys
130                 135                 140

Pro Glu Cys Thr Leu Gln Glu Asn Pro Phe Phe Ser Gln Pro Gly Ala
145                 150                 155                 160

Pro Ile Leu Gln Cys Met Gly Cys Cys Phe Ser Arg Ala Tyr Pro Thr
                165                 170                 175

Pro Leu Arg Ser Lys Lys Thr Met Leu Val Gln Lys Asn Val Thr Ser
            180                 185                 190

Glu Ser Thr Cys Cys Val Ala Lys Ser Tyr Asn Arg Val Thr Val Met
            195                 200                 205

Gly Gly Phe Lys Val Glu Asn His Thr Ala Cys His Cys Ser Thr Cys
210                 215                 220

Tyr Tyr His Lys Ser
225
```

(2) INFORMATION FOR SEQ ID NO: 13:

(i) SEQUENCE CHARACTERISTICS:
        (A) LENGTH: 702 base pairs
        (B) TYPE: nucleic acid
        (C) STRANDEDNESS: double
        (D) TOPOLOGY: linear (xi) SEQUENCE DESCRIPTION: SEQ ID NO: 13:

```
GGTACCTTAA GATTTGTGAT AATAACAAGT ACTGCAGTGG CACGCCGTGT GGTTCTCCAC    60
TTTGAAACCC CCCATTACTG TGACCCTGTT ATATGATTTA GCTACACAGC AAGTGGACTC   120
TGAGGTGACG TTCTTTTGGA CCAACATCGT CTTCTTGGAC CTTAGTGGAG TGGGATATGC   180
TCTAGAGAAG CAGCAGCCCA TGCACTGAAG TATTGGGGCA CCCGGCTGGG AGAAGAATGG   240
GTTTTCCTGT AGCGTGCATT CTGGGCAATC CTGCACATCA GGAGCGCTAC CAGATCCGCT   300
ACCGGATCCT TCTTTCATTT CACCAAAGGA GCAGTAGCTG GGCCCCAGGC CTCGCACAGT   360
ACAATCAGTG CTGTCGCTGT CACACTTGCC ACAGTGACAC TGGGTGGCCA CTGGGTATGT   420
ATACAAGGAA TCTGCATGGT GAGCACAGCC GGGCACTCTC ACTGTTTCAT ATACCAGTTC   480
CTTGAAGGTA CATGTTTTCT GGATTTTGGG CCTGGCTGGG TCCTTATACA CCAGATCCCT   540
GGTGTAGCAG TAGCCAGCAC ACCAAGTGGT GTTGATGCTT ATGCAGAAAC GACATTCTTC   600
TTTCTCTATT GCAATGGTGA TGTTGGTCAG CTCACAGCTA TTGCAGCAGA TTGCTTTCCA   660
GCAACAGAAA AGGAAGAAAA ACTGGAGTGT CTTCATCCTT GG                      702
```

(2) INFORMATION FOR SEQ ID NO: 14:

(i) SEQUENCE CHARACTERISTICS:
        (A) LENGTH: 752 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 33...743
        (D) OTHER INFORMATION:

(xi) SEQUENCE DESCRIPTION: SEQ ID NO: 14:

```
ATGAAATCGA CGGAATCAGA CTCGAGCCAA GG ATG GAG ATG TTC CAG GGG CTG       53
                                   Met Glu Met Phe Gln Gly Leu
                                    1               5

CTG CTG TTG CTG CTG CTG AGC ATG GGC GGG ACA TGG GCA TCC AAG GAG      101
Leu Leu Leu Leu Leu Leu Ser Met Gly Gly Thr Trp Ala Ser Lys Glu
         10                  15                  20

CCG CTT CGG CCA CGG TGC CGC CCC ATC AAT GCC ACC CTG GCT GTG GAG      149
Pro Leu Arg Pro Arg Cys Arg Pro Ile Asn Ala Thr Leu Ala Val Glu
    25                  30                  35

AAG GAG GGC TGC CCC GTG TGC ATC ACC GTC AAC ACC ACC ATC TGT GCC      197
Lys Glu Gly Cys Pro Val Cys Ile Thr Val Asn Thr Thr Ile Cys Ala
 40                  45                  50                  55

GGC TAC TGC CCC ACC ATG ACC CGC GTG CTG CAG GGG GTC CTG CCG GCC      245
Gly Tyr Cys Pro Thr Met Thr Arg Val Leu Gln Gly Val Leu Pro Ala
                 60                  65                  70

CTG CCT CAG GTG GTG TGC AAC TAC CGC GAT GTG CGC TTC GAG TCC ATC      293
Leu Pro Gln Val Val Cys Asn Tyr Arg Asp Val Arg Phe Glu Ser Ile
             75                  80                  85

CGG CTC CCT GGC TGC CCG CGC GGC GTG AAC CCC GTG GTC TCC TAC GCC      341
Arg Leu Pro Gly Cys Pro Arg Gly Val Asn Pro Val Val Ser Tyr Ala
         90                  95                 100

GTG GCT CTC AGC TGT CAA TGT GCA CTC TGC GAC AGC GAC AGC ACT GAT      389
Val Ala Leu Ser Cys Gln Cys Ala Leu Cys Asp Ser Asp Ser Thr Asp
    105                 110                 115

TGT ACT GTG CGA GGC CTG GGG CCC AGC TAC TGC TCC TTT GGT GAA ATG      437
Cys Thr Val Arg Gly Leu Gly Pro Ser Tyr Cys Ser Phe Gly Glu Met
120                 125                 130                 135
```

```
AAA GAA GGA TCC GGT AGC GGA TCT GGT AGC GCT CCT GAT GTG CAG GAT       485
Lys Glu Gly Ser Gly Ser Gly Ser Gly Ser Ala Pro Asp Val Gln Asp
            140                 145                 150

TGC CCA GAA TGC ACG CTA CAG GAA AAC CCA TTC TTC TCC CAG CCG GGT       533
Cys Pro Glu Cys Thr Leu Gln Glu Asn Pro Phe Phe Ser Gln Pro Gly
            155                 160                 165

GCC CCA ATA CTT CAG TGC ATG GGC TGC TGC TTC TCT AGA GCA TAT CCC       581
Ala Pro Ile Leu Gln Cys Met Gly Cys Cys Phe Ser Arg Ala Tyr Pro
            170                 175                 180

ACT CCA CTA AGG TCC AAG AAG ACG ATG TTG GTC CAA AAG AAC GTC ACC       629
Thr Pro Leu Arg Ser Lys Lys Thr Met Leu Val Gln Lys Asn Val Thr
    185                 190                 195

TCA GAG TCC ACT TGC TGT GTA GCT AAA TCA TAT AAC AGG GTC ACA GTA       677
Ser Glu Ser Thr Cys Cys Val Ala Lys Ser Tyr Asn Arg Val Thr Val
200                 205                 210                 215

ATG GGG GGT TTC AAA GTG GAG AAC CAC ACG GCG TGC CAC TGC AGT ACT       725
Met Gly Gly Phe Lys Val Glu Asn His Thr Ala Cys His Cys Ser Thr
                220                 225                 230

TGT TAT TAT CAC AAA TCT TAAGGTACC                                     752
Cys Tyr Tyr His Lys Ser
            235

(2) INFORMATION FOR SEQ ID NO: 15:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 15:

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
            85                  90                  95

Asn Pro Val Val Ser Tyr Ala Val Ala Leu Ser Cys Gln Cys Ala Leu
            100                 105                 110

Cys Asp Ser Asp Ser Thr Asp Cys Thr Val Arg Gly Leu Gly Pro Ser
            115                 120                 125

Tyr Cys Ser Phe Gly Glu Met Lys Glu Gly Ser Gly Ser Gly Ser Gly
            130                 135                 140

Ser Ala Pro Asp Val Gln Asp Cys Pro Glu Cys Thr Leu Gln Glu Asn
145                 150                 155                 160

Pro Phe Phe Ser Gln Pro Gly Ala Pro Ile Leu Gln Cys Met Gly Cys
                165                 170                 175

Cys Phe Ser Arg Ala Tyr Pro Thr Pro Leu Arg Ser Lys Lys Thr Met
            180                 185                 190
```

```
Leu Val Gln Lys Asn Val Thr Ser Glu Ser Thr Cys Cys Val Ala Lys
            195                 200                 205

Ser Tyr Asn Arg Val Thr Val Met Gly Gly Phe Lys Val Glu Asn His
            210                 215                 220

Thr Ala Cys His Cys Ser Thr Cys Tyr Tyr His Lys Ser
225                 230                 235
```

(2) INFORMATION FOR SEQ ID NO: 16:

(i) SEQUENCE CHARACTERISTICS:
        (A) LENGTH: 726 base pairs
        (B) TYPE: nucleic acid
        (C) STRANDEDNESS: double
        (D) TOPOLOGY: linear (xi) SEQUENCE DESCRIPTION: SEQ ID NO: 16:

```
GGTACCTTAA GATTTGTGAT AATAACAAGT ACTGCAGTGG CACGCCGTGT GGTTCTCCAC    60

TTTGAAACCC CCCATTACTG TGACCCTGTT ATATGATTTA GCTACACAGC AAGTGGACTC   120

TGAGGTGACG TTCTTTTGGA CCAACATCGT CTTCTTGGAC CTTAGTGGAG TGGGATATGC   180

TCTAGAGAAG CAGCAGCCCA TGCACTGAAG TATTGGGCA CCCGGCTGGG AGAAGAATGG    240

GTTTTCCTGT AGCGTGCATT CTGGGCAATC CTGCACATCA GGAGCGCTAC CAGATCCGCT   300

ACCGGATCCT TCTTTCATTT CACCAAAGGA GCAGTAGCTG GCCCCAGGC CTCGCACAGT    360

ACAATCAGTG CTGTCGCTGT CGCAGAGTGC ACATTGACAG CTGAGAGCCA CGGCGTAGGA   420

GACCACGGGG TTCACGCCGC GCGGGCAGCC AGGGAGCCGG ATGGACTCGA AGCGCACATC   480

GCGGTAGTTG CACACCACCT GAGGCAGGGC CGGCAGGACC CCCTGCAGCA CGCGGGTCAT   540

GGTGGGGCAG TAGCCGGCAC AGATGGTGGT GTTGACGGTG ATGCACACGG GGCAGCCCTC   600

CTTCTCCACA GCCAGGGTGG CATTGATGGG GCGGCACCGT GGCCGAAGCG GCTCCTTGGA   660

TGCCCATGTC CCGCCCATGC TCAGCAGCAG CAACAGCAGC AGCCCCTGGA ACATCTCCAT   720

CCTTGG                                                             726
```

(2) INFORMATION FOR SEQ ID NO: 17:

(i) SEQUENCE CHARACTERISTICS:
        (A) LENGTH: 752 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 33...743
        (D) OTHER INFORMATION:

(xi) SEQUENCE DESCRIPTION: SEQ ID NO: 17:

```
ATGAAATCGA CGGAATCAGA CTCGAGCCAA GG ATG GAG ATG TTC CAG GGG CTG     53
                                  Met Glu Met Phe Gln Gly Leu
                                   1               5

CTG CTG TTG CTG CTG CTG AGC ATG GGC GGG ACA TGG GCA TCC AAG GAG    101
Leu Leu Leu Leu Leu Leu Ser Met Gly Gly Thr Trp Ala Ser Lys Glu
        10                  15                  20

CCG CTT CGG CCA CGG TGC CGC CCC ATC AAT GCC ACC CTG GCT GTG GAG    149
Pro Leu Arg Pro Arg Cys Arg Pro Ile Asn Ala Thr Leu Ala Val Glu
    25                  30                  35

AAG GAG GGC TGC CCC GTG TGC ATC ACC GTC AAC ACC ACC ATC TGT GCC    197
Lys Glu Gly Cys Pro Val Cys Ile Thr Val Asn Thr Thr Ile Cys Ala
40                  45                  50                  55

GGC TAC TGC CCC ACC ATG ACC CGC GTG CTG CAG GGG GTC CTG CCG GCC    245
```

```
Gly Tyr Cys Pro Thr Met Thr Arg Val Leu Gln Gly Val Leu Pro Ala
                60                  65                  70

CTG CCT CAG GTG GTG TGC AAC TAC CGC GAT GTG CGC TTC GAG TCC ATC         293
Leu Pro Gln Val Val Cys Asn Tyr Arg Asp Val Arg Phe Glu Ser Ile
            75                  80                  85

CGG CTC CCT GGC TGC CCG CGC GGC GTG AAC CCC GTG GTC TCC TAC GCC         341
Arg Leu Pro Gly Cys Pro Arg Gly Val Asn Pro Val Val Ser Tyr Ala
            90                  95                  100

GTG GCT CTC AGC TGT CAA TGT GCA CTC TGC CGC CGC AGC ACC ACT GAC         389
Val Ala Leu Ser Cys Gln Cys Ala Leu Cys Arg Arg Ser Thr Thr Asp
        105                 110                 115

TGC ACT GTG CGA GGC CTG GGG CCC AGC TAC TGC TCC TTT GGT GAA ATG         437
Cys Thr Val Arg Gly Leu Gly Pro Ser Tyr Cys Ser Phe Gly Glu Met
120                 125                 130                 135

AAA GAA GGA TCC GGT AGC GGA TCT GGT AGC GCT CCT GAT GTG CAG GAT         485
Lys Glu Gly Ser Gly Ser Gly Ser Gly Ser Ala Pro Asp Val Gln Asp
                140                 145                 150

TGC CCA GAA TGC ACG CTA CAG GAA AAC CCA TTC TTC TCC CAG CCG GGT         533
Cys Pro Glu Cys Thr Leu Gln Glu Asn Pro Phe Phe Ser Gln Pro Gly
            155                 160                 165

GCC CCA ATA CTT CAG TGC ATG GGC TGC TGC TTC TCT AGA GCA TAT CCC         581
Ala Pro Ile Leu Gln Cys Met Gly Cys Cys Phe Ser Arg Ala Tyr Pro
            170                 175                 180

ACT CCA CTA AGG TCC AAG AAG ACG ATG TTG GTC CAA AAG AAC GTC ACC         629
Thr Pro Leu Arg Ser Lys Lys Thr Met Leu Val Gln Lys Asn Val Thr
        185                 190                 195

TCA GAG TCC ACT TGC TGT GTA GCT AAA TCA TAT AAC AGG GTC ACA GTA         677
Ser Glu Ser Thr Cys Cys Val Ala Lys Ser Tyr Asn Arg Val Thr Val
200                 205                 210                 215

ATG GGG GGT TTC AAA GTG GAG AAC CAC ACG GCG TGC CAC TGC AGT ACT         725
Met Gly Gly Phe Lys Val Glu Asn His Thr Ala Cys His Cys Ser Thr
                220                 225                 230

TGT TAT TAT CAC AAA TCT TAAGGTACC                                        752
Cys Tyr Tyr His Lys Ser
            235
```

(2) INFORMATION FOR SEQ ID NO: 18:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 18:

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
        50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95
```

```
Asn Pro Val Val Ser Tyr Ala Val Ala Leu Ser Cys Gln Cys Ala Leu
            100                 105                 110

Cys Arg Arg Ser Thr Thr Asp Cys Thr Val Arg Gly Leu Gly Pro Ser
        115                 120                 125

Tyr Cys Ser Phe Gly Glu Met Lys Glu Gly Ser Gly Ser Gly Ser Gly
        130                 135                 140

Ser Ala Pro Asp Val Gln Asp Cys Pro Glu Cys Thr Leu Gln Glu Asn
145                 150                 155                 160

Pro Phe Phe Ser Gln Pro Gly Ala Pro Ile Leu Gln Cys Met Gly Cys
                165                 170                 175

Cys Phe Ser Arg Ala Tyr Pro Thr Pro Leu Arg Ser Lys Lys Thr Met
            180                 185                 190

Leu Val Gln Lys Asn Val Thr Ser Glu Ser Thr Cys Cys Val Ala Lys
        195                 200                 205

Ser Tyr Asn Arg Val Thr Val Met Gly Gly Phe Lys Val Glu Asn His
    210                 215                 220

Thr Ala Cys His Cys Ser Thr Cys Tyr Tyr His Lys Ser
225                 230                 235
```

(2) INFORMATION FOR SEQ ID NO: 19:

(i) SEQUENCE CHARACTERISTICS:
        (A) LENGTH: 726 base pairs
        (B) TYPE: nucleic acid
        (C) STRANDEDNESS: double
        (D) TOPOLOGY: linear (xi) SEQUENCE DESCRIPTION: SEQ ID NO: 19:

```
GGTACCTTAA GATTTGTGAT AATAACAAGT ACTGCAGTGG CACGCCGTGT GGTTCTCCAC      60

TTTGAAACCC CCCATTACTG TGACCCTGTT ATATGATTTA GCTACACAGC AAGTGGACTC     120

TGAGGTGACG TTCTTTTGGA CCAACATCGT CTTCTTGGAC CTTAGTGGAG TGGGATATGC     180

TCTAGAGAAG CAGCAGCCCA TGCACTGAAG TATTGGGGCA CCCGGCTGGG AGAAGAATGG     240

GTTTTCCTGT AGCGTGCATT CTGGGCAATC CTGCACATCA GGAGCGCTAC CAGATCCGCT     300

ACCGGATCCT TCTTTCATTT CACCAAAGGA GCAGTAGCTG GCCCCAGGC CTCGCACAGT      360

GCAGTCAGTG GTGCTGCGGC GGCAGAGTGC ACATTGACAG CTGAGAGCCA CGGCGTAGGA     420

GACCACGGGG TTCACGCCGC GCGGGCAGCC AGGGAGCCGG ATGGACTCGA AGCGCACATC     480

GCGGTAGTTG CACACCACCT GAGGCAGGGC CGGCAGGACC CCCTGCAGCA CGCGGGTCAT     540

GGTGGGGCAG TAGCCGGCAC AGATGGTGGT GTTGACGGTG ATGCACACGG GGCAGCCCTC     600

CTTCTCCACA GCCAGGGTGG CATTGATGGG GCGGCACCGT GGCCGAAGCG GCTCCTTGGA     660

TGCCCATGTC CCGCCCATGC TCAGCAGCAG CAACAGCAGC AGCCCCTGGA ACATCTCCAT     720

CCTTGG                                                               726
```

(2) INFORMATION FOR SEQ ID NO: 20:

(i) SEQUENCE CHARACTERISTICS:
        (A) LENGTH: 743 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 33...734
        (D) OTHER INFORMATION:

(xi) SEQUENCE DESCRIPTION: SEQ ID NO: 20:

| | | | | | | | | | | | | |
|---|---|---|---|---|---|---|---|---|---|---|---|---|
| ATGAAATCGA | CGGAATCAGA | CTCGAGCCAA | GG | ATG | GAG | ATG | TTC | CAG | GGG | CTG | | 53 |
| | | | | Met | Glu | Met | Phe | Gln | Gly | Leu | | |
| | | | | 1 | | | | 5 | | | | |

```
CTG CTG TTG CTG CTG CTG AGC ATG GGC GGG ACA TGG GCA TCC AAG GAG         101
Leu Leu Leu Leu Leu Leu Ser Met Gly Gly Thr Trp Ala Ser Lys Glu
            10              15                  20

CCG CTT CGG CCA CGG TGC CGC CCC ATC AAT GCC ACC CTG GCT GTG GAG         149
Pro Leu Arg Pro Arg Cys Arg Pro Ile Asn Ala Thr Leu Ala Val Glu
 25                  30                  35

AAG GAG GGC TGC CCC GTG TGC ATC ACC GTC AAC ACC ACC ATC TGT GCC         197
Lys Glu Gly Cys Pro Val Cys Ile Thr Val Asn Thr Thr Ile Cys Ala
 40              45                  50                  55

GGC TAC TGC CCC ACC ATG ACC CGC GTG CTG CAG GGG GTC CTG CCG GCC         245
Gly Tyr Cys Pro Thr Met Thr Arg Val Leu Gln Gly Val Leu Pro Ala
                 60                  65                  70

CTG CCT CAG GTG GTG TGC AAC TAC CGC GAT GTG CGC TTC GAG TCC ATC         293
Leu Pro Gln Val Val Cys Asn Tyr Arg Asp Val Arg Phe Glu Ser Ile
             75                  80                  85

CGG CTC CCT GGC TGC CCG CGC GGC GTG AAC CCC GTG GTC TCC TAC GCC         341
Arg Leu Pro Gly Cys Pro Arg Gly Val Asn Pro Val Val Ser Tyr Ala
         90                  95                 100

GTG GCT CTC AGC TGT CAA TGT GCA CTC TGC CGC CGC AGC ACC ACT GAC         389
Val Ala Leu Ser Cys Gln Cys Ala Leu Cys Arg Arg Ser Thr Thr Asp
    105                 110                 115

TGC ACT GTG CGA GGC CTG GGG CCC AGC TAC TGC TCC TTT GGT GAA GGA         437
Cys Thr Val Arg Gly Leu Gly Pro Ser Tyr Cys Ser Phe Gly Glu Gly
120                 125                 130                 135

TCC GGT AGC GGA TCT GGT AGC GCT CCT GAT GTG CAG GAT TGC CCA GAA         485
Ser Gly Ser Gly Ser Gly Ser Ala Pro Asp Val Gln Asp Cys Pro Glu
                140                 145                 150

TGC ACG CTA CAG GAA AAC CCA TTC TTC TCC CAG CCG GGT GCC CCA ATA         533
Cys Thr Leu Gln Glu Asn Pro Phe Phe Ser Gln Pro Gly Ala Pro Ile
            155                 160                 165

CTT CAG TGC ATG GGC TGC TGC TTC TCT AGA GCA TAT CCC ACT CCA CTA         581
Leu Gln Cys Met Gly Cys Cys Phe Ser Arg Ala Tyr Pro Thr Pro Leu
        170                 175                 180

AGG TCC AAG AAG ACG ATG TTG GTC CAA AAG AAC GTC ACC TCA GAG TCC         629
Arg Ser Lys Lys Thr Met Leu Val Gln Lys Asn Val Thr Ser Glu Ser
    185                 190                 195

ACT TGC TGT GTA GCT AAA TCA TAT AAC AGG GTC ACA GTA ATG GGG GGT         677
Thr Cys Cys Val Ala Lys Ser Tyr Asn Arg Val Thr Val Met Gly Gly
200                 205                 210                 215

TTC AAA GTG GAG AAC CAC ACG GCG TGC CAC TGC AGT ACT TGT TAT TAT         725
Phe Lys Val Glu Asn His Thr Ala Cys His Cys Ser Thr Cys Tyr Tyr
                220                 225                 230

CAC AAA TCT TAAGGTACC                                                   743
His Lys Ser
```

(2) INFORMATION FOR SEQ ID NO: 21:

(i) SEQUENCE CHARACTERISTICS:
        (A) LENGTH: 234 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 21:

```
Met Glu Met Phe Gln Gly Leu Leu Leu Leu Leu Leu Ser Met Gly
  1               5                  10                 15

Gly Thr Trp Ala Ser Lys Glu Pro Leu Arg Pro Arg Cys Arg Pro Ile
              20                  25                  30

Asn Ala Thr Leu Ala Val Glu Lys Glu Gly Cys Pro Val Cys Ile Thr
              35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
              85                  90                  95

Asn Pro Val Val Ser Tyr Ala Val Ala Leu Ser Cys Gln Cys Ala Leu
             100                 105                 110

Cys Arg Arg Ser Thr Thr Asp Cys Thr Val Arg Gly Leu Gly Pro Ser
             115                 120                 125

Tyr Cys Ser Phe Gly Glu Gly Ser Gly Ser Gly Ser Ala Pro
    130                 135                 140

Asp Val Gln Asp Cys Pro Glu Cys Thr Leu Gln Glu Asn Pro Phe Phe
145                 150                 155                 160

Ser Gln Pro Gly Ala Pro Ile Leu Gln Cys Met Gly Cys Cys Phe Ser
                165                 170                 175

Arg Ala Tyr Pro Thr Pro Leu Arg Ser Lys Lys Thr Met Leu Val Gln
            180                 185                 190

Lys Asn Val Thr Ser Glu Ser Thr Cys Cys Val Ala Lys Ser Tyr Asn
            195                 200                 205

Arg Val Thr Val Met Gly Gly Phe Lys Val Glu Asn His Thr Ala Cys
        210                 215                 220

His Cys Ser Thr Cys Tyr Tyr His Lys Ser
225                 230
```

(2) INFORMATION FOR SEQ ID NO: 22:

(i) SEQUENCE CHARACTERISTICS:
        (A) LENGTH: 717 base pairs
        (B) TYPE: nucleic acid
        (C) STRANDEDNESS: double
        (D) TOPOLOGY: linear (xi) SEQUENCE DESCRIPTION: SEQ ID NO: 22:

```
GGTACCTTAA GATTTGTGAT AATAACAAGT ACTGCAGTGG CACGCCGTGT GGTTCTCCAC      60

TTTGAAACCC CCCATTACTG TGACCCTGTT ATATGATTTA GCTACACAGC AAGTGGACTC     120

TGAGGTGACG TTCTTTTGGA CCAACATCGT CTTCTTGGAC CTTAGTGGAG TGGGATATGC     180

TCTAGAGAAG CAGCAGCCCA TGCACTGAAG TATTGGGGCA CCCGGCTGGG AGAAGAATGG     240

GTTTTCCTGT AGCGTGCATT CTGGGCAATC CTGCACATCA GGAGCGCTAC CAGATCCGCT     300

ACCGGATCCT TCACCAAAGG AGCAGTAGCT GGGCCCAGG  CCTCGCACAG TGCAGTCAGT     360

GGTGCTGCGG CGGCAGAGTG CACATTGACA GCTGAGAGCC ACGGCGTAGG AGACCACGGG     420

GTTCACGCCG CGCGGGCAGC CAGGGAGCCG GATGGACTCG AAGCGCACAT CGCGGTAGTT     480

GCACACCACC TGAGGCAGGG CCGGCAGGAC CCCCTGCAGC ACGCGGGTCA TGGTGGGGCA     540

GTAGCCGGCA CAGATGGTGG TGTTGACGGT GATGCACACG GGCAGCCCT  CCTTCTCCAC     600

AGCCAGGGTG GCATTGATGG GGCGGCACCG TGGCCGAAGC GGCTCCTTGG ATGCCCATGT     660
```

```
CCCGCCCATG CTCAGCAGCA GCAACAGCAG CAGCCCCTGG AACATCTCCA TCCTTGG                    717
```

(2) INFORMATION FOR SEQ ID NO: 23:

(i) SEQUENCE CHARACTERISTICS:
        (A) LENGTH: 743 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 33...734
        (D) OTHER INFORMATION:

(xi) SEQUENCE DESCRIPTION: SEQ ID NO: 23:

```
ATGAAATCGA CGGAATCAGA CTCGAGCCAA GG ATG GAG ATG TTC CAG GGG CTG                  53
                                  Met Glu Met Phe Gln Gly Leu
                                   1               5

CTG CTG TTG CTG CTG CTG AGC ATG GGC GGG ACA TGG GCA TCC AAG GAG                  101
Leu Leu Leu Leu Leu Leu Ser Met Gly Gly Thr Trp Ala Ser Lys Glu
        10                  15                  20

CCG CTT CGG CCA CGG TGC CGC CCC ATC AAT GCC ACC CTG GCT GTG GAG                  149
Pro Leu Arg Pro Arg Cys Arg Pro Ile Asn Ala Thr Leu Ala Val Glu
    25                  30                  35

AAG GAG GGC TGC CCC GTG TGC ATC ACC GTC AAC ACC ACC ATC TGT GCC                  197
Lys Glu Gly Cys Pro Val Cys Ile Thr Val Asn Thr Thr Ile Cys Ala
40                  45                  50                  55

GGC TAC TGC CCC ACC ATG ACC CGC GTG CTG CAG GGG GTC CTG CCG GCC                  245
Gly Tyr Cys Pro Thr Met Thr Arg Val Leu Gln Gly Val Leu Pro Ala
                60                  65                  70

CTG CCT CAG GTG GTG TGC AAC TAC CGC GAT GTG CGC TTC GAG TCC ATC                  293
Leu Pro Gln Val Val Cys Asn Tyr Arg Asp Val Arg Phe Glu Ser Ile
            75                  80                  85

CGG CTC CCT GGC TGC CCG CGC GGC GTG AAC CCC GTG GTC TCC TAC GCC                  341
Arg Leu Pro Gly Cys Pro Arg Gly Val Asn Pro Val Val Ser Tyr Ala
        90                  95                 100

GTG GCT CTC AGC TGT CAA TGT GCA CTC TGC CGC CGC AGC ACC ACT GAC                  389
Val Ala Leu Ser Cys Gln Cys Ala Leu Cys Arg Arg Ser Thr Thr Asp
    105                 110                 115

TGC ACT GTG CGA GGC CTG GGG CCC AGC TAC TGC GAT GAC CCG CGG GGA                  437
Cys Thr Val Arg Gly Leu Gly Pro Ser Tyr Cys Asp Asp Pro Arg Gly
120                 125                 130                 135

TCC GGT AGC GGA TCT GGT AGC GCT CCT GAT GTG CAG GAT TGC CCA GAA                  485
Ser Gly Ser Gly Ser Gly Ser Ala Pro Asp Val Gln Asp Cys Pro Glu
                140                 145                 150

TGC ACG CTA CAG GAA AAC CCA TTC TTC TCC CAG CCG GGT GCC CCA ATA                  533
Cys Thr Leu Gln Glu Asn Pro Phe Phe Ser Gln Pro Gly Ala Pro Ile
            155                 160                 165

CTT CAG TGC ATG GGC TGC TGC TTC TCT AGA GCA TAT CCC ACT CCA CTA                  581
Leu Gln Cys Met Gly Cys Cys Phe Ser Arg Ala Tyr Pro Thr Pro Leu
        170                 175                 180

AGG TCC AAG AAG ACG ATG TTG GTC CAA AAG AAC GTC ACC TCA GAG TCC                  629
Arg Ser Lys Lys Thr Met Leu Val Gln Lys Asn Val Thr Ser Glu Ser
    185                 190                 195

ACT TGC TGT GTA GCT AAA TCA TAT AAC AGG GTC ACA GTA ATG GGG GGT                  677
Thr Cys Cys Val Ala Lys Ser Tyr Asn Arg Val Thr Val Met Gly Gly
200                 205                 210                 215

TTC AAA GTG GAG AAC CAC ACG GCG TGC CAC TGC AGT ACT TGT TAT TAT                  725
Phe Lys Val Glu Asn His Thr Ala Cys His Cys Ser Thr Cys Tyr Tyr
                220                 225                 230

CAC AAA TCT TAAGGTACC                                                            743
His Lys Ser
```

(2) INFORMATION FOR SEQ ID NO: 24:

(i) SEQUENCE CHARACTERISTICS:
        (A) LENGTH: 234 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 24:

```
His Lys Ser

Met Glu Met Phe Gln Gly Leu Leu Leu Leu Leu Leu Ser Met Gly
  1               5                  10                  15

Gly Thr Trp Ala Ser Lys Glu Pro Leu Arg Pro Arg Cys Arg Pro Ile
                 20                  25                  30

Asn Ala Thr Leu Ala Val Glu Lys Glu Gly Cys Pro Val Cys Ile Thr
                 35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
                100                 105                 110

Cys Arg Arg Ser Thr Thr Asp Cys Thr Val Arg Gly Leu Gly Pro Ser
                115                 120                 125

Tyr Cys Asp Asp Pro Arg Gly Ser Gly Ser Gly Ser Gly Ser Ala Pro
130                 135                 140

Asp Val Gln Asp Cys Pro Glu Cys Thr Leu Gln Glu Asn Pro Phe Phe
145                 150                 155                 160

Ser Gln Pro Gly Ala Pro Ile Leu Gln Cys Met Gly Cys Cys Phe Ser
                165                 170                 175

Arg Ala Tyr Pro Thr Pro Leu Arg Ser Lys Lys Thr Met Leu Val Gln
                180                 185                 190

Lys Asn Val Thr Ser Glu Ser Thr Cys Cys Val Ala Lys Ser Tyr Asn
                195                 200                 205

Arg Val Thr Val Met Gly Gly Phe Lys Val Glu Asn His Thr Ala Cys
                210                 215                 220

His Cys Ser Thr Cys Tyr Tyr His Lys Ser
225                 230
```

(2) INFORMATION FOR SEQ ID NO: 25:

(i) SEQUENCE CHARACTERISTICS:
        (A) LENGTH: 717 base pairs
        (B) TYPE: nucleic acid
        (C) STRANDEDNESS: double
        (D) TOPOLOGY: linear (xi) SEQUENCE DESCRIPTION: SEQ ID NO: 25:

```
GGTACCTTAA GATTTGTGAT AATAACAAGT ACTGCAGTGG CACGCCGTGT GGTTCTCCAC    60
TTTGAAACCC CCCATTACTG TGACCCTGTT ATATGATTTA GCTACACAGC AAGTGGACTC   120
TGAGGTGACG TTCTTTTGGA CCAACATCGT CTTCTTGGAC CTTAGTGGAG TGGGATATGC   180
```

-continued

```
TCTAGAGAAG CAGCAGCCCA TGCACTGAAG TATTGGGGCA CCCGGCTGGG AGAAGAATGG    240

GTTTTCCTGT AGCGTGCATT CTGGGCAATC CTGCACATCA GGAGCGCTAC CAGATCCGCT    300

ACCGGATCCC CGCGGGTCAT CGCAGTAGCT GGGCCCCAGG CCTCGCACAG TGCAGTCAGT    360

GGTGCTGCGG CGGCAGAGTG CACATTGACA GCTGAGAGCC ACGGCGTAGG AGACCACGGG    420

GTTCACGCCG CGCGGGCAGC CAGGGAGCCG GATGGACTCG AAGCGCACAT CGCGGTAGTT    480

GCACACCACC TGAGGCAGGG CCGGCAGGAC CCCCTGCAGC ACGCGGGTCA TGGTGGGGCA    540

GTAGCCGGCA CAGATGGTGG TGTTGACGGT GATGCACACG GGGCAGCCCT CCTTCTCCAC    600

AGCCAGGGTG GCATTGATGG GGCGGCACCG TGGCCGAAGC GGCTCCTTGG ATGCCCATGT    660

CCCGCCCATG CTCAGCAGCA GCAACAGCAG CAGCCCCTGG AACATCTCCA TCCTTGG      717
```

(2) INFORMATION FOR SEQ ID NO: 26:

(i) SEQUENCE CHARACTERISTICS:
        (A) LENGTH: 719 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 33...700
        (D) OTHER INFORMATION:

(xi) SEQUENCE DESCRIPTION: SEQ ID NO: 26:

```
ATGAAATCGA CGGAATCAGA CTCGAGCCAA GG ATG AAG ACA CTC CAG TTT TTC     53
                                   Met Lys Thr Leu Gln Phe Phe
                                    1               5

TTC CTT TTC TGT TGC TGG AAA GCA ATC TGC TGC AAT AGC TGT GAG CTG    101
Phe Leu Phe Cys Cys Trp Lys Ala Ile Cys Cys Asn Ser Cys Glu Leu
        10                  15                  20

ACC AAC ATC ACC ATT GCA ATA GAG AAA GAA GAA TGT CGT TTC TGC ATA    149
Thr Asn Ile Thr Ile Ala Ile Glu Lys Glu Glu Cys Arg Phe Cys Ile
    25                  30                  35

AGC ATC AAC ACC ACT TGG TGT GCT GGC TAC TGC TAC ACC AGG GAT CTG    197
Ser Ile Asn Thr Thr Trp Cys Ala Gly Tyr Cys Tyr Thr Arg Asp Leu
40                  45                  50                  55

GTG TAT AAG GAC CCA GCC AGG CCC AAA ATC CAG AAA ACA TGT ACC TTC    245
Val Tyr Lys Asp Pro Ala Arg Pro Lys Ile Gln Lys Thr Cys Thr Phe
            60                  65                  70

AAG GAA CTG GTA TAT GAA ACA GTG AGA GTG CCC GGC TGT GCT CAC CAT    293
Lys Glu Leu Val Tyr Glu Thr Val Arg Val Pro Gly Cys Ala His His
                75                  80                  85

GCA GAT TCC TTG TAT ACA TAC CCA GTG GCC ACC CAG TGT CAC TGT GGC    341
Ala Asp Ser Leu Tyr Thr Tyr Pro Val Ala Thr Gln Cys His Cys Gly
            90                  95                 100

AAG TGT GAC AGC GAC AGC ACT GAT TGT ACT GTG CGA GGC CTG GGG CCC    389
Lys Cys Asp Ser Asp Ser Thr Asp Cys Thr Val Arg Gly Leu Gly Pro
        105                 110                 115

AGC TAC TGC TCC TTT GGT GAA GGA TCC GGT AGC GGA TCT GGT AGC GCT    437
Ser Tyr Cys Ser Phe Gly Glu Gly Ser Gly Ser Gly Ser Gly Ser Ala
120                 125                 130                 135

CCT GAT GTG CAG GAT TGC CCA GAA TGC ACG CTA CAG GAA AAC CCA TTC    485
Pro Asp Val Gln Asp Cys Pro Glu Cys Thr Leu Gln Glu Asn Pro Phe
                140                 145                 150

TTC TCC CAG CCG GGT GCC CCA ATA CTT CAG TGC ATG GGC TGC TGC TTC    533
Phe Ser Gln Pro Gly Ala Pro Ile Leu Gln Cys Met Gly Cys Cys Phe
            155                 160                 165

TCT AGA GCA TAT CCC ACT CCA CTA AGG TCC AAG AAG ACG ATG TTG GTC    581
```

```
Ser Arg Ala Tyr Pro Thr Pro Leu Arg Ser Lys Lys Thr Met Leu Val
        170                 175                 180

CAA AAG AAC GTC ACC TCA GAG TCC ACT TGC TGT GTA GCT AAA TCA TAT     629
Gln Lys Asn Val Thr Ser Glu Ser Thr Cys Cys Val Ala Lys Ser Tyr
185                 190                 195

AAC AGG GTC ACA GTA ATG GGG GGT TTC AAA GTG GAG AAC CAC ACG GCG     677
Asn Arg Val Thr Val Met Gly Gly Phe Lys Val Glu Asn His Thr Ala
200                 205                 210                 215

TGC CAC TGC AGT ACT TGT TAT TA TCACAAATCT TAAGGTACC                 719
Cys His Cys Ser Thr Cys Tyr Tyr
                220
```

(2) INFORMATION FOR SEQ ID NO: 27:

(i) SEQUENCE CHARACTERISTICS:
        (A) LENGTH: 223 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 27:

```
Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
                20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
                100                 105                 110

Thr Val Arg Gly Leu Gly Pro Ser Tyr Cys Ser Phe Gly Glu Gly Ser
            115                 120                 125

Gly Ser Gly Ser Gly Ser Ala Pro Asp Val Gln Asp Cys Pro Glu Cys
        130                 135                 140

Thr Leu Gln Glu Asn Pro Phe Phe Ser Gln Pro Gly Ala Pro Ile Leu
145                 150                 155                 160

Gln Cys Met Gly Cys Cys Phe Ser Arg Ala Tyr Pro Thr Pro Leu Arg
                165                 170                 175

Ser Lys Lys Thr Met Leu Val Gln Lys Asn Val Thr Ser Glu Ser Thr
            180                 185                 190

Cys Cys Val Ala Lys Ser Tyr Asn Arg Val Thr Val Met Gly Gly Phe
                195                 200                 205

Lys Val Glu Asn His Thr Ala Cys His Cys Ser Thr Cys Tyr Tyr
    210                 215                 220
```

(2) INFORMATION FOR SEQ ID NO: 28:

(i) SEQUENCE CHARACTERISTICS:
        (A) LENGTH: 693 base pairs
        (B) TYPE: nucleic acid
        (C) STRANDEDNESS: double -continued (D) TOPOLOGY: linear (xi) SEQUENCE DESCRIPTION: SEQ ID NO: 28:

```
GGTACCTTAA GATTTGTGAT AATAACAAGT ACTGCAGTGG CACGCCGTGT GGTTCTCCAC      60

TTTGAAACCC CCCATTACTG TGACCCTGTT ATATGATTTA GCTACACAGC AAGTGGACTC     120

TGAGGTGACG TTCTTTTGGA CCAACATCGT CTTCTTGGAC CTTAGTGGAG TGGGATATGC     180

TCTAGAGAAG CAGCAGCCCA TGCACTGAAG TATTGGGCA CCCGGCTGGG AGAAGAATGG      240

GTTTTCCTGT AGCGTGCATT CTGGGCAATC CTGCACATCA GGAGCGCTAC CAGATCCGCT     300

ACCGGATCCT TCACCAAAGG AGCAGTAGCT GGGCCCCAGG CCTCGCACAG TACAATCAGT     360

GCTGTCGCTG TCACACTTGC CACAGTGACA CTGGGTGGCC ACTGGGTATG TATACAAGGA     420

ATCTGCATGG TGAGCACAGC CGGGCACTCT CACTGTTTCA TATACCAGTT CCTTGAAGGT     480

ACATGTTTTC TGGATTTTGG GCCTGGCTGG GTCCTTATAC ACCAGATCCC TGGTGTAGCA     540

GTAGCCAGCA CACCAAGTGG TGTTGATGCT TATGCAGAAA CGACATTCTT CTTTCTCTAT     600

TGCAATGGTG ATGTTGGTCA GCTCACAGCT ATTGCAGCAG ATTGCTTTCC AGCAACAGAA     660

AAGGAAGAAA AACTGGAGTG TCTTCATCCT TGG                                  693
```

(2) INFORMATION FOR SEQ ID NO: 29:

(i) SEQUENCE CHARACTERISTICS:
        (A) LENGTH: 707 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 33...698
        (D) OTHER INFORMATION:

(xi) SEQUENCE DESCRIPTION: SEQ ID NO: 29:

```
ATGAAATCGA CGGAATCAGA CTCGAGCCAA GG ATG AAG ACA CTC CAG TTT TTC       53
                                   Met Lys Thr Leu Gln Phe Phe
                                    1               5

TTC CTT TTC TGT TGC TGG AAA GCA ATC TGC TGC AAT AGC TGT GAG CTG      101
Phe Leu Phe Cys Cys Trp Lys Ala Ile Cys Cys Asn Ser Cys Glu Leu
         10              15                  20

ACC AAC ATC ACC ATT GCA ATA GAG AAA GAA GAA TGT CGT TTC TGC ATA      149
Thr Asn Ile Thr Ile Ala Ile Glu Lys Glu Glu Cys Arg Phe Cys Ile
     25                  30                  35

AGC ATC AAC ACC ACT TGG TGT GCT GGC TAC TGC TAC ACC AGG GAT CTG      197
Ser Ile Asn Thr Thr Trp Cys Ala Gly Tyr Cys Tyr Thr Arg Asp Leu
40                  45                  50                  55

GTG TAT AAG GAC CCA GCC AGG CCC AAA ATC CAG AAA ACA TGT ACC TTC      245
Val Tyr Lys Asp Pro Ala Arg Pro Lys Ile Gln Lys Thr Cys Thr Phe
                 60                  65                  70

AAG GAA CTG GTA TAT GAA ACA GTG AGA GTG CCC GGC TGT GCT CAC CAT      293
Lys Glu Leu Val Tyr Glu Thr Val Arg Val Pro Gly Cys Ala His His
             75                  80                  85

GCA GAT TCC TTG TAT ACA TAC CCA GTG GCC ACC CAG TGT CAC TGT GGC      341
Ala Asp Ser Leu Tyr Thr Tyr Pro Val Ala Thr Gln Cys His Cys Gly
         90                  95                 100

AAG TGT GAC AGC GAC AGC ACT GAT TGT ACT GTG CGA GGC CTG GGG CCC      389
Lys Cys Asp Ser Asp Ser Thr Asp Cys Thr Val Arg Gly Leu Gly Pro
     105                 110                 115

AGC TAC TGC GGA TCC GGT AGC GGA TCT GGT AGC GCT CCT GAT GTG CAG      437
Ser Tyr Cys Gly Ser Gly Ser Gly Ser Gly Ser Ala Pro Asp Val Gln
120                 125                 130                 135
```

```
GAT TGC CCA GAA TGC ACG CTA CAG GAA AAC CCA TTC TTC TCC CAG CCG      485
Asp Cys Pro Glu Cys Thr Leu Gln Glu Asn Pro Phe Phe Ser Gln Pro
            140                 145                 150

GGT GCC CCA ATA CTT CAG TGC ATG GGC TGC TGC TTC TCT AGA GCA TAT      533
Gly Ala Pro Ile Leu Gln Cys Met Gly Cys Cys Phe Ser Arg Ala Tyr
            155                 160                 165

CCC ACT CCA CTA AGG TCC AAG AAG ACG ATG TTG GTC CAA AAG AAC GTC      581
Pro Thr Pro Leu Arg Ser Lys Lys Thr Met Leu Val Gln Lys Asn Val
            170                 175                 180

ACC TCA GAG TCC ACT TGC TGT GTA GCT AAA TCA TAT AAC AGG GTC ACA      629
Thr Ser Glu Ser Thr Cys Cys Val Ala Lys Ser Tyr Asn Arg Val Thr
            185                 190                 195

GTA ATG GGG GGT TTC AAA GTG GAG AAC CAC ACG GCG TGC CAC TGC AGT      677
Val Met Gly Gly Phe Lys Val Glu Asn His Thr Ala Cys His Cys Ser
200             205                 210                 215

ACT TGT TAT TAT CAC AAA TCT TAAGGTACC                                707
Thr Cys Tyr Tyr His Lys Ser
                220
```

(2) INFORMATION FOR SEQ ID NO: 30:

(i) SEQUENCE CHARACTERISTICS:
        (A) LENGTH: 222 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 30:

```
Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
                20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Gly Ser Gly Ser Gly Ser
            115                 120                 125

Gly Ser Ala Pro Asp Val Gln Asp Cys Pro Glu Cys Thr Leu Gln Glu
    130                 135                 140

Asn Pro Phe Phe Ser Gln Pro Gly Ala Pro Ile Leu Gln Cys Met Gly
145                 150                 155                 160

Cys Cys Phe Ser Arg Ala Tyr Pro Thr Pro Leu Arg Ser Lys Lys Thr
                165                 170                 175

Met Leu Val Gln Lys Asn Val Thr Ser Glu Ser Thr Cys Cys Val Ala
            180                 185                 190

Lys Ser Tyr Asn Arg Val Thr Val Met Gly Gly Phe Lys Val Glu Asn
    195                 200                 205
```

```
His Thr Ala Cys His Cys Ser Thr Cys Tyr Tyr His Lys Ser
    210                 215                 220
```

(2) INFORMATION FOR SEQ ID NO: 31:

(i) SEQUENCE CHARACTERISTICS:
        (A) LENGTH: 681 base pairs
        (B) TYPE: nucleic acid
        (C) STRANDEDNESS: double
        (D) TOPOLOGY: linear (xi) SEQUENCE DESCRIPTION: SEQ ID NO: 31:

```
GGTACCTTAA GATTTGTGAT AATAACAAGT ACTGCAGTGG CACGCCGTGT GGTTCTCCAC      60

TTTGAAACCC CCCATTACTG TGACCCTGTT ATATGATTTA GCTACACAGC AAGTGGACTC     120

TGAGGTGACG TTCTTTTGGA CCAACATCGT CTTCTTGGAC CTTAGTGGAG TGGGATATGC     180

TCTAGAGAAG CAGCAGCCCA TGCACTGAAG TATTGGGGCA CCCGGCTGGG AGAAGAATGG     240

GTTTTCCTGT AGCGTGCATT CTGGGCAATC CTGCACATCA GGAGCGCTAC CAGATCCGCT     300

ACCGGATCCG CAGTAGCTGG GCCCCAGGCC TCGCACAGTA CAATCAGTGC TGTCGCTGTC     360

ACACTTGCCA CAGTGACACT GGGTGGCCAC TGGGTATGTA TACAAGGAAT CTGCATGGTG     420

AGCACAGCCG GGCACTCTCA CTGTTTCATA TACCAGTTCC TTGAAGGTAC ATGTTTTCTG     480

GATTTTGGGC CTGGCTGGGT CCTTATACAC CAGATCCCTG GTGTAGCAGT AGCCAGCACA     540

CCAAGTGGTG TTGATGCTTA TGCAGAAACG ACATTCTTCT TTCTCTATTG CAATGGTGAT     600

GTTGGTCAGC TCACAGCTAT TGCAGCAGAT TGCTTTCCAG CAACAGAAAA GGAAGAAAAA     660

CTGGAGTGTC TTCATCCTTG G                                              681
```

(2) INFORMATION FOR SEQ ID NO: 32:

(i) SEQUENCE CHARACTERISTICS:
        (A) LENGTH: 312 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 1...303
        (D) OTHER INFORMATION:

(xi) SEQUENCE DESCRIPTION: SEQ ID NO: 32:

```
TGC GGA TCC GGT AGC GGA TCT GGT AGC GCT CCT GAT GTG CAG GAT TGC       48
Cys Gly Ser Gly Ser Gly Ser Gly Ser Ala Pro Asp Val Gln Asp Cys
 1               5                  10                  15

CCA GAA TGC ACG CTA CAG GAA AAC CCA TTC TTC TCC CAG CCG GGT GCC       96
Pro Glu Cys Thr Leu Gln Glu Asn Pro Phe Phe Ser Gln Pro Gly Ala
            20                  25                  30

CCA ATA CTT CAG TGC ATG GGC TGC TGC TTC TCT AGA GCA TAT CCC ACT      144
Pro Ile Leu Gln Cys Met Gly Cys Cys Phe Ser Arg Ala Tyr Pro Thr
        35                  40                  45

CCA CTA AGG TCC AAG AAG ACG ATG TTG GTC CAA AAG CAA GTC ACC TCA      192
Pro Leu Arg Ser Lys Lys Thr Met Leu Val Gln Lys Gln Val Thr Ser
    50                  55                  60

GAG TCC ACT TGC TGT GTA GCT AAA TCA TAT AAC AGG GTC ACA GTA ATG      240
Glu Ser Thr Cys Cys Val Ala Lys Ser Tyr Asn Arg Val Thr Val Met
65                  70                  75                  80

GGG GGT TTC AAA GTG GAG CAA CAC ACG GCG TGC CAC TGC AGT ACT TGT      288
Gly Gly Phe Lys Val Glu Gln His Thr Ala Cys His Cys Ser Thr Cys
                85                  90                  95

TAT TAT CAC AAA TCT TAAGGTACC                                        312
```

```
Tyr Tyr His Lys Ser
            100

(2) INFORMATION FOR SEQ ID NO: 33:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 33:

Cys Gly Ser Gly Ser Gly Ser Gly Ser Ala Pro Asp Val Gln Asp Cys
 1               5                  10                  15

Pro Glu Cys Thr Leu Gln Glu Asn Pro Phe Phe Ser Gln Pro Gly Ala
            20                  25                  30

Pro Ile Leu Gln Cys Met Gly Cys Cys Phe Ser Arg Ala Tyr Pro Thr
            35                  40                  45

Pro Leu Arg Ser Lys Lys Thr Met Leu Val Gln Lys Gln Val Thr Ser
 50                  55                  60

Glu Ser Thr Cys Cys Val Ala Lys Ser Tyr Asn Arg Val Thr Val Met
 65                  70                  75                  80

Gly Gly Phe Lys Val Glu Gln His Thr Ala Cys His Cys Ser Thr Cys
                85                  90                  95

Tyr Tyr His Lys Ser
            100

(2) INFORMATION FOR SEQ ID NO: 34:

(i) SEQUENCE CHARACTERISTICS:
        (A) LENGTH: 317 base pairs
        (B) TYPE: nucleic acid
        (C) STRANDEDNESS: double
        (D) TOPOLOGY: linear (xi) SEQUENCE DESCRIPTION: SEQ ID NO: 34:

GTACCGGTAC CTTAAGATTT GTGATAATAA CAAGTACTGC AGTGGCACGC CGTGTGTTGC      60

TCCACTTTGA AACCCCCCAT TACTGTGACC CTGTTATATG ATTTAGCTAC ACAGCAAGTG     120

GACTCTGAGG TGACTTGCTT TTGGACCAAC ATCGTCTTCT TGGACCTTAG TGGAGTGGGA     180

TATGCTCTAG AGAAGCAGCA GCCCATGCAC TGAAGTATTG GGGCACCCGG CTGGGAGAAG     240

AATGGGTTTT CCTGTAGCGT GCATTCTGGG CAATCCTGCA CATCAGGAGC GCTACCAGAT     300

CCGCTACCGG ATCCGCA                                                    317

(2) INFORMATION FOR SEQ ID NO: 35:

(i) SEQUENCE CHARACTERISTICS:
        (A) LENGTH: 575 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 33...575
        (D) OTHER INFORMATION:

(xi) SEQUENCE DESCRIPTION: SEQ ID NO: 35:

ATGAAATCGA CGGAATCAGA CTCGAGCCAA GG ATG GAG ATG TTC CAG GGG CTG        53
```

```
                              Met Glu Met Phe Gln Gly Leu
                                1           5
CTG CTG TTG CTG CTG CTG AGC ATG GGC GGG ACA TGG GCA TCC AAG GAG        101
Leu Leu Leu Leu Leu Leu Ser Met Gly Gly Thr Trp Ala Ser Lys Glu
            10                  15                  20

CCG CTT CGG CCA CGG TGC CGC CCC ATC CAA GCC ACC CTG GCT GTG GAG        149
Pro Leu Arg Pro Arg Cys Arg Pro Ile Gln Ala Thr Leu Ala Val Glu
        25                  30                  35

AAG GAG GGC TGC CCC GTG TGC ATC ACC GTC AAC ACC ACC ATC TGT GCC        197
Lys Glu Gly Cys Pro Val Cys Ile Thr Val Asn Thr Thr Ile Cys Ala
40                  45                  50                  55

GGC TAC TGC CCC ACC ATG ACC CGC GTG CTG CAG GGG GTC CTG CCG GCC        245
Gly Tyr Cys Pro Thr Met Thr Arg Val Leu Gln Gly Val Leu Pro Ala
                60                  65                  70

CTG CCT CAG GTG GTG TGC AAC TAC CGC GAT GTG CGC TTC GAG TCC ATC        293
Leu Pro Gln Val Val Cys Asn Tyr Arg Asp Val Arg Phe Glu Ser Ile
            75                  80                  85

CGG CTC CCT GGC TGC CCG CGC GGC GTG AAC CCC GTG GTC TCC TAC GCC        341
Arg Leu Pro Gly Cys Pro Arg Gly Val Asn Pro Val Val Ser Tyr Ala
        90                  95                  100

GTG GCT CTC AGC TGT CAA TGT GCA CTC TGC CGC CGC AGC ACC ACT GAC        389
Val Ala Leu Ser Cys Gln Cys Ala Leu Cys Arg Arg Ser Thr Thr Asp
105                 110                 115

TGC GGG GGT CCC AAG GAC CAC CCC TTG ACC TGT GAT GAC CCC CGC TTC        437
Cys Gly Gly Pro Lys Asp His Pro Leu Thr Cys Asp Asp Pro Arg Phe
120                 125                 130                 135

CAG GAC TCC TCT TCC TCA AAG GCC CCT CCC CCC AGC CTT CCA AGC CCA        485
Gln Asp Ser Ser Ser Ser Lys Ala Pro Pro Pro Ser Leu Pro Ser Pro
                140                 145                 150

TCC CGA CTC CCG GGG CCC TCG GAC ACC CCG ATC CTC CCC CAA GGA TCC        533
Ser Arg Leu Pro Gly Pro Ser Asp Thr Pro Ile Leu Pro Gln Gly Ser
            155                 160                 165

GGT AGC GGA TCT GGT AGC GCT CCT GAT GTG CAG GAT TGC CCA                575
Gly Ser Gly Ser Gly Ser Ala Pro Asp Val Gln Asp Cys Pro
        170                 175                 180

(2) INFORMATION FOR SEQ ID NO: 36:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 36:

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
                20                  25                  30

Gln Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
        50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95
```

```
Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln Gly Ser Gly Ser Gly Ser Gly Ser Ala Pro Asp
                165                 170                 175

Val Gln Asp Cys Pro
                180
```

(2) INFORMATION FOR SEQ ID NO: 37:

(i) SEQUENCE CHARACTERISTICS:
        (A) LENGTH: 549 base pairs
        (B) TYPE: nucleic acid
        (C) STRANDEDNESS: double
        (D) TOPOLOGY: linear (xi) SEQUENCE DESCRIPTION: SEQ ID NO: 37:

```
TGGGCAATCC TGCACATCAG GAGCGCTACC AGATCCGCTA CCGGATCCTT GGGGGAGGAT      60

CGGGGTGTCC GAGGGCCCCG GGAGTCGGGA TGGGCTTGGA AGGCTGGGGG GAGGGGCCTT     120

TGAGGAAGAG GAGTCCTGGA AGCGGGGGTC ATCACAGGTC AAGGGGTGGT CCTTGGGACC     180

CCCGCAGTCA GTGGTGCTGC GGCGGCAGAG TGCACATTGA CAGCTGAGAG CCACGGCGTA     240

GGAGACCACG GGGTTCACGC CGCGCGGGCA GCCAGGGAGC CGGATGGACT CGAAGCGCAC     300

ATCGCGGTAG TTGCACACCA CCTGAGGCAG GGCCGGCAGG ACCCCCTGCA GCACGCGGGT     360

CATGGTGGGG CAGTAGCCGG CACAGATGGT GGTGTTGACG GTGATGCACA CGGGGCAGCC     420

CTCCTTCTCC ACAGCCAGGG TGGCTTGGAT GGGGCGGCAC CGTGGCCGAA GCGGCTCCTT     480

GGATGCCCAT GTCCCGCCCA TGCTCAGCAG CAGCAACAGC AGCAGCCCCT GGAACATCTC     540

CATCCTTGG                                                             549
```

(2) INFORMATION FOR SEQ ID NO: 38:

(i) SEQUENCE CHARACTERISTICS:
        (A) LENGTH: 837 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 33...827
        (D) OTHER INFORMATION:

(xi) SEQUENCE DESCRIPTION: SEQ ID NO: 38:

```
ATGAAATCGA CGGAATCAGA CTCGAGCCAA GG ATG GAG ATG TTC CAG GGG CTG        53
                                    Met Glu Met Phe Gln Gly Leu
                                     1               5

CTG CTG TTG CTG CTG CTG AGC ATG GGC GGG ACA TGG GCA TCC AAG GAG       101
Leu Leu Leu Leu Leu Leu Ser Met Gly Gly Thr Trp Ala Ser Lys Glu
         10                  15                  20

CCG CTT CGG CCA CGG TGC CGC CCC ATC AAT GCC ACC CTG GCT GTG GAG       149
Pro Leu Arg Pro Arg Cys Arg Pro Ile Asn Ala Thr Leu Ala Val Glu
     25                  30                  35

AAG GAG GGC TGC CCC GTG TGC ATC ACC GTC AAC ACC ACC ATC TGT GCC       197
```

```
Lys Glu Gly Cys Pro Val Cys Ile Thr Val Asn Thr Thr Ile Cys Ala
 40              45                  50                  55

GGC TAC TGC CCC ACC ATG ACC CGC GTG CTG CAG GGG GTC CTG CCG GCC      245
Gly Tyr Cys Pro Thr Met Thr Arg Val Leu Gln Gly Val Leu Pro Ala
             60                  65                  70

CTG CCT CAG GTG GTG TGC AAC TAC CGC GAT GTG CGC TTC GAG TCC ATC      293
Leu Pro Gln Val Val Cys Asn Tyr Arg Asp Val Arg Phe Glu Ser Ile
         75                  80                  85

CGG CTC CCT GGC TGC CCG CGC GGC GTG AAC CCC GTG GTC TCC TAC GCC      341
Arg Leu Pro Gly Cys Pro Arg Gly Val Asn Pro Val Val Ser Tyr Ala
             90                  95                 100

GTG GCT CTC AGC TGT CAA TGT GCA CTC TGC CGC CGC AGC ACC ACT GAC      389
Val Ala Leu Ser Cys Gln Cys Ala Leu Cys Arg Arg Ser Thr Thr Asp
        105                 110                 115

TGC GGG GGT CCC AAG GAC CAC CCC TTG ACC TGT GAT GAC CCC CGC TTC      437
Cys Gly Gly Pro Lys Asp His Pro Leu Thr Cys Asp Asp Pro Arg Phe
120                 125                 130                 135

CAG GAC TCC TCT TCC TCA AAG GCC CCT CCC CCC AGC CTT CCA AGC CCA      485
Gln Asp Ser Ser Ser Ser Lys Ala Pro Pro Pro Ser Leu Pro Ser Pro
                140                 145                 150

TCC CGA CTC CCG GGG CCC TCG GAC ACC CCG ATC CTC CCC CAA GGA TCC      533
Ser Arg Leu Pro Gly Pro Ser Asp Thr Pro Ile Leu Pro Gln Gly Ser
            155                 160                 165

GGT AGC GGA TCT GGT AGC GCT CCT GAT GTG CAG GAT TGC CCA GAA TGC      581
Gly Ser Gly Ser Gly Ser Ala Pro Asp Val Gln Asp Cys Pro Glu Cys
        170                 175                 180

ACG CTA CAG GAA AAC CCA TTC TTC TCC CAG CCG GGT GCC CCA ATA CTT      629
Thr Leu Gln Glu Asn Pro Phe Phe Ser Gln Pro Gly Ala Pro Ile Leu
185                 190                 195

CAG TGC ATG GGC TGC TGC TTC TCT AGA GCA TAT CCC ACT CCA CTA AGG      677
Gln Cys Met Gly Cys Cys Phe Ser Arg Ala Tyr Pro Thr Pro Leu Arg
200                 205                 210                 215

TCC AAG AAG ACG ATG TTG GTC CAA AAG CAA GTC ACC TCA GAG TCC ACT      725
Ser Lys Lys Thr Met Leu Val Gln Lys Gln Val Thr Ser Glu Ser Thr
                220                 225                 230

TGC TGT GTA GCT AAA TCA TAT AAC AGG GTC ACA GTA ATG GGG GGT TTC      773
Cys Cys Val Ala Lys Ser Tyr Asn Arg Val Thr Val Met Gly Gly Phe
            235                 240                 245

AAA GTG GAG CAA CAC ACG GCG TGC CAC TGC AGT ACT TGT TAT TAT CAC      821
Lys Val Glu Gln His Thr Ala Cys His Cys Ser Thr Cys Tyr Tyr His
        250                 255                 260

AAA TCT TAAGTTAACC                                                   837
Lys Ser
    265

(2) INFORMATION FOR SEQ ID NO: 39:

(i) SEQUENCE CHARACTERISTICS:
        (A) LENGTH: 265 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 39:

Met Glu Met Phe Gln Gly Leu Leu Leu Leu Leu Leu Ser Met Gly
  1               5                  10                  15

Gly Thr Trp Ala Ser Lys Glu Pro Leu Arg Pro Arg Cys Arg Pro Ile
             20                  25                  30
```

```
Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln Gly Ser Gly Ser Gly Ser Ala Pro Asp
                165                 170                 175

Val Gln Asp Cys Pro Glu Cys Thr Leu Gln Glu Asn Pro Phe Phe Ser
            180                 185                 190

Gln Pro Gly Ala Pro Ile Leu Gln Cys Met Gly Cys Cys Phe Ser Arg
            195                 200                 205

Ala Tyr Pro Thr Pro Leu Arg Ser Lys Lys Thr Met Leu Val Gln Lys
            210                 215                 220

Gln Val Thr Ser Glu Ser Thr Cys Cys Val Ala Lys Ser Tyr Asn Arg
225                 230                 235                 240

Val Thr Val Met Gly Gly Phe Lys Val Glu Gln His Thr Ala Cys His
                245                 250                 255

Cys Ser Thr Cys Tyr Tyr His Lys Ser
            260                 265

(2) INFORMATION FOR SEQ ID NO: 40:

(i) SEQUENCE CHARACTERISTICS:
        (A) LENGTH: 835 base pairs
        (B) TYPE: nucleic acid
        (C) STRANDEDNESS: double
        (D) TOPOLOGY: linear (xi) SEQUENCE DESCRIPTION: SEQ ID NO: 40:

TCCGGATTAG CTTGAGATGG ATCCGGTTAA CTTAAGATTT GTGATAATAA CAAGTACTGC      60

AGTGGCACGC CGTGTGTTGC TCCACTTTGA AACCCCCCAT TACTGTGACC CTGTTATATG    120

ATTTAGCTAC ACAGCAAGTG GACTCTGAGG TGACTTGCTT TTGGACCAAC ATCGTCTTCT    180

TGGACCTTAG TGGAGTGGGA TATGCTCTAG AGAAGCAGCA GCCCATGCAC TGAAGTATTG    240

GGGCACCCGG CTGGGAGAAG AATGGGTTTT CCTGTAGCGT GCATTCTGGG CAATCCTGCA    300

CATCAGGAGC GCTACCAGAT CCGCTACCGG ATCCTTGGGG GAGGATCGGG GTGTCCGAGG    360

GCCCCGGGAG TCGGGATGGG CTTGGAAGGC TGGGGGAGG GGCCTTTGAG GAAGAGGAGT    420

CCTGGAAGCG GGGGTCATCA CAGGTCAAGG GGTGGTCCTT GGACCCCCG CAGTCAGTGG    480

TGCTGCGGCG GCAGAGTGCA CATTGACAGC TGAGAGCCAC GGCGTAGGAG ACCACGGGGT    540

TCACGCCGCG CGGGCAGCCA GGGAGCCGGA TGGACTCGAA GCGCACATCG CGGTAGTTGC    600

ACACCACCTG AGGCAGGGCC GGCAGGACCC CCTGCAGCAC GCGGGTCATG GTGGGCAGT    660
```

| | |
|---|---|
| AGCCGGCACA GATGGTGGTG TTGACGGTGA TGCACACGGG GCAGCCCTCC TTCTCCACAG | 720 |
| CCAGGGTGGC ATTGATGGGG CGGCACCGTG GCCGAAGCGG CTCCTTGGAT GCCCATGTCC | 780 |
| CGCCCATGCT CAGCAGCAGC AACAGCAGCA GCCCCTGGAA CATCTCCATC CTTGG | 835 |

(2) INFORMATION FOR SEQ ID NO: 41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 41:

| | |
|---|---|
| GGAGGAAGGG TGGTCGACCT CTCTGGT | 27 |

(2) INFORMATION FOR SEQ ID NO: 42:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 42:

| | |
|---|---|
| CACATCAGGA GCTTGTGGGA GGATCGG | 27 |

(2) INFORMATION FOR SEQ ID NO: 43:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 43:

| | |
|---|---|
| ATCCTCCCAC AAGCTCCTGA TGTGCAG | 27 |

(2) INFORMATION FOR SEQ ID NO: 44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 44:

| | |
|---|---|
| TGAGTCGACA TGATAATTCA GTGATTGAAT | 30 |

(2) INFORMATION FOR SEQ ID NO: 45:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO: 45:

| | |
|---|---|
| ATGAAATCGA CGGAATCAGA CTCGAGCCAA GGATGGAGAT GTTCCAGGGG CTGCT | 55 |

(2) INFORMATION FOR SEQ ID NO: 46:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO: 46:

GCTACCAGAT CCGCTACCGG ATCCTTGGGG GAGGATCGGG GTGTCCGAGG G          51

(2) INFORMATION FOR SEQ ID NO: 47:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO: 47:

GGATCCGGTA GCGGATCTGG TAGCGCTCCT GATGTGCAGG ATTGCCCA              48

(2) INFORMATION FOR SEQ ID NO: 48:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 48:

TCCGGATTAG CTTGAGATGG ATCCGGTACC TTAAGATTTG TGATAATAAC AAGTACTGCA  60

(2) INFORMATION FOR SEQ ID NO: 49:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 49:

ATGAAATCGA CGGAATCAGA CTCGAGCCAA GG                                32

(2) INFORMATION FOR SEQ ID NO: 50:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 50:

TCCGGATTAG CTTGAGATGG ATCCGGTACC TTA                               33

(2) INFORMATION FOR SEQ ID NO: 51:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO: 51:

Met Glu Met Phe Gln Gly Leu Leu Leu Leu Leu Leu Leu Ser Met Gly
 1           5                 10               15

Gly Thr Trp Ala
        20

(2) INFORMATION FOR SEQ ID NO: 52:

(i) SEQUENCE CHARACTERISTICS:
        (A) LENGTH: 8 amino acids (B) TYPE: amino acid
            (C) STRANDEDNESS: single
            (D) TOPOLOGY: linear (xi) SEQUENCE DESCRIPTION: SEQ ID NO: 52:

Gly Ser Gly Ser Gly Ser Gly Ser
 1               5

(2) INFORMATION FOR SEQ ID NO: 53:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO: 53:

GCTACCGGAT CCCCGCGGGT CATCACAGGT CAAGGGGTGG T                    41

(2) INFORMATION FOR SEQ ID NO: 54:

(i) SEQUENCE CHARACTERISTICS:
            (A) LENGTH: 56 base pairs
            (B) TYPE: nucleic acid
            (C) STRANDEDNESS: single
            (D) TOPOLOGY: linear (xi) SEQUENCE DESCRIPTION: SEQ ID NO: 54:

ATGAAATCGA CGGAATCAGA CTCGAGCCAA GGAATGGAGA TGCTCCAGGG GCTGCT          56

(2) INFORMATION FOR SEQ ID NO: 55:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (xi) SEQUENCE DESCRIPTION: SEQ ID NO: 55:

GCTACCAGAT CCGCTACCGG ATCCTTGGGG GTGGTCACAG GTCAAGGGGT G              51

(2) INFORMATION FOR SEQ ID NO: 56:

(i) SEQUENCE CHARACTERISTICS:
            (A) LENGTH: 20 amino acids
            (B) TYPE: amino acid
            (C) STRANDEDNESS: single
            (D) TOPOLOGY: linear (xi) SEQUENCE DESCRIPTION: SEQ ID NO: 56:

Met Glu Met Leu Gln Gly Leu Leu Leu Leu Leu Leu Leu Ser Met Gly
 1               5                  10                  15

Gly Ala Trp Ala
            20

(2) INFORMATION FOR SEQ ID NO: 57:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (xi) SEQUENCE DESCRIPTION: SEQ ID NO: 57:

ATGAAATCGA CGGAATCAGA CTCGAGCCAA GGATGAAGAC ACTCCAGTTT TTCTTCC         57

(2) INFORMATION FOR SEQ ID NO: 58:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO: 58:

```
ACCAGATCCG CTACCGGATC CTTCTTTCAT TTCACCAAAG GAGCAG                    46
```

(2) INFORMATION FOR SEQ ID NO: 59:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 59:

```
Met Lys Thr Leu Gln Phe Phe Phe Leu Phe Cys Cys Trp Lys Ala Ile
 1               5                  10                  15
Cys Cys
```

(2) INFORMATION FOR SEQ ID NO: 60:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (xi) SEQUENCE DESCRIPTION: SEQ ID NO: 60:

```
GCTACCGGAT CCTTCTTTCA TTTCACCAAA GGAGCAGTAG CTGGGCCCCA GGCCTCGCAC     60

AGTACAATCA GTGCTGTCGC TGTCGCAGAG TGCACATTGA CAGCTGACAG C             111
```

(2) INFORMATION FOR SEQ ID NO: 61:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO: 61:

```
GCTACCGGAT CCTTCTTTCA TTTCACCAAA GGAGCAGTAG CTGGGCCCCA GGCCTCGCAC     60

AGTGCAGTCA GTGGTGCTGC GGCGGCA                                         87
```

(2) INFORMATION FOR SEQ ID NO: 62:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO: 62:

```
GCTACCGGAT CCTTCACCAA AGGAGCAGTA GCTGGGCCCC AGGCCTCGCA CAGTGCAGTC     60

AGTGGTGCTG CGGCGGCA                                                   78
```

(2) INFORMATION FOR SEQ ID NO: 63:

(i) SEQUENCE CHARACTERISTICS:
        (A) LENGTH: 78 base pairs
        (B) TYPE: nucleic acid (C) STRANDEDNESS: single
            (D) TOPOLOGY: linear (xi) SEQUENCE DESCRIPTION: SEQ ID NO: 63:

GCTACCGGAT CCCCGCGGGT CATCGCAGTA GCTGGGCCCC AGGCCTCGCA CAGTGCAGTC        60

AGTGGTGCTG CGGCGGCA        78

(2) INFORMATION FOR SEQ ID NO: 64:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (xi) SEQUENCE DESCRIPTION: SEQ ID NO: 64:

TGCTTCTCTA GAGCATATCC CACTCCACTA AGGTCCAAGA AGACGATGTT GGTCCAAAAG        60

CAAGTCACCT        70

(2) INFORMATION FOR SEQ ID NO: 65:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (xi) SEQUENCE DESCRIPTION: SEQ ID NO: 65:

GTACCGGTAC CTTAAGATTT GTGATAATAA CAAGTACTGC AGTGGCACGC CGTGTGTTGC        60

TCCACTTTGA AAC        73

(2) INFORMATION FOR SEQ ID NO: 66:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (xi) SEQUENCE DESCRIPTION: SEQ ID NO: 66:

CGGGGTAGGT TCGGTGGGAC CGACACCTCT TCCTCCCGAC GGGG        44

(2) INFORMATION FOR SEQ ID NO: 67:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (xi) SEQUENCE DESCRIPTION: SEQ ID NO: 67:

CTACCACCAC AACTGCCACT ACGTGTGCCC CGTCGGGAGG AAGAGGTG        48

(2) INFORMATION FOR SEQ ID NO: 68:

(i) SEQUENCE CHARACTERISTICS:
            (A) LENGTH: 145 amino acids
            (B) TYPE: amino acid
            (C) STRANDEDNESS: single
            (D) TOPOLOGY: linear (xi) SEQUENCE DESCRIPTION: SEQ ID NO: 68:

Ser Lys Glu Pro Leu Arg Pro Arg Cys Arg Pro Ile Asn Ala Thr Leu
 1               5                  10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
 50                  55                  60

Glu Ser Ile Arg Leu Pro Gly Cys Pro Arg Gly Val Asn Pro Val Val
 65                  70                  75                  80

Ser Tyr Ala Val Ala Leu Ser Cys Gln Cys Ala Leu Cys Arg Arg Ser
                 85                  90                  95

Thr Thr Asp Cys Gly Gly Pro Lys Asp His Pro Leu Thr Cys Asp Asp
            100                 105                 110

Pro Arg Phe Gln Asp Ser Ser Ser Lys Ala Pro Pro Ser Leu
            115                 120                 125

Pro Ser Pro Ser Arg Leu Pro Gly Pro Ser Asp Thr Pro Ile Leu Pro
 130                 135                 140

Gln
145

(2) INFORMATION FOR SEQ ID NO: 69:

(i) SEQUENCE CHARACTERISTICS:
        (A) LENGTH: 114 amino acids
        (B) TYPE: amino acid
        (C) STRANDEDNESS: single
        (D) TOPOLOGY: linear (xi) SEQUENCE DESCRIPTION: SEQ ID NO: 69:

Ser Lys Glu Pro Leu Arg Pro Arg Cys Arg Pro Ile Asn Ala Thr Leu
 1               5                  10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
 50                  55                  60

Glu Ser Ile Arg Leu Pro Gly Cys Pro Arg Gly Val Asn Pro Val Val
 65                  70                  75                  80

Ser Tyr Ala Val Ala Leu Ser Cys Gln Cys Ala Leu Cys Arg Arg Ser
                 85                  90                  95

Thr Thr Asp Cys Gly Gly Pro Lys Asp His Pro Leu Thr Cys Asp Asp
            100                 105                 110

Pro Arg (2) INFORMATION FOR SEQ ID NO: 70:

(i) SEQUENCE CHARACTERISTICS:
        (A) LENGTH: 93 amino acids
        (B) TYPE: amino acid
        (C) STRANDEDNESS: single
        (D) TOPOLOGY: linear (xi) SEQUENCE DESCRIPTION: SEQ ID NO: 70:

Ser Lys Glu Pro Leu Arg Pro Arg Cys Arg Pro Ile Asn Ala Thr Leu
 1               5                  10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val

```
                 35                  40                  45
Leu Pro Ala Leu Pro Gln Val Val Cys Asn Tyr Arg Asp Val Arg Phe
 50                  55                  60

Glu Ser Ile Arg Leu Pro Gly Cys Pro Arg Gly Val Asn Pro Val Val
 65                  70                  75                  80

Ser Tyr Ala Val Ala Leu Ser Cys Gln Cys Ala Leu Cys
                 85                  90
```

(2) INFORMATION FOR SEQ ID NO: 71:

(i) SEQUENCE CHARACTERISTICS:
        (A) LENGTH: 114 amino acids
        (B) TYPE: amino acid
        (C) STRANDEDNESS: single
        (D) TOPOLOGY: linear (xi) SEQUENCE DESCRIPTION: SEQ ID NO: 71:

```
Ser Arg Glu Pro Leu Arg Pro Trp Cys His Pro Ile Asn Ala Ile Leu
 1                   5                  10                  15

Ala Val Glu Lys Glu Gly Cys Pro Val Cys Ile Thr Val Asn Thr Thr
                 20                  25                  30

Ile Cys Ala Gly Tyr Cys Pro Thr Met Met Arg Val Leu Gln Ala Val
                 35                  40                  45

Leu Pro Pro Leu Pro Gln Val Val Cys Thr Tyr Arg Asp Val Arg Phe
 50                  55                  60

Glu Ser Ile Arg Leu Pro Gly Cys Pro Arg Gly Val Asp Pro Val Val
 65                  70                  75                  80

Ser Phe Pro Val Ala Leu Ser Cys Arg Cys Gly Pro Cys Arg Arg Ser
                 85                  90                  95

Thr Ser Asp Cys Gly Gly Pro Lys Asp His Pro Leu Thr Cys Asp His
                100                 105                 110

Pro Gln
```

(2) INFORMATION FOR SEQ ID NO: 72:

(i) SEQUENCE CHARACTERISTICS:
        (A) LENGTH: 111 amino acids
        (B) TYPE: amino acid
        (C) STRANDEDNESS: single
        (D) TOPOLOGY: linear (xi) SEQUENCE DESCRIPTION: SEQ ID NO: 72:

```
Asn Ser Cys Glu Leu Thr Asn Ile Thr Ile Ala Val Glu Lys Glu Gly
 1                   5                  10                  15

Cys Gly Phe Cys Ile Thr Ile Asn Thr Thr Trp Cys Ala Gly Tyr Cys
                 20                  25                  30

Tyr Thr Arg Asp Leu Val Tyr Lys Asp Pro Ala Arg Pro Lys Ile Gln
                 35                  40                  45

Lys Thr Cys Thr Phe Lys Glu Leu Val Tyr Glu Thr Val Arg Val Pro
 50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser Phe Gly Glu Met Lys Glu
                100                 105                 110
```

(2) INFORMATION FOR SEQ ID NO: 73:

(i) SEQUENCE CHARACTERISTICS:
    (A) LENGTH: 108 amino acids
    (B) TYPE: amino acid
    (C) STRANDEDNESS: single
    (D) TOPOLOGY: linear (xi) SEQUENCE DESCRIPTION: SEQ ID NO: 73:

Asn Ser Cys Glu Leu Thr Asn Ile Thr Ile Ala Val Glu Lys Glu Gly
 1               5                  10                  15

Cys Gly Phe Cys Ile Thr Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
 50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu
            100                 105

(2) INFORMATION FOR SEQ ID NO: 74:

(i) SEQUENCE CHARACTERISTICS:
        (A) LENGTH: 104 amino acids
        (B) TYPE: amino acid
        (C) STRANDEDNESS: single
        (D) TOPOLOGY: linear (xi) SEQUENCE DESCRIPTION: SEQ ID NO: 74:

Asn Ser Cys Glu Leu Thr Asn Ile Thr Ile Ala Val Glu Lys Glu Gly
 1               5                  10                  15

Cys Gly Phe Cys Ile Thr Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
 50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys
            100

(2) INFORMATION FOR SEQ ID NO: 75:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO: 75:

Asp Ser Asp Ser Thr Asp Cys Thr Val Arg Gly Leu Gly Pro Ser Tyr
 1               5                  10                  15

Cys Ser Phe Gly Glu Met Lys Glu
            20

(2) INFORMATION FOR SEQ ID NO: 76:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO: 76:

```
Thr Val Arg Gly Leu Gly Pro Ser Tyr Cys Ser Phe Gly Glu Met Lys
 1               5                  10                  15
Glu
```

(2) INFORMATION FOR SEQ ID NO: 77:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 77:

```
Thr Val Arg Gly Leu Gly Pro Ser Tyr Cys Ser Phe Gly Glu
 1               5                  10
```

(2) INFORMATION FOR SEQ ID NO: 78:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 78:

```
Thr Val Arg Gly Leu Gly Pro Ser Tyr
 1               5
```

(2) INFORMATION FOR SEQ ID NO: 79:

(i) SEQUENCE CHARACTERISTICS:
        (A) LENGTH: 92 amino acids
        (B) TYPE: amino acid
        (C) STRANDEDNESS: single
        (D) TOPOLOGY: linear (xi) SEQUENCE DESCRIPTION: SEQ ID NO: 79:

```
Ala Pro Asp Val Gln Asp Cys Pro Glu Cys Thr Leu Gln Glu Asn Pro
 1               5                  10                  15

Phe Phe Ser Gln Pro Gly Ala Pro Ile Leu Gln Cys Met Gly Cys Cys
                20                  25                  30

Phe Ser Arg Ala Tyr Pro Thr Pro Leu Arg Ser Lys Lys Thr Met Leu
            35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90
```

(2) INFORMATION FOR SEQ ID NO: 80:

(i) SEQUENCE CHARACTERISTICS:
        (A) LENGTH: 4 amino acids
        (B) TYPE: amino acid

```
            (C) STRANDEDNESS: single
            (D) TOPOLOGY: linear (xi) SEQUENCE DESCRIPTION: SEQ ID NO: 80:

Gly Ser Gly Ser
 1

(2) INFORMATION FOR SEQ ID NO: 81:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO: 81:

Gly Ser Gly Ser Gly Ser
 1               5

(2) INFORMATION FOR SEQ ID NO: 82:

(i) SEQUENCE CHARACTERISTICS:
            (A) LENGTH: 10 amino acids
            (B) TYPE: amino acid
            (C) STRANDEDNESS: single
            (D) TOPOLOGY: linear (xi) SEQUENCE DESCRIPTION: SEQ ID NO: 82:

Gly Ser Gly Ser Gly Ser Gly Ser Gly Ser
 1               5                   10

(2) INFORMATION FOR SEQ ID NO: 83:

(i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO: 83:

Asp Asp Pro Arg
```

SINGLE CHAIN FORMS OF THE GLYCOPROTEIN HORMONE QUARTET

CROSS-REFERENCE TO RELATED APPLICATIONS

This application is a continuation-in-part of U.S. Ser. No. 08/853,524 filed May 9, 1997, now pending, which is a continuation-in-part of U.S. Ser. No. 08/475,049 filed Jun. 7, 1995 and now abandoned, which is a continuation-in-part of U.S. Ser. No. 08/351,591 filed Dec. 7, 1994 which was abandoned in favor of U.S. Ser. No. 08/806,772 filed Feb. 26, 1997 which is now allowed, and which application 08/351,591 is a continuation-in-part of U.S. Ser. No. 08/334,628 filed Nov. 4, 1994 and now U.S. Pat. No. 5,705,478, which is a continuation-in-part of U.S. Ser. No. 08/310,590 filed Sep. 22, 1994 and now abandoned, which is a continuation-in-part of U.S. Ser. No. 08/289,396 filed Aug. 12, 1994 which is now abandoned in favor of U.S. Ser. No. 08/890,732 filed Jul. 11, 1997 which is now pending. This application is also a continuation-in-part of U.S. Ser. No. 08/199,382 filed Feb. 18, 1994 and now abandoned. The contents of the above-mentioned applications are incorporated herein by reference.

ACKNOWLEDGEMENT OF GOVERNMENT SUPPORT

This invention was made with government support under NIH Contract No. NO1-HD-9-2922, awarded by the National Institutes of Health. The government has certain rights in this invention.

TECHNICAL FIELD

The invention relates to the field of protein engineering and the glycoprotein hormones which occur normally as heterodimers. More specifically, the invention concerns single-chain forms of chorionic gonadotropin (CG), thyroid stimulating hormone (TSH), luteinizing hormone (LH), and follicle stimulating hormone (FSH).

BACKGROUND ART

In humans, four important glycoprotein hormone heterodimers (LH, FSH, TSH AND CG) have identical α subunits and differing β subunits. Three of these hormones PCT application WO90/09800, published Sep. 7, 1990 and incorporated herein by reference, describes a number of modified forms of these hormones. One important modification is C-terminal extension of the β subunit by the carboxy terminal peptide of human chorionic gonadotropin or a variant thereof. Other muteins of these hormones are also described. The relevant positions for the CTP are from any one of positions 112–118 to position 145 of the β subunit of human chorionic gonadotropin. The PCT application describes variants of the CTP extension obtained by conservative amino acid substitutions such that the capacity of the CTP to alter the clearance characteristics is not destroyed. In addition, U.S. Serial No. 08/049,869 filed Apr. 20, 1993, incorporated herein by reference, describes modifying these hormones by extension or insertion of the CTP at locations other than the C-terminus and CTP fragments shorter than the sequence extending from positions 112–118 to 145.

The CTP-extended β subunit of FSH is also described in two papers by applicants herein: LaPolt, P. S. et al.; *Endocrinology* (1992) 131:2514–2520 and Fares, F. A. et al.; *Proc Natl Acad Sci USA* (1992) 89:4304–4308. Both of these papers are incorporated herein by reference.

The crystal structure of the heterodimeric form of human chorionic gonadotropin has now been published in more or less contemporaneous articles, one by Lapthorn, A. J. et al. *Nature* (1994) 369:455–461 and the other by Wu, H. et al. *Structure* (1994) 2:545–558. The results of these articles are summarized by Patel, D. J. *Nature* (1994) 369:438–439.

At least one instance of preparing a successful single-chain form of a heterodimer is now known. The naturally occurring sweetener protein, monellin, is isolated from serendipity berries in a heterodimeric form. Studies on the crystal structure of the heterodimer were consistent with the proposition that the C-terminus of the B chain could be linked to the N-terminus of the A chain through a linker which preserved the spatial characteristics of the heterodimeric form. Such a linkage is advantageous because, for use as a sweetener protein, it would be advantageous to provide this molecule in a form stable at high temperatures. This was successfully achieved by preparing the single-chain form, thus impeding heat denaturation, as described in U.S. Pat. No. 5,264,558.

PCT application WO91/16922 published Nov. 14, 1991 describes a multiplicity of chimeric and otherwise modified forms of the heterodimeric glycoprotein hormones. In general, the disclosure is focused on chimeras of α subunits or β subunits involving portions of various α or β chains respectively. One construct simply listed in this application, and not otherwise described, fuses substantially all of the β chain of human chorionic gonadotropin to the α subunit preprotein, i.e., including the secretory signal sequence for this subunit. This construct falls outside the scope of the present invention since the presence of the signal sequence intervening between the β and α chains fails to serve as a linker moiety as defined and described herein.

It has now been found that the normally heterodimeric glycoprotein hormones retain their properties when in single-chain form, including single-chain forms that contain the various CTP extensions and insertions described above.

DISCLOSURE OF THE INVENTION

The invention provides single-chain forms of the glycoprotein hormones, at least some of which hormones are found in most vertebrate species. The single-chain forms of the invention may either be glycosylated, partially glycosylated, or nonglycosylated and the α and β chains that occur in the native glycoprotein hormones or variants of them may optionally be linked through a linker moiety. Particularly preferred linker moieties include the carboxy terminal peptide (CTP) unit either as a complete unit or only as a portion thereof, as well as shorter linkers of 1–16 amino acids. The resulting single-chain hormones either retain the activity of the unmodified heterodimeric form or are antagonists of this activity.

Thus, in one aspect, the invention is directed to a glycosylated or nonglycosylated protein which comprises the amino acid sequence of the α subunit common to the glycoprotein hormones linked covalently, optionally through a linker moiety, to the amino acid sequence of the β subunit of one of said hormones, or variants of said amino acid sequences wherein said variants are defined herein.

The availability of single-chain forms preserves conformation so that the entire portions of the subunits that make up the single-chain forms are unnecessary. Thus, the invention includes single-chain forms of fragments of the subunits wherein the single-chain forms retain the biological activity exhibited by the single-chain forms of the complete subunits.

In other aspects, the invention is directed to recombinant materials and methods to produce the single-chain proteins of the invention, to pharmaceutical compositions containing them; to antibodies specific for them; and to methods for their use.

BRIEF DESCRIPTION OF THE DRAWINGS

FIG. 5 shows the coding sequence for analog no. 1 (SEQ ID NO:2–3) and primers therefor (SEQ ID NO:4);

FIG. 6 shows the coding sequence for analog no. 2 (SEQ ID NO:5–6) and primers therefore SEQ ID NO:7;

FIG. 7 shows the coding sequence for analog no. 3 (SEQ ID NO:8–9) and primers therefor (SEQ ID NO:10);

FIG. 8 shows the coding sequence for analog no. 4 (SEQ ID NO:11–12) and primers therefor (SEQ ID NO:13);

FIG. 9 shows the coding sequence for analog no. 5 (SEQ ID NO: 14–15) and primers therefor (SEQ ID NO:16);

FIG. 10 shows the coding sequence for analog no. 6 (SEQ ID NO: 17–18) and primers therefor (SEQ ID NO:19);

FIG. 11 shows the coding sequence for analog no. 7 (SEQ ID NO:20–21) and primers therefor (SEQ ID NO:22);

FIG. 12 shows the coding sequence for analog no. 8 (SEQ ID NO:23–24) and primers therefor (SEQ ID NO:25);

FIG. 13 shows the coding sequence for analog no. 9 (SEQ ID NO:26–27) and primers therefor (SEQ ID NO:28);

FIG. 14 shows the coding sequence for analog no. 10 (SEQ ID NO:29–30) and primers therefor (SEQ ID NO:31);

FIG. 15 shows the preparation of an α subunit encoding region lacking oligosaccharide binding sites (SEQ ID NO:32–34).

FIG. 16 shows the preparation of a β subunit encoding region lacking N-linked oligosaccharide binding sites (SEQ ID NO:35–37).

FIG. 17 shows the sequence encoding a single-chain gonadotropin analog No. 1a (SEQ ID NO:38–40).

MODES OF CARRYING OUT THE INVENTION

Figure 1:
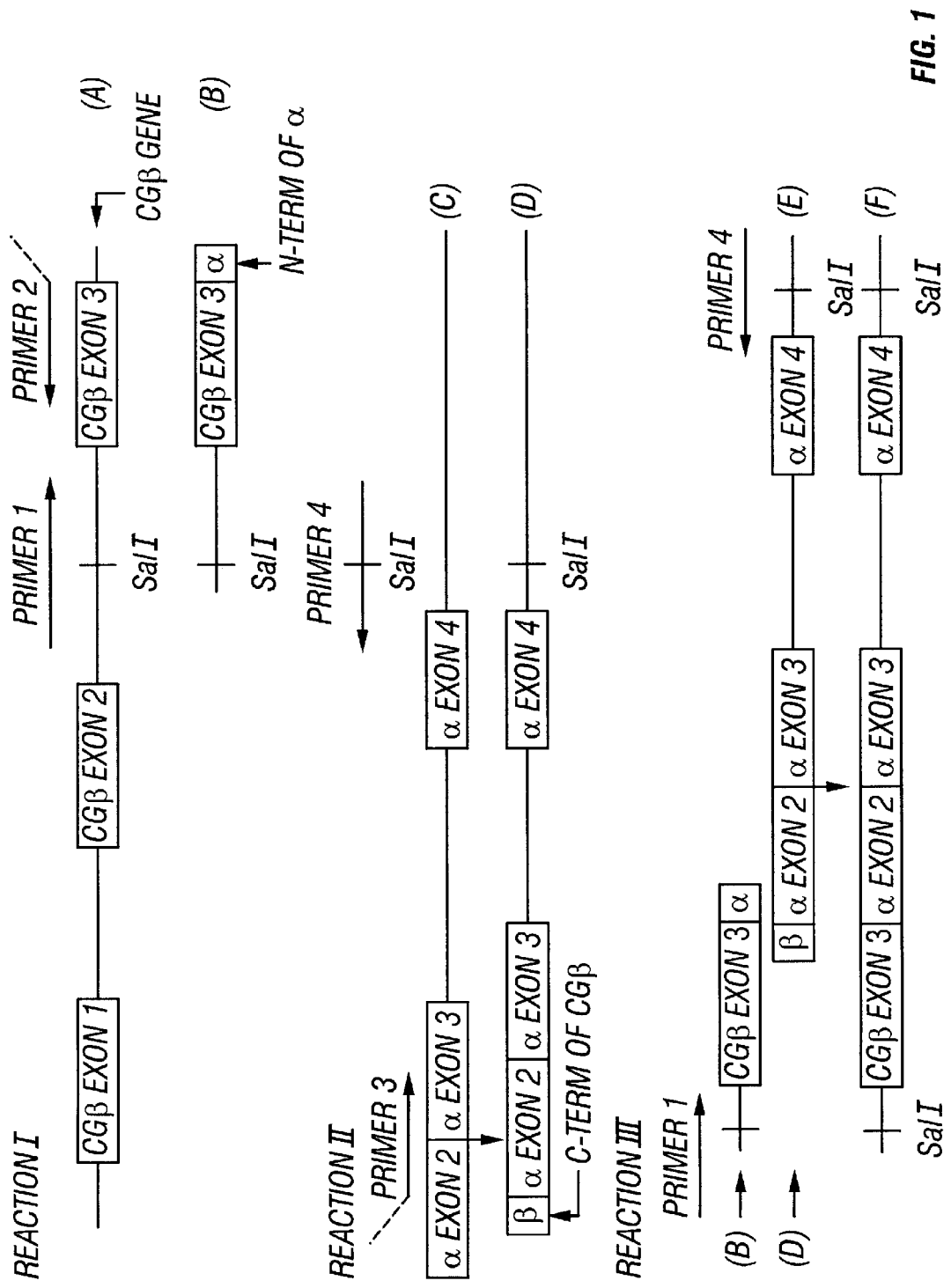
FIG. 1 shows the construction of a SaI bounded DNA fragment fusing the third exon of CGβ with the second exon encoding the α subunit.

Four "glycoprotein" hormones in humans provide a family which includes human chorionic gonadotropin (hCG), follicle stimulating hormone (FSH), luteinizing hormone (LH), and thyroid stimulating hormone (TSH). As used herein, "glycoprotein hormones" refers to the members of this family. All of these hormones are heterodimers comprised of α subunits which, for a given species, are identical in amino acid sequence among the group, and β subunits which differ according to the member of the family. Thus, normally these glycoprotein hormones occur as heterodimers composed of α and β subunits associated with each other but not covalently linked. Most vertebrates produce FSH, TSH and LH; chorionic gonadotropin has been found only in primates, including humans, and horses.

Thus, this hormone "quartet" is composed of heterodimers wherein the α and β subunits of each are encoded in different genes and are separately synthesized by the host. The host then assembles the separately synthesized subunits into a non-covalently linked heterodimeric complex. In this manner, the heterodimers of this hormone quartet differ from heterodimers such as insulin which is synthesized from a single gene (in this case with an intervening "pro" sequence) and the subunits are covalently coupled using disulfide linkages. This hormone quartet is also distinct from the immunoglobulins which are assembled from different loci, but are covalently bound through disulfide linkages. On the other hand, monellin, which is, however, a plant protein, is held together through noncovalent interaction between its A and B chains. It is not known at present whether the two chains are encoded on separate genes.

Thus, a variety of factors is influential in determining the behavior of biologically active compounds which are dimers formed from subunits that are identical or different. The subunits may be covalently or noncovalently linked; they may be synthesized by the same or different genes; and they may or may not contain, in their precursor forms, a "pro" sequence linking the two members of the dimer. Based on the results obtained with the single-chain forms of the glycoprotein hormone quartet herein, it is apparent that single-chain forms of the biologically active dimers interleukin-12, interleukin-3 (IL-12 and IL-3), inhibin, tumor necrosis factor (TNF), and transforming growth factor (TGF) will also be biologically active.

The single-chain forms of the heterodimers or homodimers have a number of advantages over their dimeric forms. First, they are generally more stable. LH, in particular, is noted for its instability and short half-life. Second, problems of recombinant production are reduced since only a single gene need be transcribed, translated and processed. This is particularly important for expression in bacteria. Third, of course, they provide an alternate form thus permitting fine tuning of activity levels and of in vivo half lives. Finally, single chain forms are unique starting materials for identifying truncated forms with the activity of the dimer. The linkage between the subunits permits the protein to be engineered without disturbing the overall folding of the protein.

With respect to this last point, it will be evident that because the conformation is stabilized in the single-chain forms, less than the complete single-chain conjugate of the subunits that compose it will generally be needed. Therefore, the invention covers fragments of the single-chain proteins that retain biological activity; these fragments may be visualized as single-chain forms obtained from fragments of the subunits per se.

Features of the Members of the Quartet

The β subunit of hCG is substantially larger than the other β subunits in that it contains approximately 34 additional amino acids at the C-terminus referred to herein as the carboxy terminal portion (CTP) which, when glycosylated at the O-linked sites, is considered responsible for the comparatively longer serum half-life of hCG as compared to other gonadotropins (Matzuk, M. et al., Endocrinol (1989) 126:376). In the native hormone, this CTP extension contains four mucin-like O-linked oligosaccharides.

In one embodiment of the present invention, the α and β chains of the glycoprotein hormones are coupled into a single-chain proteinaceous material where the α and β chain are covalently linked, optionally through a linker moiety. The linker moiety may include further amino acid sequence, and in particular the CTP units described herein can be advantageously included in the linker. In addition, the linker may include peptide or nonpeptide drugs which can be targeted to the receptors for the hormones.

In addition to the head-to-tail configuration that is achievable by simply coupling the two peptide chains through a peptide bond, the α and β chains can be linked head-to-head or tail-to-tail. Head to head and tail to tail couplings involve synthetic chemistry using standard techniques to link two carboxyl or two amino groups through a linker moiety. For example, two amino groups may be linked through an anhydride or through any dicarboxylic acid derivative; two carboxyl groups can be linked through diamines or diols using standard activation techniques. However, the most preferred form is a head to tail configuration wherein standard peptide linkages suffice and the single-chain compound can be prepared as a fusion protein recombinantly or using synthetic peptide techniques either in a single chain or, preferably, ligating individual portions of the entire sequence. Of course, if desired, peptide or non-peptide linker moieties can be used in this case as well, but this is unnecessary and the convenience of recombinant production of the single-chain protein would suggest that embodiments that permit this method of production comprise by far the most preferred approach.

When a head-to-tail configuration is employed, linkers may consist essentially of additional peptide sequence. As is the case with the heterodimers, the two β chains may be linked through a CTP unit as further described below. Thus, possible embodiments of the invention include, with the N-terminus at the left, α-FSHβ, βFSH-α, α-βLH, α-CTP-βLH, βLH-CTP-α, CTP-βLH-CTP-α; and the like.

The following definitions may be helpful in describing the single-chain forms of the molecules.

As used herein, α subunit, and FSH, LH, TSH, and CG β subunits as well as the heterodimeric forms have in general their conventional definitions and refer to the proteins having the amino acid sequences known in the art per se, or allelic variants thereof, regardless of the clycosylation pattern exhibited.

"Native" forms of these peptides are those which have the amino acid sequences isolated from the relevant vertebrate tissue, and have these known sequences per se, or their allelic variants.

"Variant" forms of these proteins are those which have deliberate alterations in amino acid sequence of the native protein produced by, for example, site-specific mutagenesis or by other recombinant manipulations, or which are prepared synthetically.

These alterations consist of 1–10, preferably 1–8, and more preferably 1–5 amino acid changes, including deletions, insertions, and substitutions, most preferably conservative amino acid substitutions as defined below. The resulting variants must retain activity which affects the corresponding activity of the native hormone—i.e., either they must retain the biological activity of the native hormone directly, or they must behave as antagonists, generally by virtue of being able to bind the receptors for the native hormones but lacking the ability to effect signal transduction. For example, it is known that if the glycosylation site at position 52 of the α subunit is removed by an amino acid substitution, therefore preventing all glycosylation at that site, the hormones which are heterodimers with this altered α subunit are generally agonists and are able to bind receptors preventing the native hormone from doing so in competition. (On the other hand, the glycosylation site of the α subunit at position 78 appears not greatly to affect the activity of the hormones.) Other alterations in the amino acid sequence may also result in antagonist rather than agonist activity for the variant.

One set of preferred variants are those wherein the glycosylation sites of either the α or β subunits or both have been altered. The α subunit contains two glycosylation sites, one at position 52 and the other at position 78, and the effect of alterations of these sites on activity has just been described. Similarly, the β subunits generally contain two N-linked glycosylation sites (at positions that vary somewhat with the nature of the β chain) and similar alterations can be made at these sites. The CTP extension of hCG contains four O-linked glycosylation sites, and conservative mutations at the serine residues (e.g., conversion of the serine to alanine) destroys these sites. Destruction of the O-linked glycosylation sites may effect conversion of against activity to antagonist activity.

Finally, alterations in amino acid sequence that are proximal to the N-linked or O-linked glycosylation sites influence the nature of the glycosylation that is present on the resulting molecule and also alter activity.

Alterations in amino acid sequence also include both insertions and deletions. Thus, truncated forms of the hormones are included among variants, e.g., mutants of the α subunit which ale lacking some or all of the amino acids at positions 85–92 at the C-terminus. In addition, α subunits with 1–10 amino acids deleted from the N-terminus are included. Some useful variants of the hormone quartet described herein are set forth in U.S. Pat. No. 5,177,193 issued Jan. 5, 1993 and incorporated herein by reference. As shown therein, the glycosylation patterns can be altered by destroying the relevant sites or, in the alternative, by choice of host cell in which the protein is produced.

As explained above, the single chain forms are convenient starting materials for various engineered muteins. Such muteins include those with non-critical regions altered or removed. Such deletions and alterations may comprise entire loops, so that sequences of considerably more than 10 amino acids may be deleted or changed. The single chain molecules must, however, retain at least the receptor binding domains and/or the regions involved in signal transduction.

There is considerable literature on variants of the hormone quartet described herein and it is clear from this literature that a large number of possible variants which result both in agonist and antagonist activity can be prepared. Such variants are disclosed, for example, in Chen, F. et al. *Molec Endocrinol* (1992) 6:914–919; Yoo, J. et al. *J Biol Chem* (1993) 268:13034–13042; Yoo, J. et al. *J Biol Chem* (1991) 266:17741–17743; Puett, D. et al. *Glycoprotein Hormones,* Lusbader, J. W. et al. EDS, Springer Verlag New York (1994) 122–134; Kuetmann, H. T. et al. (ibid) pages 103–117; Erickson, L. D. et al. *Endocrinology* (1990) 126:2555–2560; and Bielinska, M. et al. *J Cell Biol* (1990) 111:330a (Abstract 1844).

As described hereinabove, one method of constructing effective antagonists is to prepare a single-chain molecule containing two β subunits of the same or different member of the glycoprotein quartet. Particularly preferred variants of these single-chain forms include those wherein one or more cystine-link is deleted, typically by substituting a neutral amino acid for one or both cysteines which participate in the link. Particularly preferred cystine links which may be deleted are those between positions 26 and 110 and between positions 23 and 72.

In addition, it has been demonstrated that the β subunits of the hormone quartet can be constructed in chimeric forms so as to provide biological functions of both components of the chimera, or, in general, hormones of altered biological function. Thus, chimeric molecules which exhibit both FSH and LH/CG activities can be constructed as described by Moyle, *Proc Natl Acad Sci* (1991) 88:760–764; Moyle, *Nature* (1994) 368:251–255. As disclosed in these papers, substituting amino acids 101–109 of FSH-β for the corresponding residues in the CG-β subunit yields an analog with both hCG and FSH activity.

Although it is recognized that glycosylation pattern has a profound influence on activity both qualitatively and quantitatively, for convenience the terms FSH, LH, TSH, and CG β subunits refers to the amino acid sequence characteristic of the peptides, as does "α subunit." When only the β chain is referred to, the terms will be, for example, FSHβ; when the heterodimer is referred to, the simple term "FSH" will be used. It will be clear from the context in what manner the glycosylation pattern is affected by, for example, recombinant expression host or alteration in the glycosylation sites. Forms of the glycoprotein with specified glycosylation patterns will be so noted.

As used herein "peptide" and "protein" are used interchangeably, since the length distinction between them is arbitrary.

As stated above, the subunits employed in forming the single-chain conjugates with or without linking moieties may represent the complete amino acid sequences of the subunits or only portions thereof Single-chain conjugates of α and β subunits are composed of these subunits per se or of those fragments of the subunits which result in a single-chain form with biological activity comparable to that exhibited by the single chain composed of the corresponding complete subunits.

In the single-chain forms of the present invention, the α and/or β chain may contain a CTP extension inserted into a noncritical region.

"Noncritical" regions of the α and β subunits are those regions of the molecules not required for biological activity (including agonist and antagonist activity). In general, these regions are removed from binding sites, precursor cleavage sites, and catalytic regions. Regions critical for inducing proper folding, binding to receptors, catalytic activity and the like should be avoided; similarly, regions which are critical to assure the three-dimensional conformation of the protein should be avoided. It should be noted that some of the regions which are critical in the case of the dimer become non-critical in the single chain forms since the conformational restriction imposed by the single chain may obviate the necessity for these regions. The ascertainment of noncritical regions is readily accomplished by deleting or modifying candidate regions and conducting an appropriate assay for the desired activity. Regions where modifications result in loss of activity are critical; regions wherein the alteration results in the same or similar activity (including antagonist activity) are considered noncritical.

It should be emphasized, that by "biological activity" is meant activity which is either agonistic or antagonistic to that of the native hormones. Thus, certain regions are critical for behavior of a variant as an antagonist, even though the antagonist is unable to directly provide the physiological effect of the hormone.

For example, for the α subunit, positions 33–59 are thought to be necessary for signal transduction and the 20 amino acid stretch at the carboxy terminus is needed for signal transduction/receptor binding. Residues critical for assembly with the β subunit include at least residues 33–58, particularly 37–40.

Where the noncritical region is "proximal" to the N- or C-terminus, the insertion is at any location within 10 amino acids of the terminus, preferably within 5 amino acids, and most preferably at the terminus per se.

In general, "proximal" is used to indicate a position which is within 10 amino acids, preferably within five amino acids, of a referent position, and most preferably at the referent position per se. Thus, certain variants may contain substitutions of amino acids "proximal" to a glycosylation site, the definition is relevant here. In addition, the α and β subunits may be linked to each other at positions "proximal" to their N- or C-termini.

Figure 2:
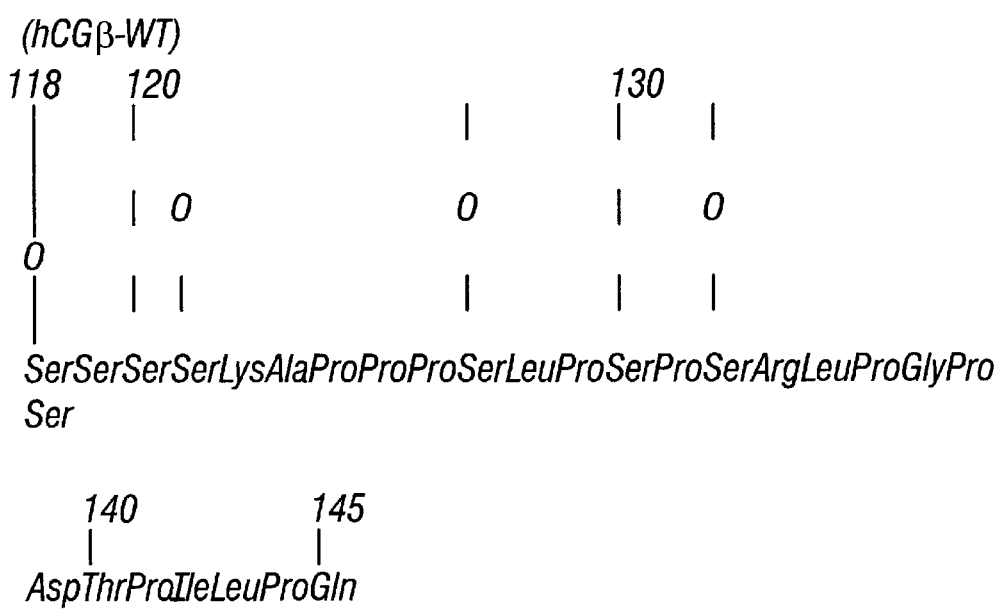
FIG. 2 shows the amino acid sequence and numbering of positions 112–145 of human CGβ (SEQ ID NO:1).

As used herein, the "CTP unit" refers to an amino acid sequence found at the carboxy terminus of human chorionic gonadotropin β subunit which extends from amino acid 112–118 to residue 145 at the C-terminus or to a portion thereof. Thus, each "complete" CTP unit contains 28–34 amino acids, depending on the N-terminus of the CTP. The native sequence of positions 112–145 is shown in FIG. 2.

By a "partial" CTP unit is meant an amino acid sequence which occurs between positions 112–118 to 145 inclusive, but which has at least one amino acid deleted from the shortest possible "complete" CTP unit (i.e. from positions 118–145). The "partial" CTP units included in the invention preferably contain at least one O-glycosylation site if agonist activity is desired. Some nonglycosylated forms of the hormones are antagonists and are useful as such. The CTP unit contains four such sites at the serine residues at positions 121 (site 1); 127 (site 2); 132 (site 3); and 138 (site 4). The partial forms of CTP useful in agonists of the invention will contain one or more of these sites arranged in the order in which they appear in the native CTP sequence. Thus, the "partial" CTP unit employed in agonists of the invention may include all four glycosylation sites; sites 1, 2 and 3; sites 1, 2 and 4; sites 1, 3 and 4; sites 2, 3 and 4; or simply sites 1 and 2; 1 and 3; 1 and 4; 2 and 3; 2 and 4; or 3 and 4; or may contain only one of sites 1, 2, 3 or 4.

By "tandem" inserts or extensions is meant that the insert or extension contains at least two "CTP units". Each CTP unit may be complete or a fragment, and native or a variant. All of the CTP units in the tandem extension or insert may be identical, or they may be different from each other. Thus, for example, the tandem extension or insert may generically be partial-complete; partial-partial; partial-complete-partial; complete-complete-partial, and the like wherein each of the noted partial or complete CTP units may independently be either a variant or the native sequence.

The "linker moiety" is a moiety that joins the α and β sequences without interfering with the activity that would otherwise be exhibited by the same α and β chains as members of a heterodimer, or which alters that activity to convert it from agonist to antagonist activity. The level of activity may change within a reasonable range, but the presence of the linker cannot be such so as to deprive the single-chain form of both substantial agonist and substantial antagonist activity. The single-chain form must remain as a single-chain form when it is recovered from its production medium and must exhibit activity pertinent to the hormonal activity of the heterodimer, the elements of which form its components. A typical linker would be a peptide containing 1–100 amino acids.

Variants

The hormone subunits and the CTP units may correspond exactly to the native hormone or CTP sequence, or may be variants. The nature of the variants has been defined hereinabove. In such variants, 1–10, preferably 1–8, and most preferably 1–5 of the amino acids contained in the native sequence are substituted by a different amino acid compared to the native amino acid at that position, or 1–10, more preferably 1–8 and most preferably 1–5 amino acids are simply deleted or combination of these. As pointed out above, when non-critical regions of the single chain forms are identified, in particular, through detecting the presence of non-critical "loops", the number of amino acids altered by deletion or substitution may be increased to 20 or 30 or any arbitrary number depending on the length of amino acid sequence in the relevant non-critical region. Of course, deletion or substitutions in more than one non-critical region results in still greater numbers of amino acids in the single chain forms being affected and substitution and deletions strategies may be used in combination. The substitutions or deletions taken cumulatively do not result in substantial elimination of agonist or antagonist activity associated with the hormone. Substitutions by conservative analogs of the native amino acid are preferred.

"Conservative analog" means, in the conventional sense, an analog wherein the residue substituted is of the same general amino acid category as that for which substitution is made. Amino acids have been classified into such groups, as is understood in the art, by, for example, Dayhoff, M. et al., *Atlas of Protein Sequences and Structure* (1972) 5:89–99. in general, acidic amino acids fall into one group; basic amino acids into another; neutral hydrophilic amino acids into another; and so forth.

More specifically, amino acid residues can be generally subclassified into four major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows.
Acidic: Aspartic acid and Glutamic acid;
Basic/noncyclic: Arginine, Lysine;
Basic/cyclic: Histidine;
Neutral/polar/small: Glycine, serine, cysteine;
Neutral/nonpolar/small: Alanine;
Neutral/polar/large/nonaromatic: Threonine, Asparagine, Glutamine;
Neutral/polar/large aromatic: Tyrosine;
Neutral/nonpolar/large/nonaromatic: Valine, Isoleucine, Leucine, Methionine;
Neutral/nonpolar/large/aromatic: Phenylalanine, and Tryptophan.

The gene-encoded secondary amino acid proline, although technically within the group neutral/nonpolar/large/cyclic and nonaromatic, is a special case due to its known effects on the secondary conformation of peptide chains, and is not, therefore, included in this defined group.

If the single-chain proteins of the invention are constructed by recombinant methods, they will contain only gene encoded amino acid substitutions; however, if any portion is synthesized by standard, for example, solid phase, peptide synthesis methods and ligated, for example, enzymatically, into the remaining protein, non-gene encoded amino acids, such as aminoisobutyric acid (Aib), phenylglycine (Phg), and the like can also be substituted for their analogous counterparts.

These non-encoded amino acids also include, for example, β-alanine (β-Ala), or other omega-amino acids, such as 3-amino propionic, 4-amino butyric and so forth, sarcosine (Sar), ornithine (Orn), citrulline (Cit), t-butylalanine (t-BuA), t-butylglycine (t-BuG), N-methylisoleucine (N-MeIle), and cyclohexylalanine (Cha), norleucine (Nle), cysteic acid (Cya) 2-naphthylalanine (2-Nal); 1,2,3,4-tetrahydroisoquinoline-3-carboxylic acid (Tic); mercaptovaleric acid (Mvl); β-2-thienylalanine (Thi); and methionine sulfoxide (MSO). These also fall conveniently into particular categories.

Based on the above definitions,
Sar and β-Ala and Aib are neutral/nonpolar/small;
t-BuA, t-BuG, N-MeIle, Nle, Mvl and Cha are neutral/nonpolar/large/nonaromatic;
Orn is basic/noncyclic;
Cya is acidic;
Cit, Acetyl Lys, and MSO are neutral/polar/ large/ nonaromatic; and
Phg, Nal, Thi and Tic are neutral/nonpolar/large/aromatic.

The various omega-amino acids are classified according to size as neutral/nonpolar/small (β-Ala, i.e., 3-aminopropionic, 4-aminobutyric) or large (all others).

Thus, amino acid substitutions other than those encoded in the gene can also be included in peptide compounds within the scope of the invention and can be classified within this general scheme according to their structure.

Preferred Embodiments of the Single-Chain Hormones

The single-chain hormones of the invention are most efficiently and economically produced using recombinant techniques. Therefore, those forms of α and β chains, CTP units and other linker moieties which include only gene-encoded amino acids are preferred. It is possible, however, as set forth above, to construct at least portions of the single-chain hormones using synthetic peptide techniques or other organic synthesis techniques and therefore variants which contain nongene-encoded amino acids are also within the scope of the invention.

In the most preferred embodiments of the single-chain hormones of the invention, the C-terminus of the β subunit is covalently linked, optionally through a linker, to the N-terminus of the mature α subunit, forms wherein the C-terminus of the α subunit is linked to the N-terminus of the β subunit are also useful, but may have less activity either as antagonists or agonists of the relevant receptor. The linkage can be a direct peptide linkage wherein the C-terminal amino acid of one subunit is directly linked through the peptide bond to the N-terminus of the other, however, in many instances it is preferable to include a linker moiety between the two termini. In many instances, the linker moiety will provide at least one β turn between the two chains. The presence of proline residues in the linker may therefore be advantageous.

As described above, the N-terminus of the α chain may also be coupled to the N-terminus of the β chain or the C-terminus of the α to the C-terminus of the β chain in any case through a linker unit.

It should be understood that in discussing linkages between the termini of the subunits comprising the single chain forms, one or more termini may be altered by substitution and/or deletion as described above.

While the head-to-head, tail-to-tail and head-to-tail configurations of the single-chain heterodimer have been described, the linkage between the two subunits may also occur at positions not precisely at the N- or C-terminus of each member but at positions proximal thereto.

In one particularly preferred set of embodiments, the linkage is head-to-tail and the linker moiety will include one or more CTP units and/or variants or truncated forms thereof. Preferred forms of the CTP units used in such linker moieties are described hereinbelow.

Further, the linker moiety may include a drug covalently, preferably releasably, bound to the linker moiety. Means for coupling the drug to the linker moiety and for providing for its release are conventional.

In addition to their occurrence in the linker moiety, CTP and its variants and truncations may also be included in any noncritical region of the subunits making up the single-chain hormone. The nature of these inclusions, and their positions, is set forth in detail in the parent application herein.

While CTP units are preferred inclusions in the linker moiety, it is understood that the linker may be any suitable covalently bound material which provides the appropriate spatial relationship between the α and β subunits. Thus, for head-to-tail configurations the linker may generally be a peptide comprising an arbitrary number, but typically less than 100, more preferably less than 50 amino acids which has the proper hydrophilicity/hydrophobicity ratio to provide the appropriate spacing and confirmation in solution. In general, the linker should be on balance hydrophilic so as to reside in the surrounding solution and out of the way of the interaction between the α and β subunits. It is preferable that the linker include β turns typically provided by proline residues. Any suitable polymer, including peptide linkers, with the above-described correct characteristics may be used.

One particular linker moiety that is not included within the scope of the invention is that which includes a signal peptide immediately upstream of the downstream subunit.

Particularly preferred embodiments of the single-chain hormones of the invention include:

βFSH-α;

βLH-α;

βTSH-α;

βCG-α;

βFSH-CTP-α;

βLH-CTP-α;

βCG-CTP-α;

βFSH-CTP-CTP-α;

βLH-CTP-CTP-α;

βCG-CTP-CTP-α;

and the like. Also particularly preferred are the human forms of the subunits. In the above constructions, "CTP" refers to CTP or its variants or truncations as further explained in the paragraph below.

Preferred Embodiments of CTP Units

The notation used for the CTP units of the invention is as follows: for portions of the complete CTP unit, the positions included in the portion are designated by their number as they appear in FIG. 2 herein. Where substitutions occur, the substituted amino acid is provided along with a superscript indicating its position. Thus, for example, CTP (120–143) represents that portion of CTP extending from positions 120 to 143; CTP (120–130; 136–143) represents a fused amino acid sequence lacking positions 118–119, 131–135, and 144–145 of the native sequence. CTP ($Arg^{122}$) refers to a variant wherein the lysine at position 122 is substituted by an arginine; CTP ($Ile^{134}$) refers to a variant wherein the leucine at position 134 is substituted by isoleucine. CTP ($Val^{28}Val^{143}$) represents a variant wherein two substitutions have been made, one for the leucine at position 128 and the other for the isoleucine at position 142. CTP (120–143; $Ile^{128} Ala^{130}$) represents the relevant portion of the CTP unit where the two indicated substitutions have been made.

Also preferred among variants of CTP are those wherein one or more of the O-linked glycosylation sites have been altered or deleted. One particularly preferred means of altering the site to prevent glycosylation is substitution of an alanine residue for the serine residue in these sites.

Particularly preferred are those CTP units of the following formulas:

1 CTP (116–132)
2 CTP (118–128; 130–135)
3 CTP (117–142)
4 CTP (116–130)
5 CTP (116–123; 137–145)
6 CTP (115–133; 141–145)
7 CTP (117–140, $Ser^{123}$ $Gln^{140}$)
8 CTP (125–143, $Ala^{130}$)
9 CTP (135–145, $Glu^{139}$)
10 CTP (131–143, $Val^{142}$ $Val^{143}$)
11 CTP (118–132)
12 CTP (118–127)
13 CTP (118–145)
14 CTP (115–132)
15 CTP (115–127)
16 CTP (115–145)
17 CTP (112–145)
18 CTP (112–132)
19 CTP (112–127)

Preferred Embodiments of the α and β Subunits

Of course, the native forms of the α and β subunits in the single-chain form are among the preferred embodiments. However, certain variants are also preferred.

In particular, variants of the α subunit in which the N-linked glycosylation site at position 52 is eliminated or altered by amino acid substitutions at or proximal to this site are preferred for antagonist activity. Similar modifications at the glycosylation site at position 78 are -also preferred. Deletion of one or more amino acids at positions 85–92 also affects the nature of the activity of hormones containing the α subunit and substitution or deletion of amino acids at these positions is also among the preferred embodiments.

Similarly, the N-linked glycosylation sites in the β chain can conveniently be modified to eliminate glycosylation and thus affect the agonist or antagonist activity of the β chains. If CTP is present, either natively as in CG or by virtue of being present as a linker, the O-linked glycosylation sites in this moiety may also be altered.

Particular variants containing modified or deleted glycosylation sites are set forth in Yoo, J. et al. *J Biol Chem* (1993) 268:13034–13042; Yoo, J. et al. *J Biol Chem* (1991) 266:17741–17743; and Bielinska, M. et al. *J Cell Biol* (1990) 111:330a (all cited above) and in Matzuk, M. M. et al. *J Biol Chem* (1989) 264:2409–2414, Keene, J. L. et al. *J Biol Chem* (1989) 264:4769–4775; and Keene, J. L. et al. *Mol Endocrinol* (1989) 3:2011–2017.

Not only may the glycosylation sites per se be modified directly, but positions proximal to these sites are preferentially modified so that the glycosylation status of the mutant will be affected. For the α subunit, for example, variants in which amino acids between positions 50–60 are substituted, including both conservative and nonconservative substitutions, are favored, especially substitutions at positions 51, 53 and 55 because of their proximity to the glycosylation site at $Asn_{52}$.

Also preferred are mutants of the α subunit wherein lysine at position 91 is converted to methionine or glutamic acid.

Although the variants have been discussed in terms of variations in the individual subunits hereinabove, it will be recalled that the single chain forms of the dimer offer additional opportunities for modification. Specifically, regions that are critical to folding of the dimer may not be critical to the correct conformation of the single chain molecule and these regions are available for variation in the single chain form, although not described above in terms of individual members of the dimeric forms. Further, the single chain forms may be modified dramatically in the context of non-critical regions whose alteration and/or deletion do not affect the biological activity as described above.

While for human use, the human forms of the glycoprotein quartet are desirable, it should be noted that the corresponding forms in other vertebrates are useful in veterinary contexts. Thus, the FSH, TSH and LH subunits characteristic of bovine, ovine, equine, porcine, feline, canine, and other species are appropriate to indications affecting these species per se.

Suitable Drugs

Suitable drugs that may be included in the linker moiety include peptides or proteins such as insulin-like growth factors; epidermal growth factors; acidic and basic fibroblast growth factors; platelet-derived growth factors; the various colony stimulating factors, such as granulocyte CSF, macrophage-CSF, and the like; as well as the various cytokines such as IL-2, IL-3 and the plethora of additional interleukin proteins; the various interferons; tumor necrosis factor; and the like. Peptide- or protein-based drugs have the advantage that they can be included in the single-chain and the entire construct can readily be produced by recombinant expression of a single gene. Also, small molecule drugs such as antibiotics, antiinflammatories, toxins, and the like can be used.

In general, the drugs included within the linker moiety will be those desired to act in the proximity of the receptors to which the hormones ordinarily bind. Suitable provision for release of the drug from inclusion within the linker will be provided, for example, by also including sites for enzyme-catalyzed lysis as further described under the section headed Preparation Methods hereinbelow.

Other Modifications

The single-chain proteins of the invention may be further conjugated or derivatized in ways generally understood to derivatize amino acid sequences, such as phosphorylation, glycosylation, deglycosylation of ordinarily glycosylated forms, modification of the amino acid side chains (e.g., conversion of proline to hydroxyproline) and similar modifications analogous to those post-translational events which have been found to occur generally.

The glycosylation status of the hormones of the invention is particularly important. The hormones may be prepared in nonglycosylated form either by producing them in procaryotic hosts or by mutating the glycosylation sites normally present in the subunits and/or any CTP units that may be present. Both nonglycosylated versions and partially glycosylated versions of the hormones can be prepared by manipulating the glycosylation sites. Normally, glycosylated versions are, of course, also included within the scope of the invention.

As is generally known in the art, the single-chain proteins of the invention may also be coupled to labels, carriers, solid supports, and the like, depending on the desired application. The labeled forms may be used to track their metabolic fate; suitable labels for this purpose include, especially, radioisotope labels such as iodine 131, technetium 99, indium 111, and the like. The labels may also be used to mediate detection of the single-chain proteins in assay systems; in this instance, radioisotopes may also be used as well as enzyme labels, fluorescent labels, chromogenic labels, and the like. The use of such labels is particularly helpful for these proteins since they are targeting agents receptor ligand.

The proteins of the invention may also be coupled to carriers to enhance their immunogenicity in the preparation of antibodies specifically immunoreactive with these new modified forms. Suitable carriers for this purpose include keyhole limpet hemocyanin (KLH), bovine serum albumin (BSA) and diphtheria toxoid, and the like. Standard coupling techniques for linking the modified peptides of the invention to carriers, including the use of bifunctional linkers can be employed.

Similar linking techniques, along with others, may be employed to couple the proteins of the invention to solid supports. When coupled, these proteins can then be used as affinity reagents for the separation of desired components with which specific reaction is exhibited.

Preparation Methods

Methods to construct the proteins of the invention are well known in the art. As set forth above, if only gene encoded amino acids are included, and the single-chain is in a head-to-tail configuration, the most practical approach at present is to synthesize these materials recombinantly by expression of the DNA encoding the desired protein. DNA containing the nucleotide sequence encoding the single-chain forms, including variants, can be prepared from native sequences. Techniques for site-directed mutagenesis, ligation of additional sequences, PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available compatible with a wide variety of hosts, including procaryotic hosts such as bacteria and eucaryotic hosts such as yeast, plant cells, insect cells, mammalian cells, avian cells, and the like.

The choice of host is particularly to posttranslational events, most particularly including glycosylation. The location of glycosylation is mostly controlled by the nature of the glycosylation sites within the molecule; however, the nature of the sugars occupying this site is largely controlled by the nature of the host. Accordingly, a fine-tuning of the properties of the hormones of the invention can be achieved by proper choice of host.

A particularly preferred form of gene for the α subunit portion, whether the α subunit is modified or unmodified, is the "minigene" construction.

As used herein, the α subunit "minigene" refers to the gene construction disclosed in Matzuk, M. M. et al, *Mol Endocrinol* (1988) 2:95–100, in the description of the construction of pM$^2$/CG α or pM$^2$/α. This "minigene" is characterized by retention only of the intron sequence between exon 3 and exon 4, all upstream introns having been deleted. In the particular construction described, the N-terminal coding sequences which are derived from exon 2 and a portion of exon 3 are supplied from cDNA and are ligated directly through an XbaI restriction site into the coding sequence of exon 3 so that the introns between exons I and II and between exons II and III are absent. However, the intron between exons III and IV as well as the signals 3' of the coding sequence are retained. The resulting minigene can conveniently be inserted as a BamHI/BglII segment. Other means for construction of a comparable minigene are, of course, possible and the definition is not restricted to the particular construction wherein the coding sequences are ligated through an XbaI site. However, this is a convenient means for the construction of the gene, and there is no particular advantage to other approaches, such as synthetic or partially synthetic preparation of the gene. The definition includes those coding sequences for the α subunit which retain the intron between exons III and IV, or any other intron and preferably no other introns.

For recombinant production, modified host cells using expression systems are used and cultured to produce the desired protein. These terms are used herein as follows:

A "modified" recombinant host cell, i.e., a cell "modified to contain" with the recombinant expression systems of the invention, refers to a host cell which has been altered to contain this expression system by any convenient manner of introducing it, including transfection, viral infection, and so forth. "Modified" refers to cells containing this expression system whether the system is integrated into the chromosome or is extrachromosomal. The "modified" cells may either be stable with respect to inclusion of the expression system or not. In short, "modified" recombinant host cells with the expression system of the invention refers to cells which include this expression system as a result of their manipulation to include it, when they natively do not, regardless of the manner of effecting this incorporation.

"Expression system" refers to a DNA molecule which includes a coding nucleotide sequence to be expressed and those accompanying control sequences necessary to effect the expression of the coding sequence. Typically, these controls include a promoter. termination regulating sequences, and, in some cases, an operator or other mechanism to regulate expression. The control sequences are those which are designed to be functional in a particular target recombinant host cell and therefore the host cell must be chosen so as to be compatible with the control sequences in the constructed expression system.

If secretion of the protein produced is desired, additional nucleotide sequences encoding a signal peptide are also included so as to produce the signal peptide operably linked to the desired single-chain hormone to produce the preprotein. Upon secretion, the signal peptide is cleaved to release the mature single-chain hormone.

As used herein "cells," "cell cultures," and "cell lines" are used interchangeably without particular attention to nuances of meaning. Where the distinction between them is important, it will be clear from the context. Where any can be meant, all are intended to be included.

The protein produced may be recovered from the lysate of the cells if produced intracellularly, or from the medium if secreted. Techniques for recovering recombinant proteins from cell cultures are well understood in the art, and these proteins can be purified using known techniques such as chromatography, gel electrophoresis, selective precipitation, and the like.

All or a portion of the hormones of the invention may be synthesized directly using peptide synthesis techniques known in the art. Synthesized portions may be ligated, and release sites for any drug contained in the linker moiety introduced by standard chemical means. For those embodiments which contain amino acids which are not encoded by the gene and those embodiments wherein the head-to-head or tail-to-tail configuration is employed, of course, the synthesis must be at least partly at the protein level. Head-to-head junctions at the natural N-termini or at positions proximal to the natural N-termini may be effected through linkers which contain functional groups reactive with amino groups, such as dicarboxylic acid derivatives. Tail-to-tail configurations at the C-termini or positions proximal to the C-termini may be effected through linkers which are diamines, diols, or combinations thereof.

Antibodies

The proteins of the invention may be used to generate antibodies specifically immunoreactive with these new compounds. These antibodies are useful in a variety of diagnostic and therapeutic applications.

The antibodies are generally prepared using standard immunization protocols in mammals such as rabbits, mice, sheep or rats, and the antibodies are tittered as polyclonal antisera to assure adequate immunization. The polyclonal antisera can then be harvested as such for use in for example, immunoassays. Antibody-secreting cells from the host, such as spleen cells, or peripheral blood leukocytes, may be immortalized using known techniques and screened for production of monoclonal antibodies immunospecific with the proteins of the invention.

By "immunospecific for the proteins" is meant antibodies which are immunoreactive with the single-chain proteins, but not with the heterodimers per se within the general parameters considered to determine affinity or nonaffinity. It is understood that specificity is a relative term, and an arbitrary limit could be chosen, such as a difference in immunoreactivity of 100-fold or greater. Thus, an immunospecific antibody included within the invention is at least 100 times more reactive with the single-chain protein than with the corresponding heterodimers.

By "specifically immunoreactive" is meant that the antibodies react with the single chain forms of compounds of the invention and not with other molecules, even closely related ones, in measurable degree. Thus, although the antibodies of the invention will specifically bind the single chain forms, they would bind the corresponding dimer or the individual subunits to a significantly lesser degree.

Formulation

The proteins of the invention are formulated and administered using methods comparable to those known for the heterodimers corresponding to the single-chain form. Thus, formulation and administration methods will vary according to the particular hormone used. However, the dosage level and frequency of administration may be altered as compared to the heterodimer, especially if CTP units are present in view of the extended biological half life due to its presence.

Formulations for proteins of the invention are those typical of protein or peptide drugs such as found in *Remington's Pharmaceutical Sciences,* latest edition, Mack Publishing Company, Easton, Pa. Generally, proteins are administered by injection, typically intravenous, intramuscular, subcutaneous, or intraperitoneal injection, or using formulations for transmucosal or transdermal delivery. These formulations generally include a detergent or penetrant such as bile salts, fusidic acids, and the like. These formulations can be administered as aerosols or suppositories or, in the case of transdermal administration, in the form of skin patches.

Oral administration is also possible provided the formulation protects the peptides of the invention from degradation in the digestive system.

Optimization of dosage regimen and formulation is conducted as a routine matter and as generally performed in the art.

These formulations can also be modified to include those suitable for veterinary use as is generally known in the art.

Methods of Use

The single-chain peptides of the invention may be used in many ways, most evidently as substitutes for the heterodimeric forms of the hormones. Thus, like the heterodimers, the agonist forms of the single-chain hormones of the invention can be used in treatment of infertility, as aids in vitro fertilization techniques, and other therapeutic methods associated with the native hormones. These techniques are applicable to humans as well as to other animals. The choice of the single-chain protein in terms of its species derivation will, of course, depend on the subject to which the method is applied.

The single-chain hormones are also useful as reagents in a manner similar to the heterodimers.

In addition, the single-chain hormones of the invention may be used as diagnostic tools to detect the presence or absence of antibodies with respect to the native proteins in biological samples. They are also useful as control reagents in assay kits for assessing the levels of these hormones in various samples. Protocols for assessing levels of the hormones themselves or of antibodies raised against them are standard immunoassay protocols commonly known in the art. Various competitive and direct assay methods can be used involving a variety of labeling techniques including radio-isotope labeling, fluorescence labeling, enzyme labeling and the like.

The single-chain hormones of the invention are also useful in detecting and purifying receptors to which the native hormones bind. Thus, the single-chain hormones of the invention may be coupled to solid supports and used in affinity chromatographic preparation of receptors or antihormone antibodies. The resulting receptors are themselves useful in assessing hormone activity for candidate drugs in screening tests for therapeutic and reagent candidates.

Finally, the antibodies uniquely reactive with the single-chain hormones of the invention can be used as purification tools for isolation of subsequent preparations of these materials. They can also be used to monitor levels of the single-chain hormones administered as drugs.

The following examples are intended to illustrate but not to limit the invention.

Example 1

Preparation of DNA Encoding CGβ-α

FIG. 1 shows the construction of an insert for an expression vector wherein the C-terminus of the β-chain of human CG is linked to the N-terminus of the mature human α subunit.

As shown in FIG. 1, the polymerase chain reaction (PCR) is utilized to fuse the two subunits between exon 3 of CGβ and exon 2 of the α subunit so that the codon for the carboxy terminal amino acid of CGβ is fused directly in reading frame to that of the N-terminal amino acid of the α subunit. This is accomplished by using a hybrid primer to amplify a fragment containing exon 3 of CGβ wherein the hybrid primer contains a "tail" encoding the N-terminal sequence of the α subunit. The resulting amplified fragment thus contains a portion of exon 2 encoding human CGα.

Independently, a hybrid primer encoding the N-terminal sequence of the α subunit fused to the codons corresponding to the C-terminus of CGβ is used as one of the primers to amplify the α minigene. The two amplified fragments, each now containing overlapping portions encoding the other subunit are together amplified with two additional primers covering the entire span to obtain the SalI insert.

In more detail, reaction 1 shows the production of a fragment containing exon 3 of CGβ and the first four amino acids of the mature α subunit as well as a SalI site 5'-ward of the coding sequences. It is obtained by amplifying a portion of the CGβ genomic sequence which is described by Matzuk, M. M. et al. *Proc Natl Acad Sci USA* (1987) 84:6354–6358; Policastro, P. et al. *J Biol Chem* (1983) 258:11492–11499.

Primer 1 (SEQ ID NO:41) provides the SalI site and has the sequence:

```
5'-GGA GGA AGG GTG GTC GAC CTC TCT GGT-3'.
                    SalI
```

The other primer, primer 2 (SEQ ID NO:42), is complementary to four codons of the a N-terminal sequence and five codons of the CGβ C-terminal sequence and has the sequence:

```
5'-CAC ATC AGG AGC|TTG TGG GAG GAT CGG-3'.
              ←_α|β_→
```

The resultant amplified segment which is the product of reaction α thus has a SalI site 5'-ward of the fused coding region.

In reaction II, an analogous fused coding region is obtained from the α minigene described hereinabove. Primer 3 (SEQ ID NO:43) is a hybrid primer containing four codons of the β subunit and five codons of α and has the sequence:

```
5'-ATC CTC CCA CAA|GCT CCT GAT GTG CAG-3'.
              ←_β|α_→
```

Primer 4 (SEQ ID NO:44) contains a SalI site and is complementary to the extension of α exon 4. Primer 4 has the sequence:

```
5'-TGA GTC GAC ATG ATA ATT CAG TGA TTG AAT-3'.
        SalI
```

Thus, the products of reactions I and II overlap, and when subjected to PCR in the presence of primers 1 and 4 yield the desired SalI product as shown in reaction III.

The amplified fragment containing CGβ exon 3 and the α minigene is inserted into the SalI site of pM$^2$HA-CGβexon 1,2 an expression vector which is derived from pM$^2$ containing CGβ exons 1 and 2 in the manner described by Sachais, B., Snider, R. M., Lowe, J., Krause, J. *J Biol Chem* (1993) 268:2319. pM$^2$ containing CGβ exons 1 and 2 is described in Matzuk, M. M. et al. *Proc Nati Acad USA* (1987) 84:6354–6358 and Matzuk, M. M. et al. *J Cell Biol* (1988) 106:1049–1059.

This expression vector then will produce the single-chain form human CG wherein the C-terminus of the β subunit is directly linked to the N-terminus of the α subunit.

Example 2

Production and Activity of the Single-Chain Human CG

The expression vector constructed in Example 1 was transfected into Chinese hamster ovary (CHO) cells and production of the protein was assessed by immunoprecipitation of radiolabeled protein on SDS gels. The culture medium was collected and the bioactivity of the single-chain protein was compared to the heterodimer in a competitive binding assay with respect to the human LH receptor. In this assay, the cDNA encoding the entire human LH receptor was inserted into the expression vector pCMX (Oikawa. J. X-C et al. *Mol Endocrinol* (1991) 5:759–768). Exponentially growing 293 cells were transfected with this vector using the method of Chen, C. et al. *Mol Cell Biol* (1987) 7:2745–2752.

In the assay, the cells expressing human LH receptor ($2\times10^5$/tube) were incubated with 1 ng of labeled hCG in competition with the sample to be tested at 220° C. for 18 hours. The samples were then diluted 5-fold with cold Dulbecco's PBS (2 ml) supplemented with 0.1% BSA and centrifuged at 800×g for 15 minutes. The pellets were washed twice with D's PBS and radioactivity was determined with a gamma counter. Specific binding was 10–12% of the total labeled (iodinated) hCG added in the absence of sample. The decrease in label in the presence of sample measures the binding ability in the sample. In this assay, with respect to the human LH receptor in 293 cells, the wild-type hCG had an $ED_{50}$ of 0.47 ng and the single-chain protein had an $ED_{50}$ of 1.1 ng.

In an additional assay for agonist activity, stimulation of cAMP production was assessed. In this case, 293 cells expressing human LH receptors ($2\times10^5$/tube) were incubated with varying concentrations of the heterodimeric hCG or single-chain hCG and cultured for 18 hours. The extracellular cAMP levels were determined by specific radioimmunoassay as described by Davoren, J. B. et al. *Biol Reprod* (1985) 33:37–52. In this assay, the wild-type had an $ED_{50}$ of 0.6 ng/ml and the single-chain form had an $ED_{50}$ of 1.7 ng/ml. ($ED_{50}$ is 50% of the effective dose.)

Thus, in all cases, the behavior of both the wild-type and single-chain forms is similar.

Example 3

Additional Activity Assays

Figure 3:
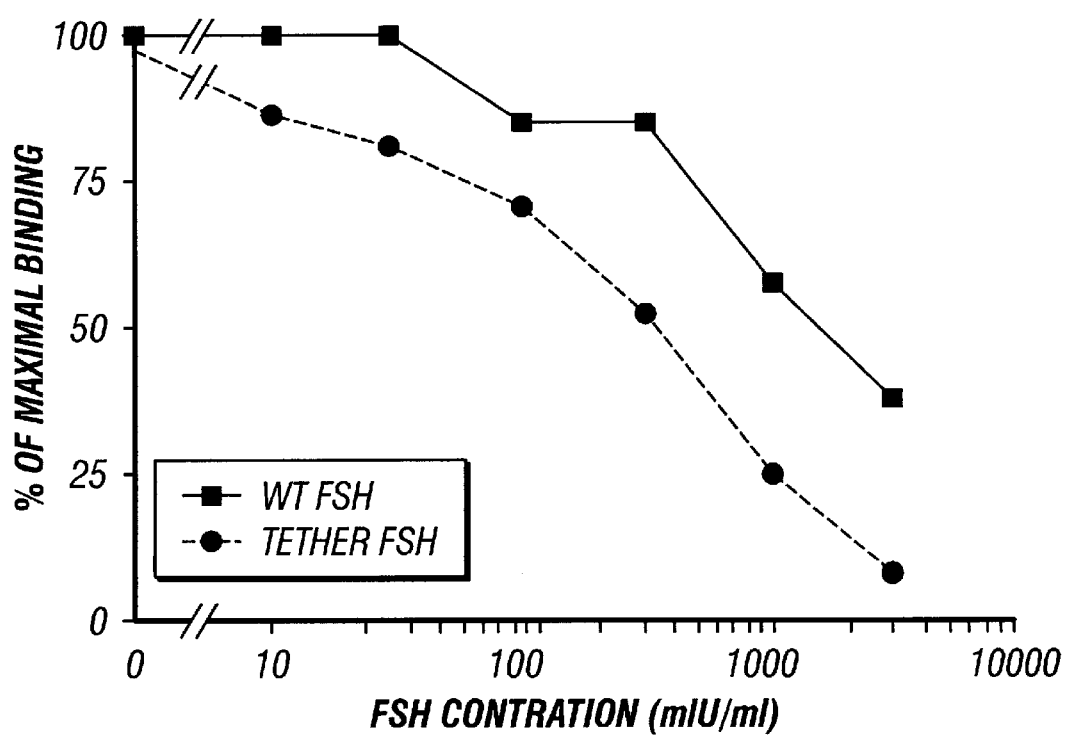
FIG. 3 shows the results of a competition binding assay for FSH receptor by various FSH analogs.

The medium from CHO cells transfected with an expression vector for the βFSH-CTP-α single-chain construct was recovered and assayed as described in Example 2. The results of the competition assay for binding to FSH receptor are shown in FIG. 3. The results indicate that the single-chain form is more effective than either wild-type FSH or FSH containing a CTP extension at the β chain in inhibiting binding of FSH itself to the receptor. The $ED_{50}$ for the single-chain form is approximately 50 mIU/ml while the $ED_{50}$ for the extended heterodimer is somewhat over 100 mIU/ml. That for wild-type FSH is about 120 mIU/ml.

Figure 4:
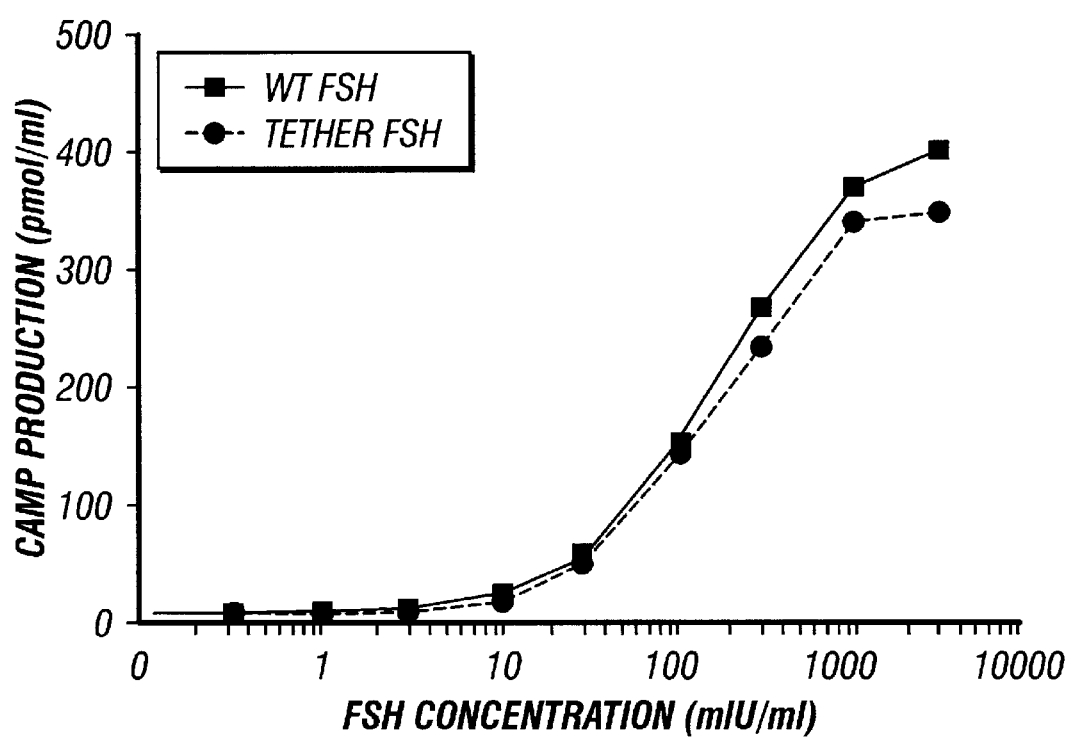
FIG. 4 shows the results of signal transduction assay with respect to FSH receptor for various FSH analogs.

The results of the signal transduction assay are shown in FIG. 4. The effectiveness of all three types of FSH is comparable.

Example 4

Construction of Additional Expression Vectors

In a manner similar to that set forth in Example 1, expression vectors for the production of single-stranded FSH, TSH and LH (βFSH-α, βFSH-CTP-α, βTSH-α, βTSH-CTP-α, βLH-α, βLH-CTP-α) are prepared and transfected into CHO cells. The resulting hormones show activities similar to those of the wild-type form, when assayed as set forth in Example 2.

The following documents are cited in the examples set forth below:
37. Moyle, W. R. et al. *J Biol Chem* (1975) 250:9163–9169.
54. Campbell, R. K. et al. *Mol Cell Endocrinol* (1992) 83:195–200.
64. Campbell, R. K. et al. *Proc Nati Acad Sci USA* (1991) 88:760–764.
65. Skaf, R. et al. *Endocrinology* (1985) 117:106–113.

Single chain gonadotropins with lutropin and/or folliotropin activity. The single-chain gonadotropins prepared in the following examples and additional illustrative gonadotropins are set forth in Table 1. The biological activity of these gonadotropins is set fort in Table 2. These appear at the end of the specification herein.

Example 5

Preparation and Use of Analog #1 (c.f, Table 1) a Single Chain Gonadotropin With Lutropin Activity See FIG. 5

The coding sequences for analog #1 listed in Table 1 can be synthesized using the block ligation approach described (54) or they can be prepared starting with the coding sequences for the hCG β-subunit and the human α-subunit. These can be cloned from a human placental cDNA library. The sequences encoding the signal peptide from the human α-subunit are deleted and the coding sequences for the proteins are spliced together using the SOEing technique (63) as follows: Primer #1 (SEQ ID NO:45) (100 ng) having the sequence 5'-ATGAAATCGACGGAATCAGACTCGAGCCAAGGA TGGAGATGTTCCAGGGGCT GCT-3' and primer #2 (SEQ ID NO:46) (100 ng) having the sequence 3'-GGGAGCCTGTGGGGCTAGGAGGGGGTTCCTAGG CCATCGCCTAGACCATCG-5' are mixed with the hCG β-subunit cDNA (1 μg) which serves as a template and PCR is performed for 25 temperature cycles of 94° C. (30 seconds), 50° C. (60 seconds), 72° C. (60 seconds) using Pfu DNA polymerase purchased from Strategene, LaJolla, Calif. and dioxynucleotide triphosphates and PCR buffer as described (63). Primer #3 (SEQ ID NO:47) (100 ng) having the sequence 5'-GGATCCGGTAGCGGATCTGGTAGCGCTCCTGATG TGCAGGATTGCCCA-3' and primer #4 (SEQ ID NO:48) (100 ng) having the sequence 3'-ACGTCATGAACAATAATAGTGTTTAGAATTCCATG GCCTAGGTAGAGTTCGAT TAGGCCT-5' are mixed with human α-subunit cDNA (1 μg) which serves as a template and PCR is performed for 25 temperature cycles of 94° C. (30 seconds), 50° C. (60 seconds), 72° C. (60 seconds) using Pfu DNA polymerase and dioxynucleotide triphosphates and PCR buffer as described (63). These two PCR reactions give products that serve as intermediate templates in a third (final) PCR reaction that gives the desired constructs in a form suitable for cloning. The final PCR reaction is performed by mixing 1 μl of the products from the first two PCR reactions alone with primer #5 (SEQ ID NO:49) having the sequence 5'-ATGAAATCGACGGAATCAGACTCGAGCCAAGG-3' and primer #6 (SEQ ID NO:50) having the sequence 3'-ATTCCATGGCCTAGGTAGAGTTCGATTAGGCCT-5' for 25 temperature cycles of 94° C. (30 seconds), 50° C. (60 seconds), 72° C. (60 seconds) using Pfu DNA polymerase additional dioxynucleotide triphosphates, and PCR buffer. The final PCR product is digested with restriction enzymes XhoI and BglII and ligated into pSVL (an expression vector obtained from Pharmacia, Piscataway, N.J.) that has been digested with XhoI and bamHI to create a vector that will direct the synthesis of Analog 1. The XhoI site of the PCR product will ligate to the XhoI site of pSVL and the BglII site of the PCR product will ligate to the BamHI site of pSVL. The XhoI site will be regenerated and the BglII and BamHI sites will be eliminated. The sequences of the coding regions (i.e., between the XbaI and KpnI sites, c.f, FIG. 6) of several constructs are determined until one is found that encodes a protein having the desired amino acid sequence illustrated in FIG. 6. This is done to eliminate the possible errors that arise as the result of PCR and other DNA manipulation and is a standard precaution to be certain that the desired sequence is obtained. The expressed protein is expected to lack amino acid residues MEM-FQGLLLLLLLSMGGTWA (SEQ ID NO:51) that are the part of the signal sequence found in hCG β-subunit and which are removed by the cell during protein synthesis. This vector is expressed in COS-7 cells as described (64) and the protein released into the medium is tested for its ability to inhibit the binding of radiolodinated hCG to monoclonal antibodies or to antisera prepared against hCG. The protein made by the COS-7 cells will compete with radioiodinated hCG for binding to one or more of the following antibodies: B101 (obtained from Columbia University), B105 (obtained from Columbia University), B107 (obtained from Columbia University), B109 (obtained from Columbia University), A201 (obtained from Columbia University), HCU061 (obtained from Hybritech), HCZ107 (obtained from Hybritech), or HCO514 (obtained from Hybritech), ZMCG18 (obtained from Pierce), ZMCGI 3 (obtained from Pierce), or ZMCG7 (obtained from Pierce) or 518B7 (obtained from Dr. Janet Roser, University of California at Davis). The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog would also be expected to be a good starting point for use in a contraceptive vaccine using the template approach outlined in Example 11. This analog is shown in Table 1 as Analog #1 and contains a linker sequence of GSGSGSGS (SEQ ID NO:52) . This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the ApaI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 6

Preparation and Use of Analog #2, a Single Chain Gonadotropin with Lutropin Activity See FIG. 6

The coding sequences for Analog #2 listed in Table 1 can be synthesized using the block ligation approach described (54) or they can be prepared by PCR using primers #1 and #7 and the expression construct described in Example 5 and in FIG. 5 as a template. The sequence of primer #7 (SEQ ID NO:53) is 3'-TGGTGGGGAACTGGACACTACTGGGCGCCCCTA GGCCATCG-5'. The final PCR product is digested with restriction enzymes XhoI and BamHI and ligated with the large fragment of DNA obtained by digesting the expression construct described in Example 12 with XhoI and BamHI. The sequences of the coding regions between the XhoI and BamHI sites of several constructs are determined until one is found that encodes a protein having the amino acid sequence described in FIG. 7 is obtained. This will insure that cloning artifacts are not present in the region that has been altered. The expressed protein is expected to lack amino acid residues MEMFQGLLLLLLLSMGGTWA (SEQ ID NO:51) that are the part of the signal sequence found in hCG β-subunit and which are removed by the cell during protein synthesis. This vector is expressed in COS-7 cells and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies: B101 (obtained from Columbia University), B105 (obtained from Columbia University), B107 (obtained from Columbia University), B109 (obtained from Columbia University), A201 (obtained from Columbia University), HCU061 (obtained from Hybritech), or HCO514 (obtained from Hybritech), ZMCG18 (obtained from Pierce), ZMCG13 (obtained from Pierce), or ZMCG7 (obtained from Pierce) or 518B7 (obtained from Dr. Janet Roser, University of California at Davis). The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog would also be expected to be a good starting point for use in a contraceptive vaccine using the template approach outlined in Example 11. This analog is shown in Table 1 as Analog #2 and contains a linker sequence of GSGSGSGS (SEQ ID NO:52). This linker can be modified by digesting the expression vector with SstII and Eco47III endonuclease restriction enzymes, discarding the short piece, ligating a cassette of synthetic double stranded DNA with the desired amino acid codons containing any number of glycine or serine codons or other amino acid codons into the SstII/Eco47III site by standard methods sequencing the region between the SstII/Eco47III to confirm the desired mutations have been made, and expressing the protein in COS-7 cells.

This can be done to optimize the activity of the single chain gonadotropin. The protein is expected to function as a monomer or to combine to form active homodimers. In addition, several copies of the protein would be expected to combine to form multimers.

Example 7

Preparation and Use of Analog #3, a Single Chain Gonadotropin with Lutropin Activity See FIG. 7

The coding sequences for analog #3 listed in Table 1 can be synthesized using the block ligation approach described (54) or they can be prepared in the fashion as described for Analog #2 in Example 6 except that primers #1 and #7 are replaced with primers #8 and #9 and that the hLH β-subunit cDNA is used as a template in place of the hCG β-subunit cDNA. The hLH β-subunit cDNA can be obtained by screening a human pituitary library. The sequence of primer #8 (SEQ ID NO:54)is 5'-ATGAAATCGACGGAATCAGACTCGAGCCAAGGA ATGGAGATGCTCCAGGGGC TGCT-3' and the sequence of primer #9 (SEQ ID NO:55) is 3'-GTGGGGAACTGGACACTGGTGGGGGTTCCTAGG CCATCGCCTAGACCATCG-5'. The final PCR product is digested with restriction enzymes XhoI and BamHI and subcloned into the XhoI/BamHI sites of the expression vector created as described in Example 12. The sequences of the coding regions between the XhoI and BamHI sites of several constructs are determined until one is found that encodes a protein having the amino acid sequence shown in FIG. 8. The expressed protein is expected to lack amino acid residues MEMLQGLLLLLLLSMGGAWA (SEQ ID NO:56) that are the part of the signal sequence found in hLH β-subunit and which are removed by the cell during protein synthesis. This vector is expressed in COS-7 cells and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies: B101 (obtained from Columbia University), B105 (obtained from Columbia University), A201 (obtained from Columbia University), HCU061 (obtained from Hybritech), ZMCG7 (obtained from Pierce) or 518B7 (obtained from Dr. Janet Roser, University of California at Davis). The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog would also be expected to be a good starting point for use in designing vaccines to enhance or inhibit fertility using the template procedure outlined earlier. This analog is shown in Table 1 as Analog #3 and contains a linker sequence of GSGSGSGS (SEQ ID NO:52). This linker can be modified by digesting the expression vector with BamHI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the BamHI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 8

Preparation and Use of Analog #4, a Single Chain Gonadotropin with Follitropin Activity

See FIG. 8

The coding sequences for analog #4 listed in Table 1 can be synthesized using the block ligation approach described (54) or they can be prepared in the fashion as described for Analog #2 in Example 13 except that primers #1 and #7 are replaced with primers #10 and #11 and that the hFSH β-subunit cDNA is used as a template in place of the hCG β-subunit cDNA. The hFSH β-subunit cDNA can be obtained from a human pituitary gland library. The sequence of primer #10 (SEQ ID NO:57) is 5'-ATGAAATCGACGGAATCAGACTCGAGCCAAGGA TGAAGACACTCCAGTTTTTC TTCC-3' and the sequence of primer #11 (SEQ ID NO:58) is 3'-GACGAGGAAACCACTTTACTTTCTTCCTAGGCCA TCGCCTAGACCA-5'. The final PCR product is digested with restriction enzymes XhoI and BamHI and subcloned into the XhoI/BamHI sites of the expression vector created as described in Example 12. The sequences of the coding regions between the XbaI and BamHI sites of several constructs are determined until one is found that encodes a protein having the amino acid sequence illustrated in FIG. 9. The expressed protein is expected to lack amino acid residues MKTLQFFFLFCCWKAICC that are the part of the signal sequence found in hFSH β-subunit and which are removed by the cell during protein synthesis. The vector is expressed in COS-7 cells and the protein made by the cells will compete with radioiodinated hFSH for binding to one or more of the following antibodies: ZMFS 1 (obtained from Pierce), A201 (obtained from Columbia University), HCU061 (obtained from Hybritech), FSG761 (obtained from Hybritech), FSR093.3 (obtained from Hybritech), FSH107 (obtained from Hybritech), FSB061 (obtained from Hybritech), FSM210 (obtained from Hybritech), and FSM268 (obtained from Hybritech). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. This analog is also a useful starting compound to select for an immunogen that elicits antibodies to FSH and is part of a contraceptive vaccine. This analog is shown in Table 1 as Analog #4 and contains a linker sequence of GSGSGSGS (SEQ ID NO:52). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 9

Preparation and Use of Analog #5, a Single Chain Gonadotropin with FSH Activity That is Structurally More Similar to hCG Than hFSH

See FIG. 9

The coding sequences for analog #5 listed in Table 1 can be synthesized using the block ligation approach described (54) or they can be prepared in the fashion as described for Analog #2 in Example 6 except that primer #7 is replaced with primer #12. The sequence of primer #12 (SEQ ID NO:60) is 3'-CGACAGTCGACAGTTACACGTGAGACGCTGTCG CTGTCGTGACTAACATGACA CGCTCCGGAC- CCCGGGTCGATGACGAGGAAACCACTT- TACTTTCTTCCTAGGC CATCG-5'. The final PCR product is digested with restriction enzymes XhoI and BamHI and subcloned into the XhoI/BamHI sites of the expression vector created as described in Example 12. The sequences of the coding regions between the XbaI and BamHI sites of several constructs are determined until one is found that encodes a protein having the amino acid sequence illustrated in FIG. 10. The expressed protein is expected to lack amino acid residues MEMLQGLLLLLLLSMGGAWA (SEQ ID NO:56) that are the part of the signal sequence found in hCG β-subunit and which are removed by the cell during protein synthesis. This vector is expressed in COS-7 cells and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies: B101 (obtained from Columbia University), B105 (obtained from Columbia University), B107 (obtained from Columbia University), B109 (obtained from Columbia University), A201 (obtained from Columbia University), HCU061 (obtained from Hybritech), or HCO514 (obtained from Hybritech), ZMCG18 (obtained from Pierce), ZMCG13 (obtained from Pierce), or ZMCG7 (obtained from Pierce) or 518B7 (obtained from Dr. Janet Roser, University of California at Davis). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. This analog is shown in Table 1 as Analog #5 and contains a linker sequence of GSGSGSGS (SEQ ID NO:52). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 10

Preparation and Use of Analog #6, a Single Chain Gonadotropin with FSH and LH Activities That is Structurally More Similar to hCG Than hFSH

See FIG. 10

The coding sequences for analog #6 listed in Table 1 can be synthesized using the block ligation approach described (54) or they can be prepared in the fashion as described for Analog #2 in Example 6 except that primer #7 is replaced with primer #13. The sequence of primer #13 (SEQ ID NO:61) is 3'-ACGGCGGCGTCGTGGTGACTGACGTGACACGCT CCGGACCCCGGGTCGATGA CGAGGAAACCACTTTACTTTCTTCCTAGGCCATCG-5'. The final PCR product is digested with restriction enzymes XhoI and BamHI and subcloned into the XhoI/BamHI sites of the expression vector created as described in Example 12. The sequences of the coding regions between the XbaI and BamHI sites of several constructs are determined until one is found that encodes a protein having the amino acid sequence illustrated in FIG. 11. The expressed protein is expected to lack amino acid residues MEM-LQGLLLLLLLSMGGAWA (SEQ ID NO:56) that are the part of the signal sequence found in hCG-subunit and which are removed by the cell during protein synthesis. This vector is expressed in COS-7 cells and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies: B107 (obtained from Columbia University), B105 (obtained from Columbia University), B107 (obtained from Columbia University), B109 (obtained from Columbia University), A201 (obtained from Columbia University), HCU061 (obtained from Hybritech), or HCO514 (obtained from Hybritech), ZMCG18 (obtained from Pierce), ZMCG13 (obtained from Pierce), or ZMCG7 (obtained from Pierce) or 518B7 (obtained from Dr. Janet Roser, University of California at Davis). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog is shown in Table 1 as Analog #6 and contains a linker sequence of GSGSGSGS (SEQ ID NO:52). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 11

Preparation and Use of Analog #7, a Single Chain Gonadotropin with FSH and LH Activities That is Structurally More Similar to hCG Than hFSH The coding sequences for analog 47 listed in Table 1 can be synthesized using the block ligation approach described (54) or they can be prepared in the fashion as described for Analog #2 in Example 6 except that primer #7 is replaced with primer #14. The sequence of primer #14 (SEQ ID NO: 62) is 3'-ACGGCGGCGTCGTGGTGACTGACGTGACACGCT CCGGACCCCGGGTCGATGA CGAGGAAACCACTTCCTAGGCCATCG-5'. The final PCR product is digested with restriction enzymes XhoI and BamHI and subcloned into the XhoI/BamHI sites of the expression vector created as described in Example 12. The sequences of the coding regions between the XbaI and BamHI sites of several constructs are determined until one is found that encodes a protein having the amino acid sequence illustrated in FIG. 12. The expressed protein is expected to lack amino acid residues MEM-LQGLLLLLLLSMGGAWA (SEQ ID NO:56) that are the part of the signal sequence found in hCG β-subunit and which are removed by the cell during protein synthesis. This vector is expressed in COS-7 cells and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies. B101 (obtained from Columbia University), B105 (obtained from Columbia University), B107 (obtained from Columbia University), B109 (obtained from Columbia University), A201 (obtained from Columbia University), HCU061 (obtained from Hybritech), or HCO514 (obtained from Hybritech), ZMCG18 (obtained from Pierce), ZMCG-13 (obtained from Pierce), or ZMCG7 (obtained from Pierce) or 518B7 (obtained from Dr. Janet Roser, University of California at Davis). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog is shown in Table 1 as Analog #17 and contains a linker sequence of GSGSGSGS (SEQ ID NO:52). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 12

Preparation and Use of Analog #8, a Single Chain Gonadotropin with FSH and LH Activities That is Structurally More Similar to hCG Than hFSH See FIG. 12

The coding sequences for analog #8 listed in Table 1 can be synthesized using the block ligation approach described (54) or they can be prepared in the fashion as described for Analog #2 in Example 6 except that primer #7 is replaced with primer #15. The sequence of primer #15 (SEQ ID NO:63) is 3'-ACGGCGGCGTCGTGGTGACTGACGTGACACGCT CCGGACCCCGGGTCGATGA CGCTACTGGGCGCCCCTAGGCCATCG-5'. The final PCR product is digested with restriction enzymes XhoI and BamHI and subcloned into the XhoI/BamHI sites of the expression vector created as described in Example 5. The sequences of the coding regions between the XbaI and BamHI sites of several constructs are determined until one is found that encodes a protein having the amino acid sequence illustrated in FIG. 6. The expressed protein is expected to lack amino acid residues MEM-LQGLLLLLLLSMGGAWA (SEQ ID NO:56) that are the part of the signal sequence found in hCG β-subunit and which are removed by the cell during protein synthesis. This vector is expressed in COS-7 cells and the protein released into the medium is tested for its ability to inhibit the binding of radioiodinated hCG to monoclonal antibodies or to antisera prepared against hCG. The protein made by the COS-7 cells will compete with radioiodinated hCG for binding to one or more of the following antibodies. B1010 (obtained from Columbia University), B105 (obtained from Columbia University), B107 (obtained from Columbia University), B109 (obtained from Columbia University), A201 (obtained from Columbia University), HCU061 (obtained from Hybritech), or HCO514 (obtained from Hybritech), ZMCG18 (obtained from Pierce), ZMCG13 (obtained from Pierce), or ZMCG7 (obtained from Pierce) or 518B7 (obtained from Dr. Janet Roser, University of California at Davis). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. The protein released into the medium will compete with radiolabeled hCG for binding to receptors on corpora lutea as described by Campbell, Dean-Emig, and Moyle (64). It would be expected to stimulate testosterone formation in a Leydig cell assay performed similar to that described by Moyle et al. (37) and to stimulate ovulation in female animals and to stimulate testosterone formation in male mammals. This analog is shown in Table 1 as Analog #8 and contains a linker sequence of GSGSGSGS (SEQ ID NO:52). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 13

Preparation and Use of Analog #9, a Single Chain Gonadotropin with Follitropin Activity See FIG. 13

The coding sequences for analog #9 listed in Table 1 can be synthesized using the block ligation approach described (54) or they can be prepared by digesting the construct described in Example 8 used to express Analog 4 with the restriction enzymes ApaI and BamHI. The small piece is replaced with a cassette of synthetic DNA to give the sequence illustrated in FIG. 13. The coding sequence between the ApaI and BamHI sites of several constructs is determined until one is found that encodes a protein having the amino acid sequence illustrated in FIG. 13. The expressed protein is expected to lack amino acid residues MKTLQFFFLFCCWKAICC (SEQ ID NO:59) that are the part of the signal sequence found in hFSH β-subunit and which are removed by the cell during protein synthesis. The vector is expressed in COS-7 cells and the protein made by the cells will compete with radioiodinated hFSH for binding to one or more of the following antibodies ZMFS1 (obtained from Pierce), A201 (obtained from Columbia University). HCU061 (obtained from Hybritech), FSG761 (obtained from Hybritech), FSR093.3 (obtained from Hybritech), FSH107 (obtained from Hybritech), FSB061 (obtained from Hybritech), FSM210 (obtained from Hybritech), and FSM268 (obtained from Hybritech). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. This analog is also a useful starting compound to select for an immunogen that elicits antibodies to FSH and is part of a contraceptive vaccine. This analog is shown in Table 1 as Analog #9 and contains a linker sequence of GSGSGSGS (SEQ ID NO:52). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 14

Preparation and Use of Analog #10, a Single Chain Gonadotropin with Follitropin Activity See FIG. 14

The coding sequences for Analog #10 listed in Table 1 can be synthesized using the block ligation approach described (54) or they can be prepared by digesting the construct described in Example 8 used to express Analog 4 with the restriction enzymes ApaI and BamHI. The small piece is replaced with a cassette of synthetic DNA to give the sequence illustrated in FIG. 14. The coding sequence between the ApaI and BamHI sites of several constructs is determined until one is found that encodes a protein having the amino acid sequence illustrated in FIG. 14. The expressed protein is expected to lack amino acid residues MKTLQFFFLFCCWKAICC (SEQ ID NO:59) that are the part of the signal sequence found in hFSH β-subunit and which are removed by the cell during protein synthesis. The vector is expressed in COS-7 cells and the protein made by the cells will compete with radioiodinated hFSH for binding to one or more of the following antibodies: ZMFS1 (obtained from Pierce), A201 (obtained from Columbia University), HCU061 (obtained from Hybritech), FSG761 (obtained from Hybritech), FSR093.3 (obtained from Hybritech), FSH 107 (obtained from Hybritech), FSB061 (obtained from Hybritech), FSM210 (obtained from Hybritech), and FSM268 (obtained from Hybritech). The protein released into the medium will compete with hFSH for binding to receptors on bovine testes as described by Campbell, Dean-Emig, and Moyle (64). It would be expected to stimulate estradiol formation in a granulosa cell assay performed similar to that described by Skaf et al (65) and to stimulate follicle development and spermatogenesis in female and male mammals. This analog is also a useful starting compound to select for an immunogen that elicits antibodies to FSH and is part of a contraceptive vaccine. This analog is shown in Table 1 as Analog #10 and contains a linker sequence of GSGSGSGS (SEQ ID NO:52). This linker can be modified by digesting the expression vector with ApaI and Eco47III endonuclease restriction enzymes, discarding the short piece, ligating a cassette of synthetic double stranded DNA with the desired amino acid codons containing any number of glycine or serine codons or other amino acid codons into the BamHI/Eco47III site by standard methods, sequencing the region between the ApaI/Eco47III to confirm the desired mutations have been made, and expressing the protein in COS-7 cells. This can be done to optimize the activity of the single chain gonadotropin. The protein is expected to function as a monomer or to combine to form active homodimers. In addition, several copies of the protein would be expected to combine to form multimers.

Example 15

Preparation of an α-subunit Analog Lacking Glycosylation Sites

See FIG. 15

Analogs1–10 are expected to contain 4 asparagine-linked oligosaccharides since they contain 4 sets of codons for the sequence Asparagine-X-Threonine/Serine where X is any amino acid except proline. Removal of the asparagine-linked oligosaccharides, particularly those of the α-subunit, has been shown to reduce hormone efficacy. The asparagine-linked glycosylation signals can be removed from the α-subunit portion of the single chain gonadotropins using PCR as described here. PCR primer 16 (SEQ ID NO:64) having the sequence: 5'-TGCTTCTCTAGAGCATATCCCACTCCACTAAGGTC CAAGAAGACGATGTTGGT CCAAAAGCAAGTCACCT-3' and PCR primer 17 (SEQ ID NO:65) having the sequence:3'-CAAAGTTTCACCTCGTTGTGTGCCG-CACGGTGACGTCATGAACAATAATAGTG TTTAGAATTCCATGGCCATG-5' are used in a PCR reaction with a the vector that is capable of directing the expression of Analog1 and that was described in Example 5 and FIG. 5. After 25 cycles in the conditions described in Example 5, the PCR product and the expression vector are digested with XbaI and KpnI. The small fragment produced by digestion of the vector is discarded and the digested PCR product is ligated into the vector in its place. This produces an expression vector that encodes Analog 11, an analog that contains only 2 Asn-linked glycosylation signals but that is expected to retain its affinity for antibodies and antisera that bind to hCG. It is also expected to retain its affinity for LH receptors as shown by its ability to compete with hCG for binding to membranes from rat corpora lutea. However, it is expected to have a reduced ability to induce signal transduction, especially when its ability to elicit cyclic AMP accumulation is tested (37). It is possible to create similar derivatives of Analogs 2–10 in which the oligosaccharides are removed from the portion of the protein derived from the α-subunit by digesting each of the expression vectors with BamHI and KpnI, discarding the smaller piece, and ligating the small BamHI/KpnI fragment obtained by digestion of Analog 1I. Thus, Analog 2 would become Analog 12, Analog 3 would become Analog 13, Analog 4 would become Analog 14, Analog 5 would become Analog 15, Analog 6 would become Analog 16, Analog 7 would become Analog 17, Analog 8 would become Analog 18, Analog 9 would become Analog 19, and Analog 10 would become Analog 20. Note that it would also be possible to remove only one of the two glycosylation signals on the portion of the single chain gonadotropins derived from the α-subunit simply by changing the sequences of primers 16 and, 17 during their synthesis and following the protocol outlined here. Each of these analogs would exhibit the same antibody and receptor binding as their precursors. They would have reduced efficacy and as a consequence, they would inhibit signal transduction. Analogs 11, 12, and 13 would reduce the activity of LH and would stimulate fertility when given in the early part of the follicular phase of the menstrual cycle. They would reduce the activity of hCG and would prevent fertility when administered near the time of expected menses.

Example 16

Preparation of Analog1a Lacking Asparagine-linked Oligosaccharides

See FIGS. 16 and 17

The efficacy of gonadotropins is proportional to their content of carbohydrates and while Analogs 11, 12, 13 14, 15, 16, 17, 18, 19, and 20 have lower efficacy, it is possible to reduce their efficacy further by eliminating all oligosaccharide chains. The asparagine-linked oligosaccharide chains can be eliminated from Analog 11 by PCR SOEing (63) using primers 1 and 18 in one reaction and primers 2 and 19 in a second reaction. The expression vector for Analog 11 serves as a template in both reactions. The sequence of primer #18 (SEQ ID NO:66) is 5'-CGGGGTAGGTTCGGTGGGACCGACACCTCTTCC TCCCGACGGGG-3' and the sequence of primer #19 (SEQ ID NO:67) is 3'-GTGGAGAAGGAGGGCTGCCCCGTGTGCATCACC GTCAACACCACCATC-5'. After 25 temperature cycles at 94° C. (30 sec), 55° C. (60 sec), and 72° C. (60 sec), each PCR reaction is mixed with primer #5 and additional primer #2, new buffer, enzyme, and deoxynucleotide triphosphates. The reaction product after 25 additional cycles is cut with XhoI and BamHI and substituted for the original DNA found between the XhoI/BamHI sites of the vector encoding Analog 11. This is accomplished by digesting the vector with XhoI and BamHI, discarding the small fragment and then ligating the large fragment with the XhoI/BamHI digested PCR product. Several clones are subjected to DNA sequencing until the one encoding the analog outlined in FIG. 18 termed Analog 1a is obtained. When this is expressed in COS-7 cells, the protein that is made will be recognized by the same antibodies and antisera as Analog 1. Analog 1a will also bind to lutropin receptors but will have reduced efficacy relative to hCG. Thus, it will be useful for reducing the function of LH or hCG. When administered early in the follicular phase of the menstrual cycle, Analog 1a will reduce androgen synthesis. As a consequence. estradiol synthesis will decline, FSH levels will rise and fertility will be stimulated. Analog, 1a will also be useful for inhibiting premature luteinization of the follicle. When administered in the luteal phase at about the time of expected menses, the analog will block the actions of hCG and serve as a menses inducer and an inhibitor of fertility.

Analog 1a will also serve as a good starting compound to design vaccines using the template strategy described earlier.

Example 17

Preparation of Other Gonadotropins Lacking Asparagine-linked Oligosaccharides

The coding vectors for Analogs 2a, 5a, 6a, 7a, and 8a are readily prepared from Analog 1a and Analogs 12, 15, 16, 17, and 18. Analog 1a is digested with KpnI and MstII and the small fragment discarded. The large fragment is ligated separately to the small fragment prepared by KpnI-MstII digestion of the coding vectors for Analogs 12, 15, 16, 17, and 18. Analogs 2a, 5a, 6a, 7a, and 8a will bind the same antibodies and receptors as Analogs 2, 5, 6, 7, and 8, respectively. However, their abilities to elicit signal transduction will be reduced. Consequently, they will serve as inhibitors. Analog 2a will be effective primarily in blocking binding of hormones to LH receptors. Depending on the time that it is administered, Analog 2a will elicit fertility (i.e., when given early in the menstrual cycle) or will inhibit fertility (i.e., when given near the time of implantation or expected menses). In this regard Analogs 1a and 2a will have similar activities. Analog 5a will be effective primarily in blocking binding of hormones to FSH receptors. Analog 5a will be useful for suppressing hyperovarian stimulation. Analogs 6a, 7a, and 8a will be inhibitors of binding to LH and FSH receptors. These will be useful for suppressing hyperovarian stimulation and for blocking premature luteinization.

The coding vectors for Analogs 3a and 4a can be made by SOEing PCR (63) in which Analogs 13 and 14 serve as templates. The strategy for design of the primers is similar as that described for the preparation of primers used to modify the expression vector for Analog 1a. When Analogs 3a and 4a are expressed in COS-7 cells, the proteins that are made will be recognized by the same antibodies and antisera as Analogs 3 and 4, respectively. Analog 3a will be useful for inhibiting the activity of hormones that bind to LH receptors. As such it will stimulate fertility when given early in the follicular phase. Analog 4a will be useful for inhibiting the activity of FSH. Analog 3a will be useful as a starting molecule for designing the vaccine to be used to increase fertility using the template strategy and antibodies that are able to partially neutralize the activity of LH. Analog 3a will also be useful as a starting molecule for designing the vaccine to prevent fertility using the template strategy and antibodies that are able to neutralize LH activity. Antibody 4a will also be useful as a starting molecule for designing the anti-FSH vaccine described earlier using the template strategy.

The coding vectors for Analogs 9a and 10a can be prepared from the coding vector for Analog 4a. The coding vector for Analog 4a is digested with BalI and KpnI and the small fragment discarded. The small BalI-KpnI fragments from the coding vectors for analogs 19 and 20 are ligated separately with the large Analog 4a fragment to produce coding vectors for Analogs 9a and 10a. When produced in COS-7 cells, Analogs 9a and 10a will have similar antibody and FSH receptor binding specificities as Analogs 9 and 10. Analogs 9a and 10a will have lower efficacy and will inhibit the activity of FSH. Thus, they will be useful for reducing ovarian hyperstimulation. They will also be useful starting vectors for the design of anti-FSH vaccines using the template strategy.

Example 18

Typical Procedure for Introducing a Glycosylation Site in a Gonadotropin

Due to the positive influence of oligosaccharide residues on the stability of hormones in circulation, it is often useful to add extra oligosaccharide chains to the proteins. Addition of oligosaccharides can also be used to prevent unwanted antibody or receptor interactions. Surfaces of the protein that do not interact with receptors are useful places to add oligosaccharide chains that are to be used to stimulate hormone function. This can have a valuable effect in modulating the activities of single chain glycoprotein hormones or of modulating the activities of the Â,β-heterodimeric glycoprotein hormones. For example, addition of a glycosylation signal to FSH β-subunit at residues 71–73 to cause the creation of an asparagine-linked oligosaccharide at residue 71 will lead to a hormone that has higher activity. Conversely, addition of a glycosylation residue in this region of the protein after the other glycosylations have been removed will enhance its inhibitory activity. Methods for performing the mutagenesis are standard in the art and range from total synthesis of the coding sequences by block ligation of synthetic oligonucleotides (54) to SOEing PCR (63). Several examples of mutagenesis by SOEing PCR have already been given.

Example 19

Use of Sequences Other Than Those Derived From Human Subunits

Analogs 1–20, Analogs1b–10b and, in particular, Analogs 1A–10a will serve as useful starting compounds for template directed vaccine design. For development of hormone-specific vaccines for use in humans, it is useful to make analogs similar to those listed in Table 1 with a nonhuman α-subunit in place of the human α-subunit. This is because the bovine α-subunit renders the proteins more dissimilar to the human hormones than the analogs listed in Table 1. The approach to designing single chain glycoprotein hormones is similar to that listed in Examples 12–21 except that the coding sequences for the nonhuman α-subunits are substituted for the human α-subunit sequences illustrated. Similarly, the glycosylation signals can be removed by altering the codons for asparagine or serine or threonine or inserting a proline between asparagine and the serine or threonine.

In addition, when using the template strategy to design immunogens it is often desirable to start with a nonhuman molecule that has little, if any affinity for the templates used in positive selection and to introduce residues that will result in selection. These analogs can be prepared by substituting the FSH, LH, or TSH β-subunit sequences from nonhuman sources in place of the human FSH, LH, and hCG sequences illustrated in Examples 5–18 and Table 1.

TABLE 1

Structures of Single Chain Gonadotropins

| Analog | Composition |
|---|---|
| 1 | n-hCGβ(1–145)-Linker-humanα(1–92)-c |
| 2 | n-hCGβ(1–114)-Linker-humanα(1–92)-c |
| 3 | n-hLHβ(1–114)-Linker-humanα(1–92)-c |
| 4 | n-hFSHβ(1–111)-Linker-humanα(1–92)-c |
| 5 | n-hCGβ(1–93 )-hFSHβ(88–111)-Linker-humanα(1–92)-c |
| 6 | n-hCGβ(1–100)-hFSHβ(95–111)-Linker-humanα(1–92)-c |

TABLE 1-continued

Structures of Single Chain Gonadotropins

| Analog | Composition |
|---|---|
| 7 | n-hCGβ(1–100)-hFSHβ(95–108)-Linker-humanα(1–92)-c |
| 8 | n-hCGβ(1–100)-hFSHβ(95–103)-DDPR-Linker-humanα(1–92)-c |
| 9 | n-hFSHβ(1–108)-Linker-humanα(1–92)-c |
| 10 | n-hFSHβ(1–104)-Linker-humanα(1–92)-c |
| 1a | n-hCGβ(1–145)[N13X,N30X]-Linker-humanα(1–92)[N52X,N78X]-c |
| 2a | n-hCGβ(1–114)[N13X,N30X]-Linker-humanα(1–92)[N52X,N78X]-c |
| 3a | n-hLHβ(1–114)[N30X]-Linker-humanα(1–92)[N52X,N78X]-c |
| 4a | n-hFSHβ(1–111)[N7X,N24X]-Linker-humanα(1–92)[N52X,N78X]-c |
| 5a | n-hCGβ(1–93)[N13X,N30X]-hFSHβ(88–111)-Linker-humanα(1–92)[N52X,N78X]-c |
| 6a | n-hCGβ(1–100)[N13X,N30X]-hFSHβ(95–111)-Linker-humanα(1–92)[N52X,N78X]-c |
| 7a | n-hCGβ(1–100)[N13X,N30X]-hFSHβ(95–108)-Linker-humanα(1–92)[N52X,N78X]-c |
| 8a | n-hCGβ(1–100)[N13X,N30X]-hFSHβ(95–103)-DDPR-Linker-humanα(1–92)[N52X,N78X]-c |
| 9a | n-hFSHβ(1–108)-Linker-humanα(1–92)-[N52X,N78X]-c |
| 10a | n-hFSHβ(1–104)[N7X,N24X]-Linker-humanα(1–92)-c |
| 1b | n-hCGβ(1–145)[N13X,N30X,P78X,V79T]-Linker-humanα(1–92)[N52X,N78X]-c |
| 2b | n-hCGβ(1–114)[N13X,N30X,P78X,V79T]-Linker-humanα(1–92)[N52X,N78X]-c |
| 3b | n-hLHβ(1–114)[N30X,P78X,V79T]-Linker-humanα(1–92)[N52X,N78X]-c |
| 4b | n-hFSHβ(1–111)[N7X,N24X,D71N,L73T]-Linker-humanα(1–92)[N52X,N78X]-c |
| 5b | n-hCGβ(1–93)[N13X,N30X,P78X,V79T]-hFSHβ(88–111)-Linker-humanα(1–92)[N52X,N78X]-c |
| 6b | n-hCGβ(1–100)[N13X,N30X,P78X,V79T]-hFSHβ(95–111)-Linker-humanα(1–92)[N52X,N78X]-c |
| 7b | n-hCGβ(1–100)[N13X,N30X,P78X,V79T]-hFSHβ(95–108)-Linker-humanα(1–92)[N52X,N78X]-c |
| 8b | n-hCGβ(1–100)[N13X,N30X,P78X,V79T]-hFSHβ(95–103)-DDPR-Linker-humanα(1–92)[N52X,N78X]-c |
| 9b | n-hFSHβ(1–108)[N7X,N24X,D71N,L73T]-Linker-humanα(1–92)-[N52X,N78X]-c |
| 10b | n-hFSHβ(1–104)[N7X,N24X,D71N,L73T]-Linker-humanα(1–92)-[N52X,N78X]-c |

Definitions of the Letters and Sequences in Table 1

"n-" refers to the N-terminus of the protein.

"-c" refers to the C-terminus of the protein.

"hCGβ(1–145)" refers to the hCG β-subunit amino acid sequence residues 1–145:

SKEPLRPRCRPfNATLAVEKEGCPVCITVNTTICAG YCPTMTRVLQGVLPA LPQVVCNYRDVRFESIRLPGCPRGVNPVVSYAVAL SCQCALCRRSTTDCGGPKD HPLTCDDPRFQDSSSSKAPPPSLPSPSRLPGPSDTP ILPO (SEQ ID NO:68)

"hCGβ(1–114)" refers to the hCG β-subunit amino acid sequence residues 1–114:

SKEPLRPRCRPINATLAVEKEGCPVCITVNTTICAG YCPTMTRVLQGVLPA LPQVVCNYRDVRFESIRLPGCPRGVNPVVSYAVAL SCQCALCRRSTTDCGGPKD HPLTCDDPR (SEQ ID NO:69)

"hCGβ(1–93)" refers to the hCG β-subunit amino acid sequence residues 1–93:

SKEPLRPRCRPINATLAVEKEGCPVCITVNTTICAG YCPTMTRVLQGVLPA LPQVVCNYRDVRFESIRLPGCPRGVNPVVSYAVAL SCQCALC (SEQ ID NO:70)

"hLHβ(1–114)" refers to the hLH β-subunit amino acid sequence residues 1–114:

SREPLRPWCHPINAILAVEKEGCPVCITVNTTICAG YCPTMMRVLQAVLPP LPQVVCTYRDVRFESIRLPGCPRGVDPVVSFPVAL SCRCGPCRRSTSDCGGPKDH PLTCDRPQ (SEQ ID NO:71)

"hFSHβ(1–111)" refers to the hFSH β-subunit amino acid sequence residues 1–111:

NSCELTNITIAVEKEGCGFCITINTTWCAGYCYTRD LVYKDPARPKIQKTC TFKELVYETVRVPGCAHHADSLYTYPVATQCHCG KCDSDSTDCTVRGLGPSYCS FGEMKE (SEQ ID NO:72)

"hFSHβ(1–108)" refers to the hFSH β-subunit amino acid sequence residues 1–108:

NSCELTNITIAVEKEGCGFCITINTTWCAGYCYTRD LVYKDPARPKIQKTC TFKELVYETVRVPGCAHHADSLYTYPVATQCHCG KCDSDSTDCTVRGLGPSYCS FGE (SEQ ID NO:73)

"hFSHβ(1–104)" refers to the hFSH β-subunit amino acid sequence residues 1–104:

NSCELTNITIAVEKEGCGFCITfNTTWCAGYCYTRD LVYKDPARPKIQKTC TFKELVYETVRVPGCAHHADSLYTYPVATQCHCG KCDSDSTDCTVRGLGPSYC (SEQ ID NO:7)

"hFSHβ(88–111)" refers to the hFSH β-subunit amino acid sequence residues 88–111:

DSDSTDCTVRGLGPSYCSFGEMKE (SEQ ID NO:75)

"hFSHβ(95–111)" refers to the hFSH β-subunit amino acid sequence residues 95–111:

TVRGLGPSYCSFGEMKE (SEQ ID NO:76)

"hFSHβ(95–108)" refers to the hFSH βsubunit amino acid sequence residues 95–108:

TVRGLGPSYCSFGE (SEQ ID NO:77)

"hFSHβ(95–103)" refers to the hFSH β-subunit amino acid sequence residues 95–103:

TVRGLPSY (SEQ ID NO:78)

"N13X" refers to the substitution of glutamine or other amino acid for hCG β-subunit residue asparagine 13 and analogs "N30X" refers to the substitution of glutamine or other amino acid for hCG or hLH β-subunit residue asparagine 30 and analogs "N52X" refers to the substitution of glutamine or other amino acid for human α-subunit residue asparagine 52 and analogs "N78X" refers to the substitution of glutamine or other amino acid for human α-subunit residue asparagine 78 and analogs "P78X" refers to the substitution of any amino acid except proline for proline 78 in the β-subunits of hCG or hLH and analogs "V79T" refers to the substitution of threonine or serine for valine 79 in hCG or hLH β-subunit and analogs "D71 IN" refers to the substitution of asparagine for aspartic acid 71 in hFSH β-subunits and analogs "L73T" refers to the substitution of threonine or serine for leucine 73 in hFSH β-subunits and analogs "humanα(1–92)" refers to the human α-subunit sequence residues 1–92

APDVQDCPECTLQENPFFSQPGAPILQCMGCCFSR
AYPTPLRSKKTMLVQK
NVTSESTCCVAKSYNRVTVMGGFKVENHTACHCS
TCYYHKS (SEQ ID NO:79)

"Linker" refers to a sequence containing repeating glycine and serine amino acids such as GS, GSGS (SEQ ID NO:80), GSGSGS (SEQ ID NO:81), GSGSGSGS (SEQ ID NO:52), GSGSGSGSGS (SEQ ID NO:82) or any other sequence of amino acids that permits the β- and α-subunit sequences of the single chain gonadotropin to form a complex in which the α- and β-subunit portions combine with the β- and α-subunit portions of the same or other molecule.

"DDPR (SEQ ID NO:83) " refers to the amino acid sequence Asparagine-Asparagine-Proline-Arginine.

Notes for Table 1

1. The order of the components from left to right in the table is the order in which the components occur in the protein from the amino-terminus to the carboxy-terminus.

2. Due to the high conservation of sequence in all vertebrate gonadotropins that can be seen from the alignment of their cysteine residues, single chain gonadotropins can be prepared by substitution of any homologous residues for the corresponding portions of the hCG, hLH, and hFSH β-subunits.

3. The sequence of the other vertebrate gonadotropin α-subunits can be substituted for humanÂ(1–92). This includes but is not limited to bovine α-subunit residues 1–96.

4. As shown, the order of the components has the sequences derived from the β-subunit amino-terminal of the sequences derived from the α-subunit. The order of the components in the table can be reversed such that the α-subunit sequences are amino-terminal of the β-subunit sequences.

5. The amino acid sequences are shown in the standard single letter code except as noted.

6. Coding sequences for all these analogs can be made by standard recombinant DNA methods that are well known in the art. One procedure for making these is that provided by Campbell et al. (54). They can be expressed in eukaryotic cells by methods well known in the art using vectors that have been designed for eukaryotic expression and that are available from InVitrogen, San Diego, Calif. Those that do not contain oligosaccharide chains can also be made in *E. coli* by methods well known in the art using vectors such as the pET vectors that can be obtained from Novagen.

7. The glycosylation sites at hCG β-subunit asparagines 13 and/or 30 can be destroyed by substitution of the asparagine as illustrated and/or by substitution of residues 14 and/or 31 with a proline and/or by substitution of residues 15 and/or 32 with any other amino acid other than serine or threonine.

8. The glycosylation site at hLH β-subunit asparagine 30 can be destroyed by substitution of the asparagine as illustrated and/or by substitution of residue 31 with a proline and/or by substitution of residue 32 with any other amino acid other than serine or threonine.

9. The glycosylation sites at human α-subunit asparagines 52 and/or 78 can be destroyed by substitution of the asparagine as illustrated and/or by substitution of residues 53 and/or 79 with a proline and/or by substitution of residues 54 and/or 80 with any other amino acid other than serine or threonine.

10. The glycosylation sites at nonhuman α-subunit asparagines 56 and/or 82 can be destroyed by substitution of the asparagine with any other amino acid and/or by substitution of residues 57 and/or 83 with a proline and/or by substitution of residues 58 and/or 84 with any other amino acid other than serine or threonine.

TABLE 2

Properties and uses of the analogs illustrated in Table 1

| Analog | Activity | Use |
|---|---|---|
| 1 | LH | Induce ovulation; Increase male fertility |
| 2 | LH | Induce ovulation; Increase male fertility |
| 3 | LH | Induce ovulation; Increase male fertility |
| 4 | FSH | Induce follicle development; Increase male fertility |
| 5 | FSH | Induce follicle development; Increase male fertility |
| 6 | FSH and LH | Induce follicle development; Increase male fertility |
| 7 | FSH and LH | Induce follicle development; Increase male fertility |
| 8 | FSH and LH | Induce follicle development; Increase male fertility |
| 9 | FSH | Induce follicle development; Increase male fertility |
| 10 | FSH | Induce follicle development; Increase male fertility |
| 1a | Anti-LH | *Facilitate ovulation; Terminate pregnancy; Reduce androgen secretion |
| 2a | Anti-LR | *Facilitate ovulation; Terminate pregnancy; Reduce androgen secretion |
| 3a | Anti-LH | *Facilitate ovulation; Terminate pregnancy; Reduce androgen secretion |
| 4a | Anti-FSH | Treat ovarian hyperstimulation; Reduce spermatogenesis |
| 5a | Anti-FSH | Treat ovarian hyperstimulation; Reduce spermatogenesis |
| 6a | Anti-FSH and Anti-LH | Treat ovarian hyperstimulation; Reduce spermatogenesis |
| 7a | Anti-FSH and Anti-LH | Treat ovarian hyperstimulation; Reduce spermatogenesis |
| 8a | Anti-FSH and Anti-LH | Treat ovarian hyperstimulation; Reduce spermatogenesis |
| 9a | Anti-FSH | Treat ovarian hyperstimulation; Reduce spermatogenesis |
| 10a | Anti-FSH | Treat ovarian hyperstimulation; Reduce spermatogenesis |
| 1b | Anti-LH | *Facilitate ovulation; Terminate pregnancy; Reduce androgen secretion |
| 2b | Anti-LH | *Facilitate ovulation; Terminate pregnancy; Reduce androgen secretion |
| 3b | Anti-LH | *Facilitate ovulation; Terminate pregnancy; Reduce androgen secretion |
| 4b | Anti-FSH | Treat ovarian hyperstimulation; Reduce spermatogenesis |
| 5b | Anti-FSH | Treat ovarian hyperstimulation; Reduce spermatogenesis |
| 6b | Anti-FSH and Anti-LH | Treat ovarian hyperstimulation; Reduce spermatogenesis |
| 7b | Anti-FSH and Anti-LH | Treat ovarian hyperstimulation; Reduce spermatogenesis |
| 8b | Anti-FSH and Anti-LH | Treat ovarian hyperstimulation; Reduce spermatogenesis |
| 9b | Anti-FSH | Treat ovarian hyperstimulation; Reduce spermatogenesis |
| 10b | Anti-FSH | Treat ovarian hyperstimulation; Reduce spermatogenesis. |

The compounds of the present invention can be administered to mammals, e.g., animals or humans, in amounts effective to provide the desired therapeutic effect. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient.

Throughout this application, various publications have been referenced, The disclosures in these publications are incorporated herein by reference in order to more fully describe the state of the art.

What is claimed is:

1. A DNA or RNA molecule which comprises a nucleotide sequence that encodes single-chain protein which is an agonist or antagonist of a hormone selected from the group consisting of luteinizing hormone (LH), follicle stimulating hormone (FSH), thyroid stimulating hormone (TSH) and chorionic gonadotropin (CG), which single-chain protein has an amino acid sequence of the formula β-(linker)$_n$-α or α-(linker)$_n$-β wherein β is the β subunit of LH, FSH, TSH or CG or a variant thereof;

"linker" refers to a peptide linker containing 1–100 amino acids;

n is 0 or 1, and

α represents the amino acid sequence of the α subunit common to LH FSH, TSH and CG or a variant thereof.

2. The DNA or RNA molecule of claim 1 wherein the nucleotide sequence encodes a protein wherein n is zero.

3. The DNA or RNA molecule of claim 1 wherein the nucleotide sequence encodes a protein wherein n is 1 and the linker is a complete CTP unit consisting of amino acid residues 112–118 to 145 of human chorionic gonadotropin β subunit.

4. The DNA or RNA molecule of claim 1 wherein the nucleotide sequence encodes a protein wherein n is 1 and the linker is a peptide containing 1–16 amino acids.

5. The DNA or RNA molecule of claim 1 wherein the nucleotide sequence encodes a protein wherein n is 1 and the linker is a glycine/serine repeat.

6. The DNA or RNA molecule of claim 1 wherein the nucleotide sequence encodes a protein wherein the α subunit or β subunit or both are modified by the insertion of a complete or partial CTP unit or variant thereof into a noncritical region thereof and/or wherein said linker includes a complete or partial CTP unit or variant thereof, wherein CTP refers to the amino acid sequence found at the carboxy terminus of human chorionic gonadotropin β subunit which extends from amino acid residues 112–118 to residue 145, and said partial CTP unit includes at least one glycosylation site.

7. The DNA or RNA molecule of claim 1 wherein the nucleotide sequence encodes a protein wherein said variants contain 1–5 conservative amino acid substitutions as referred to the native forms or are truncated forms of said sequences or both.

8. The DNA or RNA molecule of claim 1 wherein the nucleotide sequence encodes a protein wherein the α and β subunits are human α and β subunits or their variants.

9. The DNA or RNA molecule of claim 1 wherein the nucleotide sequence encodes a protein wherein selected from the group consisting of formulas 1–10, 1a–10a, and 1b–10b of Table 1.

10. The DNA or RNA molecule of claim 1 wherein the nucleotide sequence encodes a protein wherein β is the β subunit of TSH or a variant thereof.

11. An expression system for the production of an agonist or antagonist of LH, FSH, TSH or CG which comprises the nucleotide sequence of claim 1 operably linked to control sequences which effects its expression in a compatible host cell.

12. The expression system of claim 11 wherein the nucleotide sequence encodes a protein wherein n is zero.

13. The expression system of claim 11 wherein the nucleotide sequence encodes a protein wherein n is 1 and the linker is a complete CTP unit consisting of amino acid residues 112–118 to 145 of human chorionic gonadotropin β subunit.

14. The expression system of claim 11 wherein the nucleotide sequence encodes a protein wherein n is 1 and the linker is a peptide containing 1–16 amino acids.

15. The expression system of claim 11 wherein the nucleotide sequence encodes a protein wherein the linker is a glycine/serine repeat.

16. The expression system of claim 11 wherein the nucleotide sequence encodes a protein wherein the α subunit or β subunit or both are modified by the insertion of a complete or partial CTP unit or variant thereof into a noncritical region thereof and/or wherein said linker includes a complete or partial CTP unit or variant thereof, wherein CTP refers to the amino acid sequence found at the carboxy terminus of human chorionic gonadotropin β subunit which extends from amino acid residues 112–118 to residue 145, or a portion thereof or a variant thereof.

17. The expression system of claim 11 wherein the nucleotide sequence encodes a protein wherein said variants contain 1–5 conservative amino acid substitutions as referred to the native forms or are truncated forms of said sequences or both.

18. The expression system of claim 11 wherein the nucleotide sequence encodes a protein wherein the α and β subunits are human α, and β subunits or their variants.

19. The expression system of claim 11 wherein the nucleotide sequence encodes a protein wherein selected from the group consisting of formulas 1–10, 1a–10a, and 1b–10b of Table 1.

20. The expression system of claim 11 wherein the nucleotide sequence encodes a protein wherein β is the β subunit of TSH or a variant thereof.

21. Recombinant host cells modified to contain the expression system of claim 11.

22. Recombinant host cells modified to contain the expression system of claim 12.

23. Recombinant host cells modified to contain the expression system of claim 13.

24. Recombinant host cells modified to contain the expression system of claim 14.

25. Recombinant host cells modified to contain the expression system of claim 15.

26. Recombinant host cells modified to contain the expression system of claim 16.

27. Recombinant host cells modified to contain the expression system of claim 17.

28. Recombinant host cells modified to contain the expression system of claim 18.

29. Recombinant host cells modified to contain the expression system of claim 19.

30. Recombinant host cells modified to contain the expression system of claim 20.

31. A method to produce an agonist or antagonist of LH, FSH, TSH or CG which method comprises culturing the cells of claim 21 under conditions wherein said agonist or antagonist is produced and
   optionally recovering said agonist or antagonist from the cell culture.

32. A method to produce an agonist or antagonist of LH, FSH, TSH or CG which method comprises culturing the cells of claim 22 under conditions wherein said agonist or antagonist is produced and
   optionally recovering said agonist or antagonist from the cell culture.

33. A method to produce an agonist or antagonist of LH, FSH, TSH or CG which method comprises culturing the cells of claim 23 under conditions wherein said agonist or antagonist is produced and
   optionally recovering said agonist or antagonist from the cell culture.

34. A method to produce an agonist or antagonist of LH, FSH, TSH or CG which method comprises culturing the cells of claim 24 under conditions wherein said agonist or antagonist is produced and
   optionally recovering said agonist or antagonist from the cell culture.

35. A method to produce an agonist or antagonist of LH, FSH, TSH or CG which method comprises culturing the cells of claim 25 under conditions wherein said agonist or antagonist is produced and
   optionally recovering said agonist or antagonist from the cell culture.

36. A method to produce an agonist or antagonist of LH, FSH, TSH or CG which method comprises culturing the cells of claim 26 under conditions wherein said agonist or antagonist is produced and
   optionally recovering said agonist or antagonist from the cell culture.

37. A method to produce an agonist or antagonist of LH, FSH, TSH or CG which method comprises culturing the cells of claim 27 under conditions wherein said agonist or antagonist is produced and
   optionally recovering said agonist or antagonist from the cell culture.

38. A method to produce an agonist or antagonist of LH, FSH, TSH or CG which method comprises culturing the cells of claim 28 under conditions wherein said agonist or antagonist is produced and
   optionally recovering said agonist or antagonist from the cell culture.

39. A method to produce an agonist or antagonist of LH, FSH, TSH or CG which method comprises culturing the cells of claim 29 under conditions wherein said agonist or antagonist is produced and
   optionally recovering said agonist or antagonist from the cell culture.

40. A method to produce an agonist or antagonist of LH, FSH, TSH or CG which method comprises culturing the cells of claim 30 under conditions wherein said agonist or antagonist is produced and
   optionally recovering said agonist or antagonist from the cell culture.

\* \* \* \* \*